US012714449B2

(12) United States Patent
Staab et al.

(10) Patent No.: US 12,714,449 B2
(45) Date of Patent: Aug. 25, 2026

(54) CONTROL OF IVL SYSTEMS, DEVICES AND METHODS THEREOF

(71) Applicant: Cardiovascular Systems, Inc., Santa Clara, CA (US)

(72) Inventors: Jason W. Staab, Apple Valley, MN (US); Austin P. Petronack, Plymouth, MN (US); John R. Ballard, Waconia, MN (US); J. Samuel Batchelder, Woodinville, WA (US); Jacob T. Williams, Plymouth, MN (US); Donald D. Hanson, Chaska, MN (US); Thomas D. Brindley, Plymouth, MN (US); Scott P. Boeshart, Maple Grove, MN (US); Jeffrey T. Moriarty, Roseville, MN (US)

(73) Assignee: Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 19/170,999

(22) Filed: Apr. 4, 2025

(65) Prior Publication Data

US 2025/0255630 A1 Aug. 14, 2025

Related U.S. Application Data

(63) Continuation of application No. PCT/US2023/079209, filed on Nov. 9, 2023.
(Continued)

(51) Int. Cl.
*A61B 17/22* (2006.01)
*A61B 17/00* (2006.01)
(Continued)

(52) U.S. Cl.
CPC .. *A61B 17/22022* (2013.01); *A61B 17/00234* (2013.01); *A61B 18/1492* (2013.01);
(Continued)

(58) Field of Classification Search
CPC ........ A61B 17/22022; A61B 17/00234; A61B 2017/00185; A61B 2017/0019;
(Continued)

(56) References Cited

U.S. PATENT DOCUMENTS 2,916,647 A 12/1959 George
3,412,288 A 11/1968 Ostrander
(Continued)

FOREIGN PATENT DOCUMENTS

AT E482647 T1 10/2010
AU 22933/88 A 4/1989
(Continued)

OTHER PUBLICATIONS

International Search Report issued in PCT/US2022/74607, mailed Oct. 25, 2022.
(Continued)

*Primary Examiner* — Brooke Labranche
*Assistant Examiner* — Rachael L Geiger
(74) *Attorney, Agent, or Firm* — WORKMAN NYDEGGER

(57) ABSTRACT

A catheter system (100) for treating a vascular lesion (106) within or adjacent to a heart valve (108) within a body (107) of a patient (109), includes an energy source (124), and a plurality of spaced apart treatment devices (143). The energy source (124) generates energy. Each treatment device (143) includes (i) a balloon (104) that is positionable substantially adjacent to the vascular lesion (106), the balloon (104) having a balloon wall (130) that defines a balloon interior (146), the balloon (104) being configured to retain a balloon
(Continued)

fluid (132) within the balloon interior (146); and (ii) at least one of a plurality of energy guides (122A) that receive energy from the energy source (124) so that plasma (134) is formed in the balloon fluid (132) within the balloon interior (146).

23 Claims, 14 Drawing Sheets

Related U.S. Application Data

(60) Provisional application No. 63/580,547, filed on Sep. 5, 2023, provisional application No. 63/424,573, filed on Nov. 11, 2022.

(51) Int. Cl.
*A61B 18/00* (2006.01)
*A61B 18/14* (2006.01)
*G16H 40/63* (2018.01)
*H02J 7/00* (2006.01)
*H02J 7/50* (2026.01)
*H02J 7/90* (2026.01)

(52) U.S. Cl.
CPC ............... *G16H 40/63* (2018.01); *H02J 7/50* (2026.01); *H02J 7/90* (2026.01); *A61B 2017/00017* (2013.01); *A61B 2017/00181* (2013.01); *A61B 2017/00185* (2013.01); *A61B 2017/0019* (2013.01); *A61B 2017/00238* (2013.01); *A61B 2017/00292* (2013.01); *A61B 2017/00305* (2013.01); *A61B 2017/00557* (2013.01); *A61B 2017/00734* (2013.01); *A61B 2017/00778* (2013.01); *A61B 2017/22025* (2013.01); *A61B 2017/22062* (2013.01); *A61B 2017/22065* (2013.01); *A61B 2018/0022* (2013.01); *A61B 2018/00404* (2013.01); *A61B 2018/00767* (2013.01); *H02J 2207/20* (2020.01)

(58) Field of Classification Search
CPC ........... A61B 2017/00238; A61B 2017/00305; A61B 2017/22025; A61B 2017/22062; G16H 40/63
See application file for complete search history.

(56) References Cited

U.S. PATENT DOCUMENTS 3,413,976 A 12/1968 Roze
3,524,101 A 8/1970 Barbini
3,583,766 A 6/1971 Padberg, Jr.
3,735,764 A 5/1973 Balev et al.
3,785,382 A 1/1974 Schmidt et al.
3,902,499 A 9/1975 Shene
3,942,531 A 3/1976 Hoff et al.
4,027,674 A 6/1977 Tessler et al.
4,030,505 A 6/1977 Tessler
4,191,189 A 3/1980 Barkan
4,445,509 A 5/1984 Auth
4,446,867 A 5/1984 Leveen et al.
4,587,975 A 5/1986 Salo et al.
4,608,983 A 9/1986 Mueller et al.
4,643,186 A 2/1987 Rosen et al.
4,662,126 A 5/1987 Malcolm
4,662,375 A 5/1987 Hepp et al.
4,671,254 A 6/1987 Fair
4,685,458 A 8/1987 Leckrone
4,697,588 A 10/1987 Reichenberger
4,702,248 A 10/1987 Mestas et al.
4,715,375 A 12/1987 Nowacki et al.
4,715,376 A 12/1987 Nowacki et al.
4,741,405 A 5/1988 Moeny et al.
4,766,608 A 8/1988 Cusick et al.
4,781,677 A 11/1988 Wilcox
4,793,329 A 12/1988 Mahler et al.
4,799,482 A 1/1989 Takayama
4,809,682 A 3/1989 Forssmann et al.
4,813,934 A 3/1989 Engelson et al.
4,878,495 A 11/1989 Grayzel
4,890,603 A 1/1990 Filler
4,900,303 A 2/1990 Lemelson
4,901,709 A 2/1990 Rattner
4,905,673 A 3/1990 Pimiskern
4,905,675 A 3/1990 Oppelt
4,909,252 A 3/1990 Goldberger
4,915,094 A 4/1990 Lacruche et al.
4,930,496 A 6/1990 Bosley, Jr.
4,936,281 A 6/1990 Stasz
4,955,143 A 9/1990 Hagelauer
4,955,377 A 9/1990 Lennox et al.
4,955,385 A 9/1990 Kvalo et al.
4,961,738 A 10/1990 Mackin
4,962,753 A 10/1990 Cathignol et al.
4,966,132 A 10/1990 Nowacki et al.
4,968,314 A 11/1990 Michaels
4,990,134 A 2/1991 Auth
4,994,032 A 2/1991 Sugiyama et al.
4,998,932 A 3/1991 Rosen et al.
5,002,085 A 3/1991 Fitzgerald
5,009,232 A 4/1991 Hassler et al.
5,040,548 A 8/1991 Yock
5,046,503 A 9/1991 Schneiderman
5,057,103 A 10/1991 Davis
5,057,106 A 10/1991 Kasevich et al.
5,057,107 A 10/1991 Parins et al.
5,061,240 A 10/1991 Cherian
5,072,723 A 12/1991 Viebach
5,078,717 A 1/1992 Parins et al.
5,102,402 A 4/1992 Dror et al.
5,103,804 A 4/1992 Abele et al.
5,116,227 A 5/1992 Levy
5,146,912 A 9/1992 Eizenhoefer
5,152,767 A 10/1992 Sypal et al.
5,152,768 A 10/1992 Bhatta
5,154,722 A 10/1992 Filip et al.
5,176,675 A 1/1993 Watson et al.
5,195,508 A 3/1993 Mueller et al.
5,211,683 A 5/1993 Maginot
5,231,976 A 8/1993 Wiksell
5,233,980 A 8/1993 Mestas et al.
5,245,988 A 9/1993 Einars et al.
5,246,447 A 9/1993 Rosen et al.
5,254,121 A 10/1993 Manevitz et al.
5,281,231 A 1/1994 Rosen et al.
5,295,958 A 3/1994 Shturman
5,304,134 A 4/1994 Kraus et al.
5,304,220 A 4/1994 Maginot
5,308,354 A 5/1994 Zacca et al.
5,320,634 A 6/1994 Vigil et al.
5,321,715 A 6/1994 Trost
5,324,255 A 6/1994 Passafaro et al.
5,336,234 A 8/1994 Vigil et al.
5,358,487 A 10/1994 Miller
5,362,309 A 11/1994 Carter
5,364,393 A 11/1994 Auth et al.
5,366,443 A 11/1994 Eggers et al.
5,368,591 A 11/1994 Lennox et al.
5,395,335 A 3/1995 Jang
5,395,361 A 3/1995 Fox et al.
5,411,016 A 5/1995 Kume et al.
5,417,208 A 5/1995 Winkler
5,425,735 A 6/1995 Rosen et al.
5,429,617 A 7/1995 Hammersmark et al.
5,431,663 A 7/1995 Carter
5,433,731 A 7/1995 Hoegnelid et al.
5,454,809 A 10/1995 Janssen
5,456,712 A 10/1995 Maginot
5,458,652 A 10/1995 Uebelacker
5,470,352 A 11/1995 Rappaport

(56) References Cited

U.S. PATENT DOCUMENTS 5,472,406 A 12/1995 Torre et al.
5,474,080 A 12/1995 Hughes
5,520,645 A 5/1996 Imran et al.
5,571,167 A 11/1996 Maginot
5,582,578 A 12/1996 Zhong et al.
5,584,843 A 12/1996 Wulfman et al.
5,603,731 A 2/1997 Whitney
5,609,606 A 3/1997 O'Boyle
5,611,807 A 3/1997 O'Boyle
5,662,590 A 9/1997 Torre et al.
5,681,336 A 10/1997 Clement et al.
5,709,676 A 1/1998 Alt
5,741,246 A 4/1998 Prescott
5,749,375 A 5/1998 Maginot
5,766,152 A 6/1998 Morley et al.
5,836,874 A 11/1998 Swanson et al.
5,841,737 A 11/1998 Schaefer
5,846,218 A 12/1998 Brisken et al.
5,891,089 A 4/1999 Katz et al.
5,893,840 A 4/1999 Hull et al.
5,931,805 A 8/1999 Brisken
5,967,984 A 10/1999 Chu et al.
5,979,455 A 11/1999 Maginot
5,995,871 A 11/1999 Knisley
6,001,069 A 12/1999 Tachibana et al.
6,007,530 A 12/1999 Doernhoefer et al.
6,033,371 A 3/2000 Torre et al.
6,056,722 A 5/2000 Jayaraman
6,080,119 A 6/2000 Schwarze et al.
6,083,232 A 7/2000 Cox
6,090,104 A 7/2000 Webster, Jr.
6,113,560 A 9/2000 Simnacher
6,123,718 A 9/2000 Tu et al.
6,132,444 A 10/2000 Shturman et al.
6,146,358 A 11/2000 Rowe
6,186,963 B1 2/2001 Schwarze et al.
6,210,408 B1 4/2001 Chandrasekaran et al.
6,215,734 B1 4/2001 Moeny et al.
6,217,531 B1 4/2001 Reitmajer
6,267,747 B1 7/2001 Samson et al.
6,277,138 B1 8/2001 Levinson et al.
6,287,272 B1 9/2001 Brisken et al.
6,287,331 B1 9/2001 Heath
6,352,535 B1 3/2002 Lewis et al.
6,364,894 B1 4/2002 Healy et al.
6,367,203 B1 4/2002 Graham et al.
6,371,971 B1 4/2002 Tsugita et al.
6,375,651 B2 4/2002 Grasso et al.
6,390,995 B1 5/2002 Ogden et al.
6,398,792 B1 6/2002 O'Connor
6,401,721 B1 6/2002 Maginot
6,406,486 B1 6/2002 Torre et al.
6,440,124 B1 8/2002 Esch et al.
6,456,888 B1 9/2002 Skinner et al.
6,464,660 B2 10/2002 Brisken et al.
6,494,890 B1 12/2002 Shturman et al.
6,500,174 B1 12/2002 Maguire et al.
6,514,203 B2 2/2003 Bukshpan
6,524,251 B2 2/2003 Rabiner et al.
6,589,253 B1 7/2003 Cornish et al.
6,599,313 B1 7/2003 Maginot
6,607,003 B1 8/2003 Wilson
6,635,054 B2 10/2003 Fjield et al.
6,638,246 B1 10/2003 Naimark et al.
6,652,547 B2 11/2003 Rabiner et al.
6,666,828 B2 12/2003 Greco et al.
6,666,834 B2 12/2003 Restle et al.
6,669,655 B1 12/2003 Acker et al.
6,689,089 B1 2/2004 Tiedtke et al.
6,726,681 B2 4/2004 Grasso et al.
6,736,784 B1 5/2004 Menne et al.
6,736,811 B2 5/2004 Panescu et al.
6,740,081 B2 5/2004 Hilal
6,755,821 B1 6/2004 Fry
6,758,847 B2 7/2004 Maguire
6,761,708 B1 7/2004 Chiu et al.
6,800,080 B1 10/2004 Bates
6,939,320 B2 9/2005 Lennox
6,954,977 B2 10/2005 Maguire et al.
6,989,009 B2 1/2006 Lafontaine
7,033,383 B1 4/2006 Maginot
7,066,904 B2 6/2006 Rosenthal et al.
7,087,061 B2 8/2006 Chernenko et al.
7,104,983 B2 9/2006 Grasso et al.
7,153,315 B2 12/2006 Miller
7,175,605 B2 2/2007 Tiedtke et al.
7,241,295 B2 7/2007 Maguire
7,247,269 B2 7/2007 Keidar
7,309,324 B2 12/2007 Hayes et al.
7,379,767 B2 5/2008 Rea
7,389,148 B1 6/2008 Morgan
7,390,308 B2 6/2008 Schultheiss
7,410,486 B2 8/2008 Fuimaono et al.
7,505,812 B1 3/2009 Eggers et al.
7,540,846 B2 6/2009 Harhen et al.
7,569,032 B2 8/2009 Naimark et al.
7,597,697 B1 10/2009 Maginot
7,628,785 B2 12/2009 Hadjicostis et al.
7,651,492 B2 1/2010 Wham
7,720,521 B2 5/2010 Chang et al.
7,736,362 B2 6/2010 Eberl et al.
7,744,595 B2 6/2010 Truckai et al.
7,744,620 B2 6/2010 Pedersen et al.
7,753,946 B2 7/2010 Maginot
7,754,047 B2 7/2010 Kelley
7,829,029 B2 11/2010 Zumeris et al.
7,837,672 B2 11/2010 Intoccia
7,850,685 B2 12/2010 Kunis et al.
7,853,332 B2 12/2010 Olsen et al.
7,855,904 B2 12/2010 Kirbie et al.
7,873,404 B1 1/2011 Patton
7,914,525 B2 3/2011 Abboud et al.
7,920,921 B2 4/2011 Syed et al.
7,942,850 B2 5/2011 Levit et al.
7,951,111 B2 5/2011 Drasler et al.
7,959,602 B2 6/2011 Tiedtke et al.
8,025,661 B2 9/2011 Arnold et al.
8,133,199 B2 3/2012 Weber et al.
8,162,859 B2 4/2012 Schultheiss et al.
8,177,801 B2 5/2012 Kallok et al.
8,182,530 B2 5/2012 Huber
8,197,463 B2 6/2012 Intoccia
8,241,272 B2 8/2012 Arnold et al.
8,277,444 B2 10/2012 Arnold et al.
8,333,763 B2 12/2012 Truckai et al.
8,343,170 B2 1/2013 Massicotte et al.
8,353,923 B2 1/2013 Shturman
8,366,705 B2 2/2013 Arnold et al.
8,382,771 B2 2/2013 Gellman et al.
8,444,639 B2 5/2013 Arnold et al.
8,518,038 B2 8/2013 Swanson
8,529,581 B2 9/2013 Massicotte et al.
8,556,813 B2 10/2013 Cioanta et al.
8,556,890 B2 10/2013 Wham
8,574,247 B2 11/2013 Adams et al.
8,632,461 B2 1/2014 Glossop
8,685,201 B2 4/2014 O'Rourke et al.
8,709,075 B2 4/2014 Adams et al.
8,728,091 B2 5/2014 Hakala et al.
8,747,416 B2 6/2014 Hakala et al.
8,790,359 B2 7/2014 Rabiner et al.
8,805,466 B2 8/2014 Salahieh et al.
8,888,788 B2 11/2014 Hakala et al.
8,897,869 B2 11/2014 Kassab
8,900,166 B2 12/2014 Spector
8,900,264 B2 12/2014 Drasler et al.
8,926,630 B2 1/2015 Diamant et al.
8,956,371 B2 2/2015 Hawkins et al.
8,956,374 B2 2/2015 Hawkins et al.
9,005,198 B2 4/2015 Long et al.
9,005,216 B2 4/2015 Hakala et al.
9,011,462 B2 4/2015 Adams et al.
9,011,463 B2 4/2015 Adams et al.
9,044,618 B2 6/2015 Hawkins et al.

(56) References Cited

U.S. PATENT DOCUMENTS 9,044,619 B2 6/2015 Hawkins et al.
9,072,534 B2 7/2015 Adams et al.
9,119,624 B2 9/2015 Wham
9,138,249 B2 9/2015 Adams et al.
9,161,768 B2 10/2015 Cioanta et al.
9,180,280 B2 11/2015 Hawkins et al.
9,192,772 B1 11/2015 Tsukamoto et al.
9,198,825 B2 12/2015 Katragadda et al.
9,220,521 B2 12/2015 Hawkins et al.
9,277,955 B2 3/2016 Herscher et al.
9,289,258 B2 3/2016 Cohen
9,333,000 B2 5/2016 Hakala et al.
9,375,533 B2 6/2016 Ducharme et al.
9,421,025 B2 8/2016 Hawkins et al.
9,431,428 B2 8/2016 Yamazaki
9,433,428 B2 9/2016 Hakala et al.
9,504,807 B2 11/2016 Drasler et al.
9,522,012 B2 12/2016 Adams
9,579,114 B2 2/2017 Mantell et al.
9,610,006 B2 4/2017 Salahieh et al.
9,636,124 B2 5/2017 Mantell
9,642,673 B2 5/2017 Adams et al.
9,717,513 B2 8/2017 Golan
9,730,715 B2 8/2017 Adams
9,743,980 B2 8/2017 Diamant et al.
9,757,194 B2 9/2017 Werneth et al.
9,763,624 B2 9/2017 Stanislaus et al.
9,808,167 B2 11/2017 Kassab
9,814,476 B2 11/2017 Adams et al.
9,833,373 B2 12/2017 Brouillette et al.
9,861,377 B2 1/2018 Mantell
9,867,629 B2 1/2018 Hawkins
9,913,594 B2 3/2018 Li et al.
9,974,607 B2 5/2018 Stone et al.
9,993,292 B2 6/2018 Adams et al.
10,010,666 B2 7/2018 Rubinsky et al.
10,039,561 B2 8/2018 Adams et al.
10,058,340 B2 8/2018 Cioanta et al.
10,118,015 B2 11/2018 De et al.
10,149,690 B2 12/2018 Hawkins et al.
10,154,799 B2 12/2018 Van et al.
10,159,505 B2 12/2018 Hakala et al.
10,194,930 B2 2/2019 Du
10,201,387 B2 2/2019 Grace et al.
10,206,698 B2 2/2019 Hakala et al.
10,219,720 B2 3/2019 Kassab
10,226,265 B2 3/2019 Ku et al.
10,238,405 B2 3/2019 Cioanta et al.
10,238,408 B2 3/2019 Zhong et al.
10,364,981 B2 7/2019 Wang et al.
10,426,500 B2 10/2019 Lipowski et al.
10,500,128 B2 12/2019 Engles et al.
10,517,620 B2 12/2019 Adams
10,517,621 B1 12/2019 Hakala et al.
10,555,744 B2 2/2020 Nguyen et al.
10,603,058 B2 3/2020 Mantell
10,639,051 B2 5/2020 Cioanta et al.
10,646,240 B2 5/2020 Betelia et al.
10,661,034 B2 5/2020 Mantell et al.
10,668,208 B2 6/2020 Rubinsky et al.
10,682,178 B2 6/2020 Adams et al.
10,702,293 B2 7/2020 Adams et al.
10,709,462 B2 7/2020 Nguyen et al.
10,751,000 B2 8/2020 Hacker
10,756,440 B2 8/2020 Asagi et al.
10,765,440 B2 9/2020 Tozzi
10,786,267 B2 9/2020 Wasdyke et al.
10,806,504 B2 10/2020 Hubelbank
10,842,567 B2 11/2020 Grace et al.
10,849,637 B1 12/2020 Mantell
10,849,879 B2 12/2020 Seward
10,850,078 B2 12/2020 Grace et al.
10,856,893 B2 12/2020 Eggert et al.
10,888,373 B2 1/2021 Koblish et al.
10,893,903 B2 1/2021 Koblish et al.
10,898,213 B2 1/2021 Grace et al.
10,959,743 B2 3/2021 Adams et al.
10,966,737 B2 4/2021 Nguyen
10,973,538 B2 4/2021 Hakala et al.
11,000,299 B2 5/2021 Hawkins et al.
11,020,135 B1 6/2021 Hawkins
11,058,492 B2 7/2021 Grace et al.
11,076,874 B2 8/2021 Hakala et al.
11,103,262 B2 8/2021 Tran et al.
11,160,467 B2 11/2021 Kassab et al.
11,179,169 B2 11/2021 Brouillette et al.
11,219,388 B2 1/2022 Kassab
11,246,659 B2 2/2022 Grace et al.
11,266,817 B2 3/2022 Cope et al.
11,337,713 B2 5/2022 Nguyen et al.
11,432,834 B2 9/2022 Adams
11,478,261 B2 10/2022 Nguyen
11,484,327 B2 11/2022 Anderson et al.
11,534,187 B2 12/2022 Bonutti
11,559,318 B2 1/2023 Lipowski et al.
11,559,319 B2 1/2023 Mantell
11,596,424 B2 3/2023 Hakala et al.
11,602,363 B2 3/2023 Nguyen
11,617,618 B2 4/2023 Koblish et al.
11,622,780 B2 4/2023 Nguyen et al.
11,666,348 B2 6/2023 Cioanta et al.
11,672,554 B1 6/2023 Mantell
11,696,799 B2 7/2023 Adams et al.
11,771,449 B2 10/2023 Adams et al.
11,779,363 B2 10/2023 Vo
11,839,391 B2 12/2023 Schultheis et al.
11,857,212 B2 1/2024 Capelli et al.
11,911,056 B2 2/2024 Anderson et al.
11,925,366 B2 3/2024 Cioanta et al.
11,944,331 B2 4/2024 Anderson et al.
11,950,793 B2 4/2024 Nguyen
11,957,369 B2 4/2024 Batchelder et al.
11,996,649 B1 5/2024 Carpenter
12,004,759 B2 6/2024 Cioanta
12,004,760 B2 6/2024 Cioanta
12,005,210 B2 6/2024 Chisena et al.
12,016,610 B2 6/2024 Flores et al.
12,016,817 B2 6/2024 Engles et al.
12,035,932 B1 7/2024 Nunes et al.
12,048,445 B2 7/2024 Mantell
12,114,923 B2 10/2024 Adams et al.
12,178,458 B1 12/2024 Betelia et al.
12,214,147 B2 2/2025 Gianotti et al.
12,220,141 B2 2/2025 Ullmann
12,318,100 B2 6/2025 Cioanta
12,364,493 B2 7/2025 Cioanta et al.
12,364,494 B2 7/2025 Cioanta et al.
12,426,904 B2 9/2025 Nguyen et al.
12,514,602 B2 1/2026 Schoenle
2001/0037106 A1 11/2001 Shadduck
2001/0044596 A1 11/2001 Jaafar
2002/0045890 A1 4/2002 Celliers et al.
2002/0072705 A1 6/2002 Vrba et al.
2002/0082553 A1 6/2002 Duchamp
2002/0103455 A1 8/2002 Zhang et al.
2002/0169458 A1 11/2002 Connors
2002/0177889 A1 11/2002 Brisken et al.
2002/0198521 A1 12/2002 Maguire
2003/0004434 A1 1/2003 Greco et al.
2003/0014047 A1 1/2003 Woloszko et al.
2003/0065371 A1 4/2003 Satake
2003/0135223 A1 7/2003 Teague et al.
2003/0144654 A1 7/2003 Hilal
2003/0176873 A1 9/2003 Chernenko et al.
2003/0191492 A1 10/2003 Gellman et al.
2003/0229370 A1 12/2003 Miller
2004/0006288 A1 1/2004 Spector et al.
2004/0006307 A1 1/2004 Qureshi et al.
2004/0006333 A1 1/2004 Arnold et al.
2004/0010249 A1 1/2004 Truckai et al.
2004/0024347 A1 2/2004 Wilson et al.
2004/0044308 A1 3/2004 Naimark et al.
2004/0054367 A1 3/2004 Jimenez et al.
2004/0073251 A1 4/2004 Weber

(56) References Cited

U.S. PATENT DOCUMENTS

2004/0097963 A1 5/2004 Seddon
2004/0097996 A1 5/2004 Rabiner et al.
2004/0153109 A1 8/2004 Tiedtke et al.
2004/0162508 A1 8/2004 Uebelacker
2004/0167466 A1 8/2004 Drasler et al.
2004/0172110 A1 9/2004 Satake
2004/0193046 A1 9/2004 Nash et al.
2004/0215139 A1 10/2004 Cohen
2004/0249401 A1 12/2004 Rabiner et al.
2004/0254570 A1 12/2004 Hadjicostis et al.
2005/0010140 A1 1/2005 Forssmann
2005/0015953 A1 1/2005 Keidar
2005/0021013 A1 1/2005 Visuri et al.
2005/0059965 A1 3/2005 Eberl et al.
2005/0075662 A1 4/2005 Pedersen et al.
2005/0090888 A1 4/2005 Hines et al.
2005/0096669 A1 5/2005 Rabiner et al.
2005/0113722 A1 5/2005 Schultheiss
2005/0113822 A1 5/2005 Fuimaono et al.
2005/0159645 A1 7/2005 Bertolero et al.
2005/0171527 A1 8/2005 Bhola
2005/0194583 A1 9/2005 Taylor et al.
2005/0197667 A1 9/2005 Chan et al.
2005/0228343 A1 10/2005 Kelley
2005/0228372 A1 10/2005 Truckai et al.
2005/0228428 A1 10/2005 Ali et al.
2005/0245866 A1 11/2005 Azizi
2005/0249667 A1 11/2005 Tuszynski et al.
2005/0251131 A1 11/2005 Lesh
2005/0256410 A1 11/2005 Rabiner et al.
2005/0267467 A1 12/2005 Paul et al.
2005/0267488 A1 12/2005 Hare et al.
2005/0273130 A1 12/2005 Sell
2006/0004286 A1 1/2006 Chang et al.
2006/0041304 A1 2/2006 Jang et al.
2006/0064081 A1 3/2006 Rosinko
2006/0064082 A1 3/2006 Bonutti
2006/0069424 A1 3/2006 Acosta et al.
2006/0074484 A1 4/2006 Huber
2006/0178685 A1 8/2006 Melsheimer
2006/0184076 A1 8/2006 Gill et al.
2006/0190022 A1 8/2006 Beyar et al.
2006/0200191 A1 9/2006 Zadno-Azizi
2006/0221528 A1 10/2006 Li et al.
2006/0235269 A1 10/2006 Waxman
2006/0241524 A1 10/2006 Lee et al.
2006/0282153 A1 12/2006 Jang
2007/0005053 A1 1/2007 Dando
2007/0016112 A1 1/2007 Schultheiss et al.
2007/0032723 A1 2/2007 Glossop
2007/0038227 A1 2/2007 Massicotte et al.
2007/0078500 A1 4/2007 Ryan et al.
2007/0088380 A1 4/2007 Hirszowicz et al.
2007/0106320 A1 5/2007 Blix et al.
2007/0123851 A1 5/2007 Alejandro et al.
2007/0129667 A1 6/2007 Tiedtke et al.
2007/0156129 A1 7/2007 Kovalcheck
2007/0198047 A1 8/2007 Schon et al.
2007/0201031 A1 8/2007 Axelrod et al.
2007/0225677 A1 9/2007 Rowe et al.
2007/0232964 A1 10/2007 Voss
2007/0239082 A1 10/2007 Schultheiss et al.
2007/0239182 A1 10/2007 Glines et al.
2007/0239253 A1 10/2007 Jagger et al.
2007/0244423 A1 10/2007 Zumeris et al.
2007/0250052 A1 10/2007 Wham
2007/0255270 A1 11/2007 Carney
2007/0270897 A1 11/2007 Skerven et al.
2007/0282301 A1 12/2007 Segalescu et al.
2007/0299392 A1 12/2007 Beyar et al.
2007/0299481 A1 12/2007 Syed et al.
2008/0027464 A1 1/2008 Moll et al.
2008/0039790 A1 2/2008 Hasebe
2008/0058836 A1 3/2008 Moll et al.
2008/0065013 A1 3/2008 Goodin
2008/0065014 A1 3/2008 Von et al.
2008/0097251 A1 4/2008 Babaev
2008/0183111 A1 7/2008 Voss
2008/0188803 A1 8/2008 Jang
2008/0188866 A1 8/2008 Karpiel et al.
2008/0188913 A1 8/2008 Stone et al.
2008/0200896 A1 8/2008 Shmulewitz et al.
2008/0249518 A1 10/2008 Warnking et al.
2008/0249595 A1 10/2008 Mcdaniel
2008/0300610 A1 12/2008 Chambers
2009/0036829 A1 2/2009 Pagel et al.
2009/0036831 A1 2/2009 Howat
2009/0041833 A1 2/2009 Bettinger et al.
2009/0054875 A1 2/2009 Strauss et al.
2009/0069748 A1 3/2009 Schaeffer
2009/0143651 A1 6/2009 Kallback et al.
2009/0157066 A1 6/2009 Satake
2009/0227992 A1 9/2009 Nir et al.
2009/0234282 A1 9/2009 Mcandrew et al.
2009/0247945 A1 10/2009 Levit et al.
2009/0254114 A1 10/2009 Hirszowicz et al.
2009/0299447 A1 12/2009 Jensen et al.
2009/0312768 A1 12/2009 Hawkins et al.
2010/0016862 A1 1/2010 Hawkins et al.
2010/0036294 A1 2/2010 Mantell et al.
2010/0082059 A1 4/2010 Gellman et al.
2010/0094209 A1 4/2010 Drasler et al.
2010/0114020 A1 5/2010 Hawkins et al.
2010/0114065 A1 5/2010 Hawkins et al.
2010/0121322 A1 5/2010 Swanson
2010/0179424 A1 7/2010 Warnking et al.
2010/0228192 A1 9/2010 O'Dea et al.
2010/0229792 A1 9/2010 Yamasaki et al.
2010/0274271 A1 10/2010 Kelley
2010/0286709 A1 11/2010 Diamant et al.
2010/0305565 A1 12/2010 Truckai et al.
2011/0028868 A1 2/2011 Spector
2011/0033807 A1 2/2011 Wang et al.
2011/0034832 A1 2/2011 Cioanta et al.
2011/0064953 A1 3/2011 O'Rourke et al.
2011/0092957 A1 4/2011 Intoccia
2011/0118634 A1 5/2011 Golan
2011/0166570 A1 7/2011 Hawkins et al.
2011/0196412 A1 8/2011 Levit et al.
2011/0208185 A1 8/2011 Diamant et al.
2011/0257523 A1 10/2011 Hastings et al.
2011/0264039 A1 10/2011 Thielen et al.
2011/0270273 A1 11/2011 Moll et al.
2011/0295227 A1 12/2011 Hawkins et al.
2012/0071889 A1 3/2012 Mantell et al.
2012/0095461 A1 4/2012 Herscher et al.
2012/0116289 A1 5/2012 Hawkins et al.
2012/0143177 A1 6/2012 Avitall
2012/0157991 A1 6/2012 Christian
2012/0172696 A1 7/2012 Kaellbaeck et al.
2012/0203255 A1 8/2012 Hawkins et al.
2012/0221013 A1 8/2012 Hawkins et al.
2012/0253358 A1 10/2012 Golan
2013/0030431 A1 1/2013 Adams
2013/0030447 A1 1/2013 Adams
2013/0033968 A1 2/2013 Schaefer et al.
2013/0041355 A1 2/2013 Heeren et al.
2013/0096571 A1 4/2013 Massicotte et al.
2013/0116714 A1 5/2013 Adams et al.
2013/0123694 A1 5/2013 Subramaniyan et al.
2013/0150874 A1 6/2013 Kassab
2013/0253622 A1 9/2013 Hooven
2014/0005576 A1 1/2014 Adams et al.
2014/0039513 A1* 2/2014 Hakala ............. A61B 17/22022 606/128
2014/0039514 A1 2/2014 Adams et al.
2014/0046229 A1* 2/2014 Hawkins .......... A61B 17/22022 601/46
2014/0046353 A1 2/2014 Adams
2014/0052145 A1 2/2014 Adams et al.
2014/0052146 A1 2/2014 Curtis et al.
2014/0052147 A1 2/2014 Hakala et al.
2014/0074076 A1 3/2014 Gertner
2014/0074111 A1 3/2014 Hakala et al.

(56) References Cited

U.S. PATENT DOCUMENTS

| | | | |
|---|---|---|---|
| 2014/0074113 | A1 | 3/2014 | Hakala et al. |
| 2014/0163592 | A1 | 6/2014 | Hawkins et al. |
| 2014/0180278 | A1 | 6/2014 | Abboud et al. |
| 2014/0214061 | A1 | 7/2014 | Adams et al. |
| 2014/0243820 | A1 | 8/2014 | Adams et al. |
| 2014/0243846 | A1 | 8/2014 | Aggerholm et al. |
| 2014/0243847 | A1 | 8/2014 | Hakala et al. |
| 2014/0257323 | A1 | 9/2014 | Mantell |
| 2014/0288570 | A1 | 9/2014 | Adams |
| 2015/0039002 | A1 | 2/2015 | Hawkins |
| 2015/0073430 | A1 | 3/2015 | Hakala et al. |
| 2015/0080995 | A1 | 3/2015 | Seeley et al. |
| 2015/0094703 | A1 | 4/2015 | Zikorus et al. |
| 2015/0238208 | A1 | 8/2015 | Adams et al. |
| 2015/0238209 | A1 | 8/2015 | Hawkins et al. |
| 2015/0320432 | A1 | 11/2015 | Adams |
| 2016/0022295 | A1 | 1/2016 | Mantell |
| 2016/0095610 | A1 | 4/2016 | Lipowski et al. |
| 2016/0101280 | A1 | 4/2016 | Thakkar et al. |
| 2016/0113674 | A1 | 4/2016 | Kelley |
| 2016/0135828 | A1 | 5/2016 | Hawkins et al. |
| 2016/0141892 | A1 | 5/2016 | Li et al. |
| 2016/0151081 | A1 | 6/2016 | Adams et al. |
| 2016/0183957 | A1 | 6/2016 | Hakala et al. |
| 2016/0324534 | A1 | 11/2016 | Hawkins et al. |
| 2016/0331389 | A1 | 11/2016 | Hakala et al. |
| 2016/0354144 | A1 | 12/2016 | Caplan et al. |
| 2017/0000959 | A1 | 1/2017 | Mantell et al. |
| 2017/0020598 | A1 | 1/2017 | Millis et al. |
| 2017/0056035 | A1 | 3/2017 | Adams |
| 2017/0086867 | A1 | 3/2017 | Adams |
| 2017/0135709 | A1 | 5/2017 | Nguyen et al. |
| 2017/0258523 | A1 | 9/2017 | Adams et al. |
| 2017/0274160 | A1 | 9/2017 | Mantell et al. |
| 2017/0303946 | A1 | 10/2017 | Ku et al. |
| 2017/0311965 | A1 | 11/2017 | Adams |
| 2018/0028208 | A1 | 2/2018 | Adams et al. |
| 2018/0098779 | A1 | 4/2018 | Betelia et al. |
| 2018/0153568 | A1 | 6/2018 | Kat-Kuoy |
| 2018/0214166 | A1 | 8/2018 | Mantell |
| 2018/0256250 | A1 | 9/2018 | Adams et al. |
| 2018/0303501 | A1 | 10/2018 | Hawkins |
| 2018/0304053 | A1 | 10/2018 | Eggert et al. |
| 2018/0317946 | A1 | 11/2018 | Adams et al. |
| 2018/0360482 | A1 | 12/2018 | Nguyen |
| 2019/0000491 | A1 | 1/2019 | Schoenle |
| 2019/0069916 | A1 | 3/2019 | Hawkins et al. |
| 2019/0150960 | A1 | 5/2019 | Nguyen et al. |
| 2019/0175198 | A1 | 6/2019 | Ku et al. |
| 2019/0254607 | A1 | 8/2019 | Kllbck et al. |
| 2019/0254692 | A1 | 8/2019 | Hakala et al. |
| 2019/0262594 | A1 | 8/2019 | Ogata et al. |
| 2019/0269426 | A1 | 9/2019 | Hakala et al. |
| 2019/0365400 | A1 | 12/2019 | Adams et al. |
| 2019/0388110 | A1 | 12/2019 | Nguyen et al. |
| 2020/0000484 | A1 | 1/2020 | Hawkins |
| 2020/0022716 | A1 | 1/2020 | Hakala et al. |
| 2020/0038044 | A1 | 2/2020 | Lipowski et al. |
| 2020/0085458 | A1 | 3/2020 | Nguyen et al. |
| 2020/0085459 | A1 | 3/2020 | Adams |
| 2020/0100803 | A1 | 4/2020 | Mantell |
| 2020/0129195 | A1 | 4/2020 | Mcgowan et al. |
| 2020/0129741 | A1 | 4/2020 | Kawwas et al. |
| 2020/0129742 | A1 | 4/2020 | Cope et al. |
| 2020/0246032 | A1 | 8/2020 | Betelia et al. |
| 2020/0281505 | A1 | 9/2020 | Kassab et al. |
| 2020/0289767 | A1 | 9/2020 | Mantell et al. |
| 2020/0297280 | A1 | 9/2020 | Källbäck et al. |
| 2020/0297366 | A1 | 9/2020 | Nguyen et al. |
| 2020/0383724 | A1 | 12/2020 | Adams et al. |
| 2020/0397453 | A1 | 12/2020 | Mcgowan et al. |
| 2020/0398033 | A1 | 12/2020 | Mcgowan et al. |
| 2020/0406010 | A1 | 12/2020 | Massimini et al. |
| 2021/0038237 | A1 | 2/2021 | Adams |
| 2021/0059751 | A1 | 3/2021 | Zhang et al. |
| 2021/0085347 | A1 | 3/2021 | Phan et al. |
| 2021/0085348 | A1 | 3/2021 | Nguyen |
| 2021/0085349 | A1 | 3/2021 | Cioanta et al. |
| 2021/0085350 | A1 | 3/2021 | Cioanta et al. |
| 2021/0085383 | A1 | 3/2021 | Vo et al. |
| 2021/0093342 | A1 | 4/2021 | Cioanta et al. |
| 2021/0128241 | A1 | 5/2021 | Schultheis |
| 2021/0177445 | A1 | 6/2021 | Nguyen |
| 2021/0186613 | A1 | 6/2021 | Cook et al. |
| 2021/0220052 | A1 | 7/2021 | Cook |
| 2021/0228137 | A1 | 7/2021 | Aujla |
| 2021/0267615 | A1 | 9/2021 | Cioanta et al. |
| 2021/0267685 | A1 | 9/2021 | Schultheis et al. |
| 2021/0275247 | A1 | 9/2021 | Schultheis et al. |
| 2021/0282792 | A1 | 9/2021 | Adams et al. |
| 2021/0290259 | A1 | 9/2021 | Hakala et al. |
| 2021/0290305 | A1 | 9/2021 | Cook et al. |
| 2021/0308001 | A1 | 10/2021 | Cioanta |
| 2021/0310786 | A1 | 10/2021 | Zhang et al. |
| 2021/0330384 | A1 | 10/2021 | Cook et al. |
| 2021/0338258 | A1 | 11/2021 | Hawkins et al. |
| 2021/0353320 | A1 | 11/2021 | Dorfmüller et al. |
| 2021/0378743 | A1 | 12/2021 | Massimini et al. |
| 2022/0008129 | A1 | 1/2022 | Hancock et al. |
| 2022/0015785 | A1 | 1/2022 | Hakala et al. |
| 2022/0054194 | A1 | 2/2022 | Bacher et al. |
| 2022/0071692 | A1* | 3/2022 | Govari ............... A61B 18/1233 |
| 2022/0104875 | A1 | 4/2022 | Gleiman et al. |
| 2022/0125453 | A1 | 4/2022 | Nguyen |
| 2022/0152321 | A1 | 5/2022 | Haber et al. |
| 2022/0183708 | A1 | 6/2022 | Phan et al. |
| 2022/0240958 | A1 | 8/2022 | Nguyen et al. |
| 2022/0273324 | A1 | 9/2022 | Schultheis |
| 2022/0273916 | A1 | 9/2022 | Kawwas et al. |
| 2022/0280765 | A1 | 9/2022 | Tabiliran et al. |
| 2022/0287731 | A1 | 9/2022 | Tan et al. |
| 2022/0287732 | A1 | 9/2022 | Anderson et al. |
| 2022/0291442 | A1 | 9/2022 | De et al. |
| 2022/0313359 | A1 | 10/2022 | Schultheis et al. |
| 2022/0331012 | A1 | 10/2022 | Bumpus |
| 2022/0338890 | A1 | 10/2022 | Anderson et al. |
| 2022/0339428 | A1 | 10/2022 | Porterfield et al. |
| 2022/0354578 | A1 | 11/2022 | Cook et al. |
| 2023/0028890 | A1 | 1/2023 | Cioanta |
| 2023/0038663 | A1 | 2/2023 | Batchelder et al. |
| 2023/0040190 | A1 | 2/2023 | Batchelder et al. |
| 2023/0043475 | A1 | 2/2023 | Adams |
| 2023/0044926 | A1 | 2/2023 | Batchelder et al. |
| 2023/0064371 | A1 | 3/2023 | Cook et al. |
| 2023/0107690 | A1 | 4/2023 | Nguyen |
| 2023/0110647 | A1 | 4/2023 | Buscaglia et al. |
| 2023/0111554 | A1 | 4/2023 | Cioanta |
| 2023/0165598 | A1 | 6/2023 | Nguyen et al. |
| 2023/0293195 | A1 | 9/2023 | Lipowski et al. |
| 2023/0293196 | A1 | 9/2023 | Mantell |
| 2023/0293197 | A1 | 9/2023 | Nguyen et al. |
| 2023/0310054 | A1 | 10/2023 | Schultheis |
| 2023/0310073 | A1 | 10/2023 | Adams et al. |
| 2023/0329731 | A1 | 10/2023 | Hakala et al. |
| 2023/0363774 | A1 | 11/2023 | Cioanta et al. |
| 2023/0380849 | A1 | 11/2023 | Adams et al. |
| 2023/0404605 | A1 | 12/2023 | Vo |
| 2023/0414234 | A1 | 12/2023 | Anderson et al. |
| 2024/0016508 | A1 | 1/2024 | Kocur |
| 2024/0099734 | A1 | 3/2024 | Capelli et al. |
| 2024/0156476 | A1 | 5/2024 | Staab et al. |
| 2024/0156478 | A1 | 5/2024 | Ballard et al. |
| 2024/0188973 | A1 | 6/2024 | Cioanta et al. |
| 2024/0188975 | A1 | 6/2024 | Nguyen |
| 2024/0189030 | A1 | 6/2024 | Cook et al. |
| 2024/0189543 | A1 | 6/2024 | Salinas et al. |
| 2024/0206896 | A1 | 6/2024 | Ingersoll et al. |
| 2024/0206972 | A1 | 6/2024 | Sun et al. |
| 2024/0216062 | A1 | 7/2024 | Cook et al. |
| 2024/0252191 | A1 | 8/2024 | Cioanta et al. |
| 2024/0252192 | A1 | 8/2024 | Anderson et al. |
| 2024/0268842 | A1 | 8/2024 | Phan et al. |
| 2024/0277374 | A1 | 8/2024 | Varilla et al. |
| 2024/0277410 | A1 | 8/2024 | Cook |

(56) References Cited

U.S. PATENT DOCUMENTS

| | | | |
|---|---|---|---|
| 2024/0285295 | A1 | 8/2024 | Cioanta |
| 2024/0285296 | A1 | 8/2024 | Vo |
| 2024/0293282 | A1 | 9/2024 | Engles et al. |
| 2024/0299051 | A1 | 9/2024 | Sidhu et al. |
| 2024/0335206 | A1 | 10/2024 | Liu et al. |
| 2024/0350154 | A1 | 10/2024 | Nunes et al. |
| 2024/0366245 | A1 | 11/2024 | Schoenle |
| 2024/0423654 | A1 | 12/2024 | Ji et al. |
| 2025/0064471 | A1 | 2/2025 | Hasenberg et al. |
| 2025/0072967 | A1 | 3/2025 | Hasenberg et al. |
| 2025/0160862 | A1 | 5/2025 | Betelia et al. |
| 2025/0169835 | A1 | 5/2025 | Kerlo et al. |
| 2025/0176984 | A1 | 6/2025 | Hasenberg et al. |
| 2025/0268617 | A1 | 8/2025 | Rond et al. |
| 2025/0275782 | A1 | 9/2025 | Hasenberg et al. |
| 2025/0303109 | A1 | 10/2025 | Johnson et al. |

FOREIGN PATENT DOCUMENTS

| | | | |
|---|---|---|---|
| AU | 2007254353 | A1 | 11/2007 |
| AU | 2009257368 | A1 | 12/2009 |
| AU | 2009313507 | B2 | 11/2014 |
| AU | 2013284490 | A1 | 1/2015 |
| CA | 2104414 | A1 | 2/1995 |
| CA | 2613360 | A1 | 1/2007 |
| CA | 2652381 | A1 | 11/2007 |
| CA | 2727429 | A1 | 12/2009 |
| CA | 2779600 | A1 | 5/2010 |
| CN | 1204242 | A | 1/1999 |
| CN | 1269708 | A | 10/2000 |
| CN | 1161081 | C | 8/2004 |
| CN | 1942145 | A | 4/2007 |
| CN | 101043914 | A | 9/2007 |
| CN | 101495023 | A | 7/2009 |
| CN | 201629723 | U | 11/2010 |
| CN | 102057422 | A | 5/2011 |
| CN | 102271748 | A | 12/2011 |
| CN | 102355856 | A | 2/2012 |
| CN | 102765785 | A | 11/2012 |
| CN | 203564304 | U | 4/2014 |
| CN | 107633840 | A | 1/2018 |
| CN | 208694015 | U | 4/2019 |
| CN | 109965922 | A | 7/2019 |
| CN | 209548049 | U | 10/2019 |
| CN | 209996422 | U | 1/2020 |
| CN | 110811761 | A | 2/2020 |
| CN | 111067591 | A | 4/2020 |
| CN | 111184553 | A | 5/2020 |
| CN | 211094481 | U | 7/2020 |
| CN | 211094508 | U | 7/2020 |
| CN | 111388086 | B | 8/2020 |
| CN | 111568500 | A | 8/2020 |
| CN | 111568539 | A | 8/2020 |
| CN | 111969882 | A | 11/2020 |
| CN | 212491104 | U | 2/2021 |
| CN | 112516439 | A | 3/2021 |
| CN | 112618922 | A | 4/2021 |
| CN | 112674838 | A | 4/2021 |
| CN | 112754645 | A | 5/2021 |
| CN | 112842460 | A | 5/2021 |
| CN | 112869825 | A | 6/2021 |
| CN | 112869826 | A | 6/2021 |
| CN | 112869827 | A | 6/2021 |
| CN | 112932609 | A | 6/2021 |
| CN | 113117220 | A | 7/2021 |
| CN | 113244506 | A | 8/2021 |
| CN | 113288335 | A | 8/2021 |
| CN | 113289212 | A | 8/2021 |
| CN | 113289216 | A | 8/2021 |
| CN | 306761244 | S | 8/2021 |
| CN | 113332568 | A | 9/2021 |
| CN | 113332569 | A | 9/2021 |
| CN | 113332570 | A | 9/2021 |
| CN | 113349882 | A | 9/2021 |
| CN | 113349982 | A | 9/2021 |
| CN | 113398444 | A | 9/2021 |
| CN | 113440215 | A | 9/2021 |
| CN | 113558715 | A | 10/2021 |
| CN | 113598878 | A | 11/2021 |
| CN | 113633347 | A | 11/2021 |
| CN | 113648048 | A | 11/2021 |
| CN | 113730768 | A | 12/2021 |
| CN | 113842190 | A | 12/2021 |
| CN | 113855153 | A | 12/2021 |
| CN | 215067917 | U | 12/2021 |
| CN | 215228131 | U | 12/2021 |
| CN | 215384399 | U | 1/2022 |
| CN | 215384400 | U | 1/2022 |
| CN | 215386905 | U | 1/2022 |
| CN | 215458400 | U | 1/2022 |
| CN | 215458401 | U | 1/2022 |
| CN | 215505065 | U | 1/2022 |
| CN | 215537694 | U | 1/2022 |
| CN | 215584286 | U | 1/2022 |
| CN | 215606068 | U | 1/2022 |
| CN | 215651394 | U | 1/2022 |
| CN | 215653328 | U | 1/2022 |
| CN | 215688241 | U | 2/2022 |
| CN | 215739273 | U | 2/2022 |
| CN | 215900676 | U | 2/2022 |
| CN | 114098896 | A | 3/2022 |
| CN | 114098897 | A | 3/2022 |
| CN | 114098898 | A | 3/2022 |
| CN | 114209960 | A | 3/2022 |
| CN | 215960130 | U | 3/2022 |
| CN | 216061635 | U | 3/2022 |
| CN | 216495498 | U | 5/2022 |
| CN | 307361122 | S | 5/2022 |
| CN | 217040236 | U | 7/2022 |
| CN | 217066519 | U | 7/2022 |
| CN | 307436397 | S | 7/2022 |
| CN | 112971914 | B | 8/2022 |
| CN | 114831697 | A | 8/2022 |
| CN | 217138101 | U | 8/2022 |
| CN | 217162846 | U | 8/2022 |
| CN | 115051691 | A | 9/2022 |
| CN | 115137444 | A | 10/2022 |
| CN | 115149929 | A | 10/2022 |
| CN | 115153753 | A | 10/2022 |
| CN | 115154852 | A | 10/2022 |
| CN | 115192872 | A | 10/2022 |
| CN | 217611283 | U | 10/2022 |
| CN | 115252050 | A | 11/2022 |
| CN | 115389852 | A | 11/2022 |
| CN | 115463317 | A | 12/2022 |
| CN | 218391846 | U | 1/2023 |
| CN | 115737062 | A | 3/2023 |
| CN | 218899599 | U | 4/2023 |
| CN | 115944355 | B | 6/2023 |
| CN | 117462207 | A | 1/2024 |
| DE | 2635635 | A1 | 2/1978 |
| DE | 3038445 | A1 | 5/1982 |
| DE | 3536073 | A1 | 4/1987 |
| DE | 3900433 | A1 | 7/1990 |
| DE | 3930600 | A1 | 4/1991 |
| DE | 4005743 | A1 | 8/1991 |
| DE | 4007295 | A1 | 9/1991 |
| DE | 4012642 | A1 | 10/1991 |
| DE | 4120259 | A1 | 12/1992 |
| DE | 29724174 | U1 | 4/2000 |
| DE | 10010467 | A1 | 9/2001 |
| DE | 102004053549 | A1 | 5/2006 |
| DE | 202006014285 | U1 | 12/2006 |
| DE | 102006002412 | A1 | 7/2007 |
| EP | 0249338 | A2 | 12/1987 |
| EP | 0311295 | A2 | 4/1989 |
| EP | 0313836 | A2 | 5/1989 |
| EP | 0351240 | A2 | 1/1990 |
| EP | 0382392 | A1 | 8/1990 |
| EP | 0442199 | A2 | 8/1991 |
| EP | 0547146 | A1 | 6/1993 |
| EP | 0558297 | A2 | 9/1993 |
| EP | 0571306 | A1 | 11/1993 |
| EP | 0647435 | A1 | 4/1995 |

(56) References Cited

FOREIGN PATENT DOCUMENTS

| | | | |
|---|---|---|---|
| EP | 0704226 | A1 | 4/1996 |
| EP | 0623360 | B1 | 3/1999 |
| EP | 1898775 | A2 | 3/2008 |
| EP | 2023796 | A2 | 2/2009 |
| EP | 2043501 | A2 | 4/2009 |
| EP | 2046227 | A2 | 4/2009 |
| EP | 1009303 | B1 | 6/2009 |
| EP | 2120736 | A1 | 11/2009 |
| EP | 2253884 | A1 | 11/2010 |
| EP | 2300091 | A2 | 3/2011 |
| EP | 2362798 | A2 | 9/2011 |
| EP | 2032201 | B1 | 4/2013 |
| EP | 2866689 | A1 | 5/2015 |
| EP | 2879607 | A1 | 6/2015 |
| EP | 3021473 | A1 | 5/2016 |
| EP | 3487414 | A2 | 5/2019 |
| EP | 3641672 | A1 | 4/2020 |
| EP | 4110213 | A1 | 1/2023 |
| EP | 4199849 | A1 | 6/2023 |
| EP | 4387540 | A1 | 6/2024 |
| EP | 4391946 | A1 | 7/2024 |
| EP | 4406496 | A1 | 7/2024 |
| EP | 4423863 | A1 | 9/2024 |
| EP | 4431032 | A1 | 9/2024 |
| FR | 2412301 | A1 | 7/1979 |
| FR | 2593382 | A1 | 7/1987 |
| FR | 2738381 | A1 | 3/1997 |
| JP | 58-032755 | A | 2/1983 |
| JP | 60-191353 | U | 12/1985 |
| JP | 61-146251 | A | 7/1986 |
| JP | 62-009921 | U | 1/1987 |
| JP | 62-060547 | A | 3/1987 |
| JP | 62-099210 | U | 6/1987 |
| JP | 62-275446 | A | 11/1987 |
| JP | 03-063059 | A | 3/1991 |
| JP | 06-070984 | A | 3/1994 |
| JP | 06-125915 | A | 5/1994 |
| JP | 07-047135 | A | 2/1995 |
| JP | 08-089511 | A | 4/1996 |
| JP | 10-099444 | A | 4/1998 |
| JP | 10-314177 | A | 12/1998 |
| JP | 10-513379 | A | 12/1998 |
| JP | 2002-538932 | A | 11/2002 |
| JP | 2003-102850 | A | 4/2003 |
| JP | 2004-081374 | A | 3/2004 |
| JP | 2004-223080 | A | 8/2004 |
| JP | 2004-357792 | A | 12/2004 |
| JP | 2005-501597 | A | 1/2005 |
| JP | 2005-095410 | A | 4/2005 |
| JP | 2005-515825 | A | 6/2005 |
| JP | 2006-516465 | A | 7/2006 |
| JP | 2007-054480 | A | 3/2007 |
| JP | 2007-289707 | A | 11/2007 |
| JP | 2007-532182 | A | 11/2007 |
| JP | 2008-506447 | A | 3/2008 |
| JP | 4072580 | B2 | 4/2008 |
| JP | 2009-537222 | A | 10/2009 |
| JP | 4491149 | B2 | 6/2010 |
| JP | 2011-513694 | A | 4/2011 |
| JP | 2011-520248 | A | 7/2011 |
| JP | 2011-524203 | A | 9/2011 |
| JP | 2011-528963 | A | 12/2011 |
| JP | 2012-505050 | A | 3/2012 |
| JP | 2012-508042 | A | 4/2012 |
| JP | 2014-208305 | A | 11/2014 |
| JP | 5636363 | B2 | 12/2014 |
| JP | 2015-525657 | A | 9/2015 |
| JP | 2015-528327 | A | 9/2015 |
| JP | 6029828 | B2 | 11/2016 |
| JP | 6081510 | B2 | 2/2017 |
| WO | 89/11307 | A1 | 11/1989 |
| WO | 91/10228 | A1 | 7/1991 |
| WO | 91/10403 | A1 | 7/1991 |
| WO | 92/03975 | A1 | 3/1992 |
| WO | 95/10232 | A1 | 4/1995 |
| WO | 96/24297 | A1 | 8/1996 |
| WO | 97/21460 | A1 | 6/1997 |
| WO | 98/33171 | A2 | 7/1998 |
| WO | 99/00060 | A1 | 1/1999 |
| WO | 99/02096 | A1 | 1/1999 |
| WO | 99/21611 | A1 | 5/1999 |
| WO | 00/33913 | A2 | 6/2000 |
| WO | 00/50115 | A2 | 8/2000 |
| WO | 00/51511 | A1 | 9/2000 |
| WO | 00/56237 | A2 | 9/2000 |
| WO | 01/24712 | A1 | 4/2001 |
| WO | 03/51450 | A1 | 6/2003 |
| WO | 03/86236 | A2 | 10/2003 |
| WO | 03/86525 | A1 | 10/2003 |
| WO | 2004/069072 | A2 | 8/2004 |
| WO | 2005/053532 | A1 | 6/2005 |
| WO | 2005/099594 | A1 | 10/2005 |
| WO | 2005/102199 | A1 | 11/2005 |
| WO | 2006/006169 | A2 | 1/2006 |
| WO | 2006/060492 | A2 | 6/2006 |
| WO | 2006/127158 | A2 | 11/2006 |
| WO | 2007/002079 | A2 | 1/2007 |
| WO | 2007/022055 | A1 | 2/2007 |
| WO | 2007/052341 | A1 | 5/2007 |
| WO | 2007/053967 | A1 | 5/2007 |
| WO | 2007/086965 | A2 | 8/2007 |
| WO | 2007/088546 | A2 | 8/2007 |
| WO | 2007/136599 | A2 | 11/2007 |
| WO | 2007/149905 | A2 | 12/2007 |
| WO | 2008/014425 | A2 | 1/2008 |
| WO | 2008/017080 | A2 | 2/2008 |
| WO | 2008/097833 | A1 | 8/2008 |
| WO | 2009/121017 | A1 | 10/2009 |
| WO | 2009/126544 | A1 | 10/2009 |
| WO | 2009/128061 | A2 | 10/2009 |
| WO | 2009/136268 | A2 | 11/2009 |
| WO | 2009/152352 | A2 | 12/2009 |
| WO | 2010/014515 | A2 | 2/2010 |
| WO | 2010/054048 | A2 | 5/2010 |
| WO | 2011/006017 | A1 | 1/2011 |
| WO | 2011/094111 | A2 | 8/2011 |
| WO | 2011/143468 | A3 | 3/2012 |
| WO | 2012/025833 | A2 | 3/2012 |
| WO | 2012/064404 | A1 | 5/2012 |
| WO | 2012/106259 | A2 | 8/2012 |
| WO | 2013/059735 | A1 | 4/2013 |
| WO | 2013/070750 | A1 | 5/2013 |
| WO | 2013/169807 | A1 | 11/2013 |
| WO | 2014/004887 | A1 | 1/2014 |
| WO | 2014/025397 | A1 | 2/2014 |
| WO | 2014/025620 | A1 | 2/2014 |
| WO | 2014/025981 | A1 | 2/2014 |
| WO | 2014/028885 | A1 | 2/2014 |
| WO | 2014/043400 | A1 | 3/2014 |
| WO | 2015/017499 | A1 | 2/2015 |
| WO | 2015/167360 | A1 | 11/2015 |
| WO | 2016/130713 | A1 | 8/2016 |
| WO | 2018/200865 | A1 | 11/2018 |
| WO | 2019/099218 | A1 | 5/2019 |
| WO | 2019/174625 | A1 | 9/2019 |
| WO | 2020/048274 | A1 | 3/2020 |
| WO | 2020/192146 | A1 | 10/2020 |
| WO | 2021/022849 | A1 | 2/2021 |
| WO | 2021/025624 | A1 | 2/2021 |
| WO | 2021/122491 | A1 | 6/2021 |
| WO | 2022/055784 | A1 | 3/2022 |
| WO | 2022/127506 | A1 | 6/2022 |
| WO | 2022/127507 | A1 | 6/2022 |
| WO | 2022/127509 | A1 | 6/2022 |
| WO | 2022/166883 | A1 | 8/2022 |
| WO | 2022/183075 | A1 | 9/2022 |
| WO | 2022/186783 | A1 | 9/2022 |
| WO | 2022/217917 | A1 | 10/2022 |
| WO | 2023/015047 | A1 | 2/2023 |
| WO | 2023/015295 | A1 | 2/2023 |
| WO | 2023/029191 | A1 | 3/2023 |
| WO | 2023/083084 | A1 | 5/2023 |
| WO | 2024/049814 | A1 | 3/2024 |
| WO | 2024/081361 | A1 | 4/2024 |

(56) References Cited

FOREIGN PATENT DOCUMENTS

| | | |
|---|---|---|
| WO | 2024/102896 A2 | 5/2024 |
| WO | 2024/107418 A1 | 5/2024 |
| WO | 2024/107470 A1 | 5/2024 |
| WO | 2024/138037 A2 | 6/2024 |
| WO | 2024/138212 A1 | 6/2024 |
| WO | 2024/206827 A2 | 10/2024 |
| WO | 2024/216050 A2 | 10/2024 |
| WO | 2025/054289 A1 | 3/2025 |

OTHER PUBLICATIONS

Judgment, Final Written Decision Determining All Challenged Claims Unpatentable Denying Petitioner's Motion to Exclude Denying Patent Owner's Motion to Exclude, 35 U.S.C. Section 318(a); 37 C.F.R. Section 42.64, Paper 75, IPR2019-00409, in U.S. Pat. No. 8,728,091 B2, dated Jul. 8, 2020.

Judgment, Final Written Decision Determining All Challenged Claims Unpatentable Denying Petitioner's Motion to Exclude Denying Petitioner's Motion to Exclude Denying Patent Owner's Motion to Exclude 35 U.S.C. Section 318(a), 37 C.F.R. Section 42.64, Paper 70, IPR2019-00408, in U.S. Pat. No. 9,642,673 B2, Entered Jul. 20, 2020.

Judgment, Final Written Decision Determining Some Challenged Claims Unpatentable Denying Petitioner's Motion to Exclude 35 U.S.C. Section 318(a), 37 C.F.R. Section 42.64, Paper 75, IPR2019-00405, in U.S. Pat. No. 8,956,371 B2, dated Jul. 8, 2020.

Kaltenbach, "The long wire technique—a new technique for steerable balloon catheter dilatation of coronary artery stenoses", European Heart Journal, vol. 5, 1984, pp. 1004-1009.

Kereiakes et al., "Principles of Intravascular Lithotripsy for Calcific Plaque Modification", JACC: Cardiovascular Interventions, vol. 14, No. 12, Jun. 28, 2021, pp. 1275-1292.

Kodama et al. "Innovative technology for tissue disruption by explosive-induced shock waves", Ultrasound in Medicine & Biology vol. 24, No. 9, 1998, pp. 1459-1460.

Lee et al., "Intravascular Lithotripsy for Calcified Left Main Artery Disease", Journal of the Society for Cardiovascular Angiography and Interventions, vol. 2, 2023, pp. 1-6.

Lee. et al., "Intravascular steerable guidewire for fiberoptic laser-heated metal cautery cap in dissolution of human atherosclerotic coronary disease," American Heart Journal, vol. 110, Issue 6, 1985, pp. 1304-1306.

Levin. et al., "Percutaneous Transluminal Coronary Angioplasty with an Over-the-Wire System," Radiology, vol. 155, Issue 2, 1985, pp. 323-326.

Litvack. et al., "Percutaneous excimer laser coronary angioplasty: results in the first consecutive 3,000 patients," Journal of the American College of Cardiology, vol. 23, Issue 2, 1994, pp. 323-329.

Lumsden. et al., "Endovascular Therapy Principles of Peripheral Interventions," Blackwell Futura, 2006, 310 pages.

Mariani., "Combined Electrohydraulic and Holmium:Yag Laser Ureteroscopic Nephrolithotripsy for 20 to 40 MM Renal Calculi," The Journal of urology, vol. 172, Issue 1, 2004, pp. 170-174.

McAuley. et al., "Advances in guidewire technology," The American Journal of Cardiology, vol. 53, Issue 12, 1984, pp. C94-C96.

Miller et al., "Electrohydraulic Nephrolithotripsy: a Preferable Alternative to Ultrasound?", British Journal of Urology, vol. 56, 1984, pp. 589-593.

MILLER., "Endoscopic application of shock wave technology for the destruction of renal calculi" World Journal of Urology, vol. 3, 1985, pp. 36-40.

Mishra, A., et al., "RevaTen platelet-rich plasma improves cardiac function after myocardial injury.", Cardiovascular Revascularization Medicine, vol. 12, No. 3, 2011, pp. 158-163.

Mohiuddin et al., "General principles of endovascular therapy" in Endovascular Therapy: Principles of Peripheral Interventions, pp. 1-19 (2006).

Müller-Leisse. et al., "Effectiveness and safety of ultrasonic atherosclerotic plaque ablation: In vitro investigation," Cardiovascular and interventional radiology, vol. 16, 1993, pp. 303-307.

Neuzil, P., et al., "TCT-61 Optimized external focused ultrasound for renal sympathetic denervation-Wave II trial.", Journal of the American College of Cardiology, vol. 62, No. 18S1, 2013.

Nimgaonkar, A., et al., "Gastroenterology and biodesign: contributing to the future of our specialty.", Gastroenterology, vol. 144, No. 2, 2013, pp. 258-262.

Northgate Technologies, Northgate Autolith pulse generator in 2007, at the Wayback Machine, https://web.archive.org/web/20070704002225/http://www.northgate-tech.com:80/Products/stonemanagement.asp.

Ormiston, J. A., et al., "TCT-412 non-invasive renal denervation using externally delivered focused ultrasound: early experience using Doppler based imaging tracking and targeting for treatment.", Journal of the American College of Cardiology, vol. 64, No. 11, 2014.

Park. et al., "Percutaneous Nephrolithotomy Technical Aspects," The Practical Guide to Medical and Surgical Management, 2007, pp. 621-638.

Partial File History for U.S. Appl. No. 63/154,603, filed Feb. 26, 2021.

Partial File History for U.S. Appl. No. 63/176,156, filed Apr. 16, 2021.

Partial File History for U.S. Appl. No. 63/193,469, filed May 26, 2021.

Partial File History for U.S. Appl. No. 63/169,091, filed Mar. 31, 2021.

Payne., "Charles Theodore Dotter: the father of intervention," Texas Heart Institute Journal, vol. 28, Issue 1, 2001, pp. 28-38.

Petition for Inter Partes Review of U.S. Pat. No. 8,728,091, filed Dec. 7, 2018.

Petition for Inter Partes Review of U.S. Pat. No. 8,956,371 Under 35 U.S.C. Section 312 and 37 C.F.R. Section 42.104, filed Dec. 7, 2018.

Petition for Inter Partes Review of U.S. Pat. No. 9,642,673 Under 35 U.S.C. Section 312 and 37 C.F.R. Section 42.104, filed Dec. 7, 2018.

Rassweiler et al. "Efficacy of in situ Extracorporeal Shock Wave Lithotripsy for Upper Ureteral Calculi" Uropean Urology, vol. 12 No. 6, 1986, pp. 377-386.

Rosenschein. et al., "Experimental Ultrasonic Angioplasty: Disruption of Atherosclerotic Plaques and Thrombi in Vitro and Arterial Recanalization in Vivo," Journal of the American College of Cardiology, vol. 15, Issue 3, 1990, pp. 711-717.

Sasportas, L. S., et al., "Cost-effectiveness landscape analysis of treatments addressing xerostomia in patients receiving head and neck radiation therapy.", Oral surgery, oral medicine, oral pathology and oral radiology, vol. 116, No. 1, 2013, pp. e37-e51.

Seshiah et al., "Novel Lithotripsy-Assisted Transcatheter Aortic Valve Replacement May Reduce Risk of Aortic Root Rupture", Journal of the Society for Cardiovascular Angiography and Interventions, vol. 2, 2023, pp. 1-4.

Siegel et al., "Ultrasonic plaque ablation. A new method for recanalization of partially or totally occluded arteries", Circulation, vol. 78, No. 6, Dec. 1988, pp. 1443-1448.

Sista, A. K., et al., "Applying a structured innovation process to interventional radiology: a single-center experience.", Journal of Vascular and Interventional Radiology, vol. 23, No. 4, 2012, 488-494.

Stoller et al., "Urinary Stone Disease: The Practical Guide to Medical and Surgical Management", 2007, 685 Pages.

Svendsen et al., "Conductance sizing balloon for measurement of peripheral artery minimal stent area," Journal of Vascular Surgery, vol. 60, No. 3, Sep. 2014, pp. 759-766.

Touya, G., et al., "Development of subsonic electrical discharges in water and measurements of the associated pressure waves", Journal of Physics D: Applied Physics, 39 (2006), pp. 5236-5244.

Welch et al. "Laser Physics and Laser-Tissue Interaction", The Texas Heart Institute Journal, vol. 16 No. 3, 1989, pp. 141-149.

(56) References Cited

OTHER PUBLICATIONS

Willmann, J. K., et al., "Imaging gene expression in human mesenchymal stem cells: from small to large animals.", Radiology, vol. 252, No. 1, 2009, pp. 117-127.
Worley. et al., "Electrohydraulic Shock Wave Decalcification of Stenotic Aortic Valves : Postmortem and Intraoperative Studies" Journal of the American College of Cardiology, vol. 12, Issue 2, 1988, pp. 458-462.
Yock, P. G., et al., "Teaching biomedical technology innovation as a discipline.", Science translational medicine, vol. 3, No. 92, 2011, 5 pages.
Zhong et al., "Transient Oscillation of Cavitation Bubbles Near Stone Surface During Electrohydraulic Lithotripsy," Journal of Endourology, vol. 11, No. 1, pp. 55-61 (Feb. 1997).
Ali, Z. "The Sound Science Behind Shockwave IVL's Mechanism of Action", Transcatheter Cardiovascular Therapeutics, Peripheral IVL Speaker Deck, believed to be presented Oct. 29, 2024.
Baim., "Grossman's Cardiac Catheterization, Angiography, and Intervention," Seventh Edition, 2005, 6 pages.
Baim., "Percutaneous Balloon Angioplasty and General Coronary Intervention," Chapter 22, 2005, pp. 433-466.
Bertrand et al., "Percutaneous Transluminal Coronary Rotary Ablation with Rotablator (European Experience)", The American Journal of Cardiology, vol. 69, Feb. 15, 1992, pp. 470-474.
Brinton, T. D., et al., "Abstract 12272: Ultrasound Mediated Renal Sympathetic Denervation", Circulation, vol. 124, No. 21, Nov. 22, 2011.
Brinton, T. J., et al., "Current use of imaging in cardiac stem cell clinical trials.", Current Cardiovascular Imaging Reports, vol. 2, No. 1, 2009, pp. 1-2.
Brinton, T. J., et al., "Outcomes from a postgraduate biomedical technology innovation training program: the first 12 years of Stanford Biodesign.", Annals of biomedical engineering, vol. 41, 2013, pp. 1803-1810.
Chan et al., "A Perspective on Laser Lithotripsy: The Fragmentation Processes", Journal of Endourology, vol. 15, No. 3, Apr. 2001, pp. 257-273.
Choi et al., "Low Power Ultrasound Delivered Through a PTCA-Like Guidewire: Preclinical Feasibility and Safety of a Novel Technology for Intracoronary Thrombolysis," Journal of Interventional Cardiology, vol. 19, Issue 1, 2006, pp. 87-92.
Cleveland, R.O.; McAteer, J.A. "Physics of Shock-Wave Lithotripsy". In Smith's Textbook of Endourology; Wiley: Hoboken, NJ, USA, 2012; pp. 317-332.
Compare Materials, from MatWeb, retrieved from https://www.matweb.com, accessed on Feb. 26, 2024, 5 pp.
Dash R., et al., "Abstract 12435: Detection of Injured Border Zone Myocardium Using Manganese-Enhanced and Delayed-Enhanced MRI in a Pig Ischemia-Reperfusion Model", Circulation, vol. 122, Supp. 21, Nov. 23, 2010.
Dash, R., et al., "Dual manganese-enhanced and delayed gadolinium-enhanced MRI detects myocardial border zone injury in a pig ischemia-reperfusion model.", Circulation: Cardiovascular Imaging, vol. 4, No. 5, 2011, pp. 574-582.
Dervan et al., "Transluminal angioplasty of occluded coronary arteries: use of a movable guide wire system", Circulation 68, No. 4, 1983, pp. 776-784.
Ernst et al., "Ability of High-Intensity Ultrasound to Ablate Human Atherosclerotic Plaques and Minimize Debris Size," The American journal of cardiology, vol. 68, Issue 2, 1991, pp. 242-246.
Extended European Search Report dated Jul. 22, 2022 in European Patent Application No. 22168972.2.
Extended European Search Report dated Jul. 25, 2022 in European Patent Application No. 22167795.8.
Extended European Search Report dated Jul. 25, 2022 in European Patent Application No. 22167806.3.
Extended European Search Report dated Jul. 15, 2022 in European Patent Application No. 22167569.7.
Extended European Search Report dated Jul. 19, 2022 in European Patent Application No. 22168990.4.
Extended European Search Report dated Jul. 22, 2022 in European Patent Application No. 22169681.8.
Extended European Search Report dated Jul. 25, 2022 in European Patent Application No. 22167815.4.
Extended European Search Report dated Jul. 25, 2022 in European Patent Application No. 22168984.7.
Fuh, E., et al., "Bone marrow stem cells for the treatment of ischemic heart disease: a clinical trial review.", Journal of Cardiovascular Translational Research, vol. 2, 2009, pp. 202-218.
Gavin et al., "An acoustic fluid-structure simulation of a therapeutic ultrasound wire waveguide apparatus," 11th International Conference on Computational Biogengineering, 2005, 14 pages.
Gerdesmeyer et al., "Physical and technical basics of extracorporeal shock wave therapy (ESWT)," The orthopedist, vol. 7, Issue 31, 2002, pp. 610-617. (English abstract).
Gravenstein D., "Extracorporeal shock wave lithotripsy and percutaneous nephrolithotomy", Anesthesia and Renal Considerations, vol. 18, No. 4, Dec. 2000, pp. 953-971.
Grech., "Percutaneous coronary intervention. I: History and development," Bmj, vol. 326, Issue 7398, 2003, pp. 1080-1082.
Gunn et al., "New developments in percutaneous coronary intervention," BMJ, vol. 327, Issue 7407, 2003, pp. 150-153.
Harston et al., "Safety and Success of the Beginning Percutaneous Transluminal Coronary Angioplasty Program Using the Steerable Guidewire System", Coronary Angioplasty With Steerable Guidewire, vol. 57, Apr. 1, 1986, pp. 717-720.
Hong, S. J., et al., "Intracoronary and retrograde coronary venous myocardial delivery of adipose-derived stem cells in swine infarction lead to transient myocardial trapping with predominant pulmonary redistribution.", Catheterization and Cardiovascular Interventions, vol. 83, No. 1, 2014, pp. E17-E25.
International Application No. PCT/US2024/022239, filed Mar. 29, 2014.
International Application No. PCT/US2024/024296, filed Apr. 12, 2024.
International Application No. PCT/US2024/025362, filed Apr. 19, 2024.
International Application No. PCT/US2024/025369, filed Apr. 19, 2024.
International Preliminary Report on Patentability for dated Aug. 11, 2022 for PCT Application Serial No. PCT/US2022/071341, Filed Mar. 25, 2022.
International Preliminary Report on Patentability mailed Feb. 6, 2024 for PCT Application Serial No. PCT/US2022/074607, Filed Aug. 5, 2022.
International Search Report and Written Opinion issued in PCT application No. PCT/US2022/71341, dated Aug. 11, 2022.
International Search Report and Written Opinion issued in PCT/US2021/71726, dated Feb. 7, 2022.
International Search Report and Written Opinion of International Application No. PCT/US2023/85515, mailed Jun. 13, 2024, 10 pp.
International Search Report and Written Opinion of International Application No. PCT/US2024/022239, mailed Jul. 26, 2024, 8 pp.
International Search Report and Written Opinion of International Application No. PCT/US2024/024296, mailed Aug. 21, 2024, 14 pp.
International Search Report and Written Opinion of International Application No. PCT/US2024/025362, mailed Jul. 23, 2024, 12 pp.
International Search Report and Written Opinion of International Application No. PCT/US2024/025369, mailed Jul. 23, 2024, 11 pp.
International Search Report and Written Opinion of International Application No.PCT/US2023/035025, mailed Jan. 18, 2024, 11 pp.
International Search Report and Written Opinion of International Application No.PCT/US2023/037234, mailed Mar. 12, 2024, 8 pp.
International Search Report and Written Opinion received for International Patent Application No. PCT/US2022/078216, mailed on Feb. 1, 2023, 6 pages.
International Search Report and Written Opinion, mailed Apr. 12, 2024 for PCT Application Serial No. PCT/US2023/079209, filed Nov. 9, 2023.
International Search Report and Written Opinion, mailed Feb. 22, 2024, for PCT Application Serial No. PCT/US23/73648, filed Sep. 7, 2023.

(56) References Cited

OTHER PUBLICATIONS

International Search Report and Written Opinion, mailed May 28, 2024, for PCT Application Serial No. PCT/US23/085868, filed Dec. 23, 2024.
Begun, Frank P., "Modes of Intracorporeal Lithotripsy: Ultrasound Versus Electrohydraulic Lithotripsy Versus Laser Lithotripsy", Seminars in Urology, vol. 12, No. 1, Feb. 1994, pp. 39-50.
Grocela et al., "Intracorporeal Lithotripsy: Instrumentation and Development", Urologic Clinics of North America, vol. 24, No. 1, Feb. 1997, pp. 13-23.
Papatsoris et al., "Update on Intracorporeal Laser Lithotripsy", Minerva Medica, vol. 104, No. 1, 2013, pp. 55-60.
Scotland et al., "Stone Technology: Intracorporeal Lithotripters", World Journal of Urology, vol. 35, 2017, pp. 1347-1351.
Shockwave C2. "Coronaw IVL System Step-by-Step Setup", Shockwave Medical, Inc., Exhibit 2163, Provided as part of case IPR2019-00405, U.S. Pat. No. 8,956,371.
Shockwave Medical, Investor Presentation, Slides 7-23 (Nov. 2022).
Vorreuther et al., "Impact of Shock Wave Pattern and Cavitation Bubble Size on Tissue Damage During Ureteroscopic Electrohydraulic Lithotripsy", The Journal of Urology, vol. 153, Mar. 1995, pp. 849-853.
Zheng et al., "Intracorporeal Lithotripsy: Update on Technology", Urologic Clinics of North America, vol. 27, No. 2, May 2000, pp. 301-313.
Basavarajaiah, S. et al., "To evaluate the impact of dose dependency on calcium fractures from the shockwave balloon in calcified lesions" [PowerPoint Presentation], Transcatheter Cardiovascular Therapeutics Conference, San Francisco, CA, United States, Oct. 25-28, 2025.
Briggs, C., et al., "The New Shockwave L6 Peripheral Intravascular Lithotripsy (IVL) Catheter", Endovascular Today, May 2023.
Corl, J. D., et al., "First Human Use of Shockwave L6 Intravascular Lithotripsy Catheter in Severely Calcified Large Vessel Stenoses", Journal of the Society for Cardiovascular Angiography & Interventions, vol. 2, Issue 4, May 2023.
Davies, R., "You Asked; Shockwave C2 Aero Delivered: Shockwave's Next Coronary Catheter" [PowerPoint Presentation], Transcatheter Cardiovascular Therapeutics Conference, San Francisco, CA, United States, Oct. 25-28, 2025.
Lingeman, J. E., et al., "Shock wave lithotripsy: Advances in technology and technique." Nature Reviews Urology, vol. 6, Dec. 2009, pp. 660-670.
Llewellyn-Jones, F., "The Mechanism of Electrode Erosion in Electrical Discharges: Physical Basis of the Low Erosion Rate of the Platinum Metals", Platinum Metals Review, vol. 7, Issue 2, Jan. 1963, pp. 58-65.
Loske, A. M. (2007). Shock Wave Physics for Urologists. Centro de Física Aplicada y Tecnología Avanzada, National Autonomous University of Mexico. ISBN 978-970-32-4377-8.
Owens, C. A., "Ultrasound-Enhanced Thrombolysis: EKOS EndoWave Infusion Catheter System". Seminars in Interventional Radiology, vol. 25, No. 1, Mar. 2025, pp. 37-41.
Salgaonkar, V. A. & Diederich, C. J., "Catheter-based ultrasound technology for image-guided thermal therapy: Current technology and applications." International Journal of Hyperthermia, vol. 31, No. 2, Mar. 2015, pp. 203-215.
Shockwave Medical Inc., "Shockwave Intravascular Lithotripsy (IVL) System with the Shockwave L6 Peripheral Intravascular Lithotripsy (IVL) Catheter—Instructions for use (IFU)", PN 67214-A, 2022, 6 pages.
Shockwave Medical Inc., "Shockwave Intravascular Lithotripsy (IVL) System with the Shockwave L6 Peripheral Intravascular Lithotripsy (IVL) Catheter—Instructions for use (IFU)", PN 69653-B, 2024, 5 pages.
Sokolov, D. L., et al., "Dual Pulse Lithotripsy Points Toward Faster, Safer Treatment for Kidney Stones", Dec. 2002, retrieved from https://acoustics.org/pressroom/httpdocs/144th/Bailey.htm, accessed on Dec. 9, 2025, 3 pages.
Sokolov, D. L., et al., "Dual-pulse lithotripter accelerates stone comminution and reduces cell injury in vitro", The Journal of the Acoustical Society of America. Vol. 112, Issue 5, Nov. 2002, p. 2290. Retrieved from https://pubs.aip.org/asa/jasa/article/112/5_Supplement/2290/541200/Dual-pulse-lithotripter-accelerates-stone, accessed Dec. 10, 2025.
Sokolov, D. L., et al., "Dual-pulse lithotripter accelerates stone fragmentation and reduces cell lysis in vitro", Ultrasound in Medicine & Biology, vol. 29, Issue 7, Jul. 2003, pp. 1045-1052.
Spratt, J.C., "Shockwave IVL Mechanism of Action" [PowerPoint Presentation], Transcatheter Cardiovascular Therapeutics Conference, San Francisco, CA, United States, Oct. 25-28, 2025.
U.S. Appl. No. 61/289,125 filed Dec. 22, 2009.
Vorreuther, R., et al., "Impact of voltage and capacity on the electrical and acoustic output of intracorporeal electrohydraulic lithotripsy", Urological Research, vol. 20, Sep. 1992, pp. 355-359.
Wang, Q., et al., "Effectiveness and safety of a novel IVL system for severe coronary calcification: The CALCI-CRACK trial", Canadian Journal of Cardiology, vol. 40, Issue 9, Sep. 2024, pp. 1657-1667.
Galougahi, K.K., et al., "Intravascular Lithotripsy in Cardiovascular Interventions", American College of Cardiology, Jul. 2020.
Li, G., et al., "Evaluation of an Experimental Electrohydraulic Discharge Device for Extracorporeal Shock Wave Lithotripsy: Pressure Field of Sparker Array", The Journal of the Acoustical Society of America, vol. 142, Issue 5, Nov. 2017, pp. 3147-3153.
Shockwave Medical, Inc., "Shockwave Intravascular Lithotripsy (IVL) System with the Shockwave C2 Coronary Intravascular Lithotripsy (IVL) Catheter", Feb. 2021, pp. 1-6.

* cited by examiner

CONTROL OF IVL SYSTEMS, DEVICES AND METHODS THEREOF

CROSS-REFERENCE TO RELATED APPLICATIONS

This application is a continuation of application Ser. No. 18/290,173, filed Nov. 10, 2023 and titled CONTROL OF IVL SYSTEMS, DEVICES AND METHODS THEREOF and also claims benefit of provisional application No. 63/424,573, filed Nov. 11, 2022 and titled DEVICES, SYSTEMS, AND METHODS OF INTRAVASCULAR LITHOTRIPSY and provisional application No. 63/580,547, filed Sep. 5, 2023 and titled DEVICES, SYSTEMS AND METHODS OF INTRAVASCULAR LITHOTRIPSY, the entire content of each of which is incorporated herein by reference.

STATEMENT REGARDING FEDERALLY SPONSORED RESEARCH OR DEVELOPMENT

None

BACKGROUND OF THE INVENTION

Field of the Invention

The present disclosure relates to devices, systems, and methods for breaking up calcified lesions in an anatomical conduit. More specifically, the present disclosure relates to control of devices, systems, and methods for applying electrical arc spaced-apart electrodes disposed within a fluid-filled member to creating flow and pressure waves.

Description of the Related Art

A variety of techniques and instruments have been developed for use in the removal or repair of tissue in arteries and similar body passageways, including removal and/or cracking of calcified lesions within the passageway and/or formed within the wall defining the passageway. A frequent objective of such techniques and instruments is the removal of atherosclerotic plaque in a patient's arteries. Atherosclerosis is characterized by the buildup of fatty deposits (atheromas) in the intimal layer (i.e., under the endothelium) of a patient's blood vessels. Very often over time what initially is deposited as relatively soft, cholesterol-rich atheromatous material hardens into a calcified atherosclerotic plaque, often within the vessel wall. Such atheromas restrict the flow of blood, cause the vessel to be less compliant than normal, and therefore often are referred to as stenotic lesions or stenoses, the blocking material being referred to as stenotic material. If left untreated, such stenoses can cause angina, hypertension, myocardial infarction, strokes and the like.

Angioplasty, or balloon angioplasty, is an endovascular procedure to treat by widening narrowed or obstructed arteries or veins, typically to treat arterial atherosclerosis. A collapsed balloon is typically passed through a pre-positioned catheter and over a guide wire into the narrowed occlusion and then inflated to a fixed pressure. The balloon forces expansion of the occlusion within the vessel and the surrounding muscular wall until the occlusion yields from the radial force applied by the expanding balloon, opening up the blood vessel with a lumen inner diameter that is similar to the native vessel in the occlusion area and, thereby, improving blood flow.

The angioplasty procedure presents some risks and complications, including but not limited to: arterial rupture or other damage to the vessel wall tissue from over-inflation of the balloon catheter, the use of an inappropriately large or stiff balloon, the presence of a calcified target vessel; and/or hematoma or pseudoaneurysm formation at the access site. Generally, the pressures produced by traditional balloon angioplasty systems is in the range of 10-15 atm, but pressures may at times be higher. As described above, the primary problem with known angioplasty systems and methods is that the occlusion yields over a relatively short time period at high stress and strain rate, often resulting in damage or dissection of the conduit, e.g., blood vessel, wall tissue.

Traditional systems may apply coarse system controls. For example, ceasing power supply from the power source may be applied as a primary means to regulate the amount of energy applied to a therapy site. Such an approach is taught by U.S. Pat. No. 8,728,091 wherein current is monitored during application of voltage by a pulse generator. When the current exceeds a predetermined threshold magnitude, the voltage is turned off at the pulse generator. As discussed in additional detail herein, a refined approach to power characteristic control can assist in more effective and more consistent therapy. For example, improved durability, higher frequency and substantially equivalent pressure output, over a longer number of voltage pulses than previously possible, are provided using embodiments of the present disclosure.

Various embodiments of the present disclosure can address these issues, among others, discussed above.

BRIEF DESCRIPTION OF THE SEVERAL VIEWS OF THE DRAWINGS

These drawings are exemplary illustrations of certain embodiments and, as such, are not intended to limit the disclosure.

DETAILED DESCRIPTION OF THE INVENTION

Traditional intravascular lithotripsy (IVL) devices, systems, and methods can apply high energy, electrical power to generate a spark (arc) between discharge electrodes. Under appropriate conditions, sparks generated by submerged electrodes can generate pressure waves within the medium which can be applied to treat (breakup) calcified lesions within the patient's vasculature. It can be appreciated that appropriate control of such high energy systems can be paramount to effective treatment, including to safe treatment.

Intravascular lithotripsy systems, devices and methods have been described by Applicant. See PCT/2022/074607, filed Aug. 5, 2022 and entitled "INTRAVASCULAR LITHOTRIPSY BALLOON SYSTEMS, DEVICES AND METHODS", the entire contents of which are hereby incorporated by reference.

Figure 1:
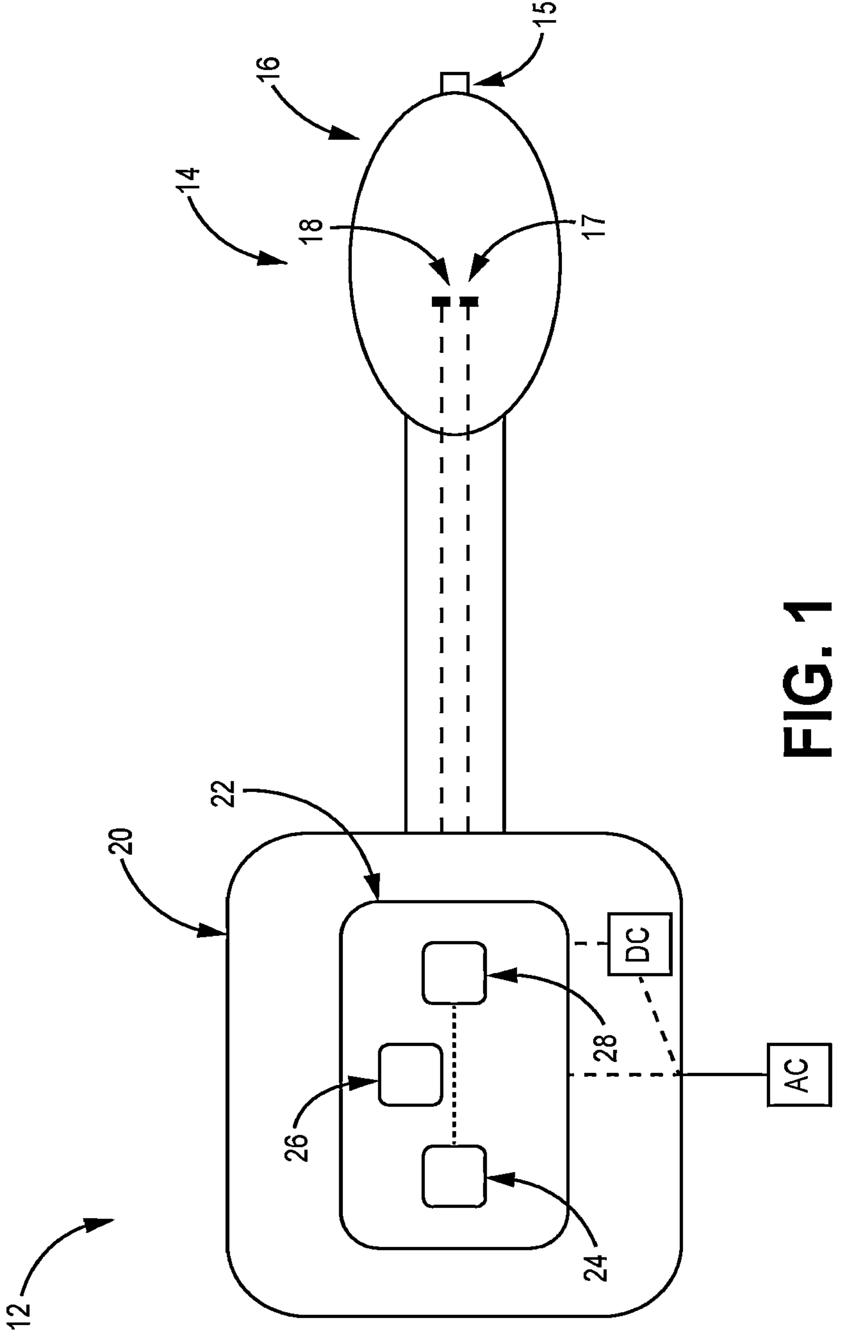
FIG. 1 illustrates a diagrammatic intravascular lithotripsy (IVL) arrangement according to one or more embodiments of the present disclosure.

As illustrated in FIG. 1, a diagrammatic layout of portions of an exemplary IVL system 12 is shown indicating control elements within the present disclosure. The illustrative IVL system 12 comprises a catheter assembly 14 including an elongate body, embodied as a catheter having guidewire 15, and a fluid-filled member 16 configured to contain conductive fluid therein, exemplified by an inflatable balloon, disposed near one end of the body and arranged to receive fluid for inflation to facilitate IVL therapy. A set of discharge electrodes 18 are shown arranged within the exemplary balloon 16, at least some of which are spaced apart by a gap 17 from each other to create a spark or electrical arc between the spaced-apart electrodes 18.

The IVL system control mechanisms described herein may be used in connection with electrodes that are within a fluid-filled member 16 configured to contain a fluid, e.g., a conductive fluid, therein. The fluid-filled member 16 embodiments may include an inflatable balloon as shown in FIG. 1, which may be compliant or non-compliant and serves to contain the fluid such that the spaced-apart electrodes 18 are submerged within the contained fluid. In addition, the fluid-filled member 16 may comprise a fillable member that is at least partially rigid and/or not flexible. In other embodiments, the fluid-filled member 16 may contain the fluid therein and wherein the spaced-apart electrodes 18 are located or submerged within the contained fluid.

Alternatively, the IVL system control mechanisms of the present disclosure may be used in connection with electrodes that are not located or surrounded by a fluid-filled or fillable member 16. In these embodiments, the IVL system may comprise spaced-apart electrodes 18 that may be continuously or periodically exposed to saline or other fluid and, during the exposure, the IVL system may generate an electrical arc between the spaced-apart electrodes 18.

The spaced-apart electrodes 18 are arranged in communication (as suggested by dashed line conductors) with an electric pulse generation system 20 to receive high voltage electrical energy for spark generation to create pressure waves for IVL therapy. In the illustrative embodiment, one electrode may be grounded and the other provided with high voltage from the electric pulse generation system 20, although in some embodiments, any voltage differential may be applied. The electric pulse generation system 20 includes an IVL control system 22 comprising a processor 24 configured for executing instructions stored on memory 26 and communications signals via circuitry 28 for IVL operations according to the processor governance. The processor 24, memory 26, and circuitry 28 are arranged in communication with each other (as suggested via dashed lines) to facilitate disclosed operations.

Appropriate control of such high energy systems can also require achieving sufficient energy at the discharge site. Given the high energy environment and microscale time periods for electronic discharge, desirable energy control within such IVL devices and systems can be challenging. Moreover, adaptable control methodologies may offer advantages to IVL effectiveness. Adjustable energy delivery can increase efficient power application, which can reduce risk to the patient. For example, beginning with a predetermined starting voltage threshold and defining a predetermined upper voltage threshold to form an acceptable voltage window may be proved. The acceptable voltage window may be coupled with series of generated voltage pulses of magnitudes that are confirmed to be within the acceptable voltage window. If, e.g., the magnitudes of the series of generated voltage pulses are below the predetermined upper voltage threshold, then the target voltage may be increased by a predetermined amount and another series of generated voltage pulses is executed. The embodiments of the IVL systems, devices and methods within the present disclosure includes operation for adjusting the total electrical energy provided to the set of electrodes for a given pulse.

Figure 2:
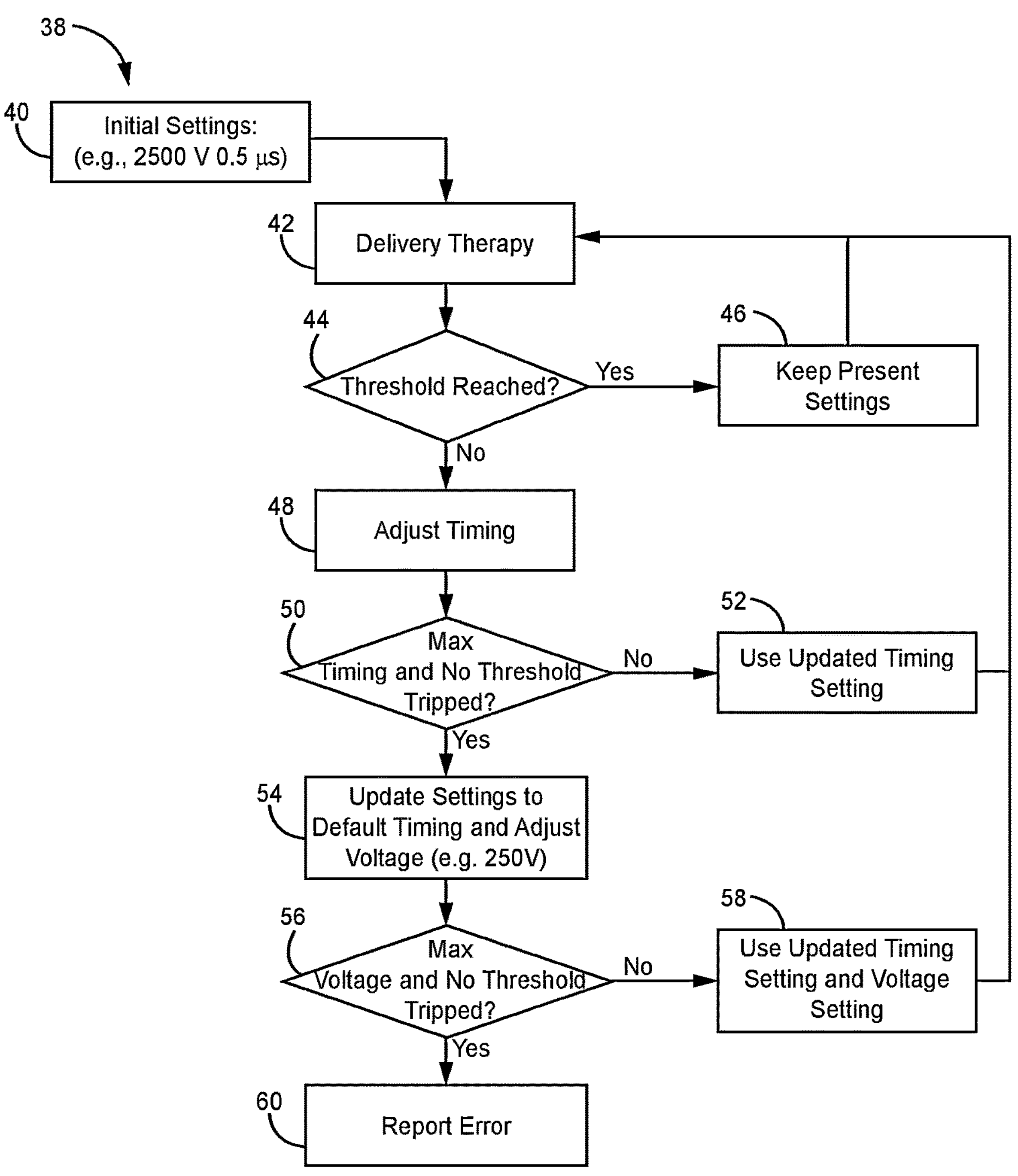
FIG. 2 illustrates a control operation flow diagram applicable to the IVL arrangement of FIG. 1 according to one or more embodiments of the present disclosure.

Referring now to FIG. 2, a flow diagram is shown concerning one embodiment of a control 38 in operation of IVL as discussed concerning boxes 40 through 60. Such control operations can be governed by the electric pulse generation system 20, and illustratively by the IVL control system 22. As discussed in additional detail herein, control 38 applies incremental changes in power parameters during cycling of applied voltage while monitoring parameters related to spark generation. For example, incrementally increasing the duration of voltage applied to the discharge electrodes can increase the likelihood of generation of an effective spark without excessive energy.

Moreover, if increases to the duration of voltage applied to the discharge electrodes fails to generate sufficient spark, incremental increase to the voltage can further increase the likelihood of generation of an effective spark without excessive power. Still further, if incrementally increased voltage fails to generate sufficient spark, duration can once again be incrementally increased before further increasing voltage. Accordingly, it can be appreciated that controlled incremental increases in duration and voltage can be implemented to achieve effective spark generation, and thus pressure wave generation, at or near the lowest required power characteristics for effective spark generation. Increasing the likelihood of reaching sufficient spark with lower power can increase the efficiency, safety, and/or reduce intensity of effective IVL therapy.

In box 40, initial settings are applied. For illustrative example, default initial settings are applied as a discharge voltage of 2500 volts (V) for a duration of 0.5 microseconds. In some embodiments, the initial settings may be determined by any suitable manner, including by use of programmable defaults, as adjusted settings based on use, for example, adjusted based on the patient characteristics, environmental conditions, procedural approach, and/or product cycle lifetime (i.e., operable age), among other aspects. From box 40, control may proceed to box 42.

In box 42, electrical energy is applied to the electrodes to deliver IVL therapy. In the first instance of proceeding from box 40 to box 42, electrical energy is applied at the initial settings, e.g., an applied voltage of 2500 V for a duration of 0.5 microseconds. When applied in a clinical setting, such that the IVL catheter is arranged within the patient's body lumen, and specifically with discharge electrodes submerged within a fluid medium within a fluid-filled member such as an angioplasty balloon, pressure wave therapy can ensue. However, as mentioned below, at present conditions, in some instances the energy provided at the initial settings may be insufficient to generate a spark at the electrodes, or may generate insufficient spark or insufficient pressure wave. From box 42, control may proceed to box 44.

In box 44, determination of threshold aspects is conducted. In the illustrative embodiment, a determined value for current applied in box 42 is compared with threshold current value. In the illustrative example, the threshold current value is embodied as a predetermined fixed value, e.g., 20 amperes (amps), but in some embodiments, may have any suitable value, for example 50 amps, 100 amps, 150 amps, 175 amps, the threshold current value for a given cycle may be determined based on the number of previous cycles in a therapy session, the number of cycles maintaining present settings (e.g., through box 46) in a therapy session, the number of particular successive cycles (e.g., number of successive cycles through box 46 or box 48 or box 52 or box 54 or box 58), the patient characteristics, environmental conditions, procedural approach, and/or product cycle lifetime (i.e., operable age), among other aspects. Additionally, although the threshold current value may be set to one value, the actual current passed during a sufficient generation of arc across the electrodes may be greater.

Responsive to determination that the determined value for current applied in box 42 is equal to or greater than the threshold current value, control may proceed to box 46. Otherwise, responsive to determination that the determined value for current applied in box 42 less than the threshold current value, control may proceed to box 48. For example, as mentioned above, insufficient spark generation may result in little or no current flow (e.g., about 0 to about 5 amps, which may represent dissipated energy into the medium without arcing) across the electrodes, which would not achieve the threshold current value, and thus would proceed to box 48.

In the illustrative embodiment, the determined current value for current applied in box 42 is embodied as the instantaneous current applied across the electrodes. In some embodiments, the determined current value may be embodied as an aggregated value, such as a time-averaged value of current applied to the electrodes. Continuing from the exemplary embodiment applying a threshold current value of 20 amps, when 20 amps is achieved by the therapy delivered, the spark generation is deemed sufficient.

It can be appreciated that the substantial occurrence of 20 amps provides considerable current across the discharge electrodes indicating the generation of meaningful spark. By comparison little or no current may flow across the discharge electrode when a spark fails to generate or when insufficient spark is generated under the applied duration and at the applicable voltage, 2500 V by example, and which can generally range between about 500 V to about 5000 V for IVL therapy, although conceivably can range between about 100 V to about 10000 V in terms of practical application.

In box 46, determination is made to maintain presently selected settings. In the illustrative embodiment, the presently selected settings include the discharge voltage of and applicable duration as applied immediately previously in box 42. For avoidance of doubt, if the initial settings have just immediately been applied in box 42, resulting in 20 amps of current, the initial settings would be applied in the next cycle of therapy. However, if the presently selected settings include updates settings, for example, updated duration and/or voltage settings from later portions of control 38, as discussed in additional detail herein, then maintaining presently selected settings would include the immediately applied updated settings. Maintaining presently selected settings proceeds openly to return to box 42, to again apply electrical energy to the electrodes to deliver IVL therapy.

In box 48, determination is made to increase the duration of applied voltage to the discharge electrodes. Continuing the example in which less than 20 amps of current indicates insufficient spark generation, rather than immediately increasing the voltage applied, the duration of applied voltage can be incrementally increased. At the microsecond-scale, increasing the duration of applied voltage can increase the likelihood of sufficient spark generation using the same voltage previously applied. This can be achieved as the result of overcoming threshold system impendence and/or other factors affecting the ease of spark generation during a given cycle at a given voltage.

The duration of applied voltage is increased by a predetermined duration interval, illustratively embodied as a fixed value, e.g., 0.5 microseconds. In some embodiments, the predetermined interval for given cycle may be determined based on factors such as the number of times therapy cycles have ensued previously during the therapy session (e.g., number of cycle intervals have proceeding through boxes 42, 44, 46, prior to proceeding to box 48), the patient characteristics, environmental conditions, procedural approach, and/or product cycle lifetime (i.e., operable age), among other aspects. In some embodiments, the predetermined duration interval for a given cycle may be varied by predetermined rate of change, for example, by percentage gain or loss by cycle. Control proceeds openly from box 48 to box 50.

In box 50, determination is made whether maximum duration has been achieved. In the illustrative embodiment, the maximum duration is a predetermined duration embodied as a fixed value, e.g., 6 microseconds. By way of example, if the control sequence progresses through cycles from initial settings of box 40 at 0.5 microseconds through box 48, until reaching 6 microseconds, the maximum duration would be achieved as a threshold value.

In some embodiments, the maximum duration for a given cycle may be determined based on the number of previous cycles in a therapy session, the number of cycles maintaining present settings (e.g., through box 46) in a therapy session, the number of particular successive cycles (e.g., number of successive cycles through box 46 or box 48 or box 52 or box 54 or box 58), the patient characteristics, environmental conditions, procedural approach, and/or product cycle lifetime (i.e., operable age), among other aspects. By deduction, in box 50, the threshold current value has not been achieved in the present cycle, although in some embodiments, affirmative determination and/or confirmation that threshold current value has not been achieved may be performed. Responsive to determination that the maximum duration has not been achieved, control proceeds to box 52. Otherwise, responsive to determination that maximum duration has been achieved, control proceeds to box 54.

In box 52, determination is made to apply the updated duration. In the illustrative embodiment, the duration has been updated in box 48 by increasing the presently selected duration by the predetermined duration interval, and determination to apply the updated duration confirms and proceeds with the updated duration. In the illustrative embodiment, the applied voltage remains as presently selected. Proceeding with the updated duration proceeds openly to return to box 42, to again apply electrical energy to the discharge electrodes to delivery therapy using the updated duration.

In box 54, the applied voltage is increased by a predetermined voltage interval. The presently selected setting for applied voltage is illustratively increased by the predetermined voltage interval. The presently selected duration is returned to the value at the initial setting, exampled as 0.5 microseconds, to be applied with the updated voltage, although in some embodiments, the updated duration may have any suitable value under newly updated voltage settings, for example, the updated duration may be determined based on the number of cycles of the therapy session when newly update voltages occur.

In the illustrative embodiment, the predetermined voltage interval is embodied as a fixed value of 250 V, such that, in the first exemplary occurrence of box 54, the presently selected applied voltage is increased to 2750 V from the value at the initial setting of 2500 V. In some embodiments, the predetermined voltage interval for a given cycle may be determined based on the number of previous cycles in a therapy session, the number of cycles maintaining present settings (e.g., through box 46) in a therapy session, the number of particular successive cycles (e.g., number of successive cycles through box 46 or box 48 or box 52 or box 54 or box 58), the patient characteristics, environmental conditions, procedural approach, and/or product cycle lifetime (i.e., operable age), among other aspects.

In box 56, determination is made whether maximum voltage has been achieved. In the illustrative embodiment, the maximum voltage is a predetermined voltage embodied as a fixed value, e.g., 3500 V. By way of example, if the control sequence progressed through cycles from initial settings of box 40 at 2500 V through box 54, until reaching 3500 V, the maximum voltage would be achieved as a threshold value.

In some embodiments, the maximum voltage for a given cycle may be determined based on the number of previous cycles in a therapy session, the number of cycles maintaining present settings (e.g., through box 46) in a therapy session, the number of particular successive cycles (e.g., number of successive cycles through box 46 or box 48 or box 52 or box 54 or box 58), the patient characteristics, environmental conditions, procedural approach, and/or product cycle lifetime (i.e., operable age), among other aspects. By deduction, in box 56, the threshold current value has not been achieved in the present cycle, although in some embodiments, affirmative determination and/or confirmation that threshold current value has not been achieved may be performed. Responsive to determination that maximum voltage has not been achieved, control proceeds to box 58. Otherwise, responsive to determination that maximum voltage has been achieved, control proceeds to box 60.

In box 58, determination is made to apply updated voltage. In the illustrative embodiment, the voltage has been updated in box 54 by increasing the presently selected voltage by the predetermined voltage interval, and determination to apply the updated voltage confirms and proceeds with the updated voltage. The duration was updated in box 45 to return to the value at the initial setting, exampled as 0.5 microseconds, and proceeds to be applied with the updated applied voltage. Proceeding with the updated voltage proceeds openly to return to box 42, to again apply electrical power to the electrodes to delivery therapy using the updated voltage and updated duration.

In box 60, determination of error occurs. Responsive to determination of error, an error message is provided. Such error message illustratively terminates the therapy session, but in some embodiments, may take other safety and/or communication actions, for example, such as displaying an error communication to a user.

In the illustrative embodiment, by deduction, responsive to error determination, the maximum voltage and maximum duration can be determined not to have generated a spark, although in some embodiments, insufficient spark generation may be determined. In some embodiments, responsive to error determination, failed and/or insufficient spark generation under maximum voltage and maximum duration may be determined by affirmative determination and/or confirmation. Following box 60, process control automatically terminate.

Within the discussion of the control 38, exemplary increases in duration have been mentioned, although in some instances, for example, in certain cycles of control 38, voltage level may be decreased, for example, in certain cycles of control 38. For example, duration and/or voltage may be changed in a given cycle according to control 38 to decrease incrementally to achieve appropriate conditions, for example, to achieve appropriate discharged energy as discussed in additional detail herein relative to consideration of the voltage levels of an energy storage system, for example, a capacitance system, 112 before and after discharge.

Figure 3A:
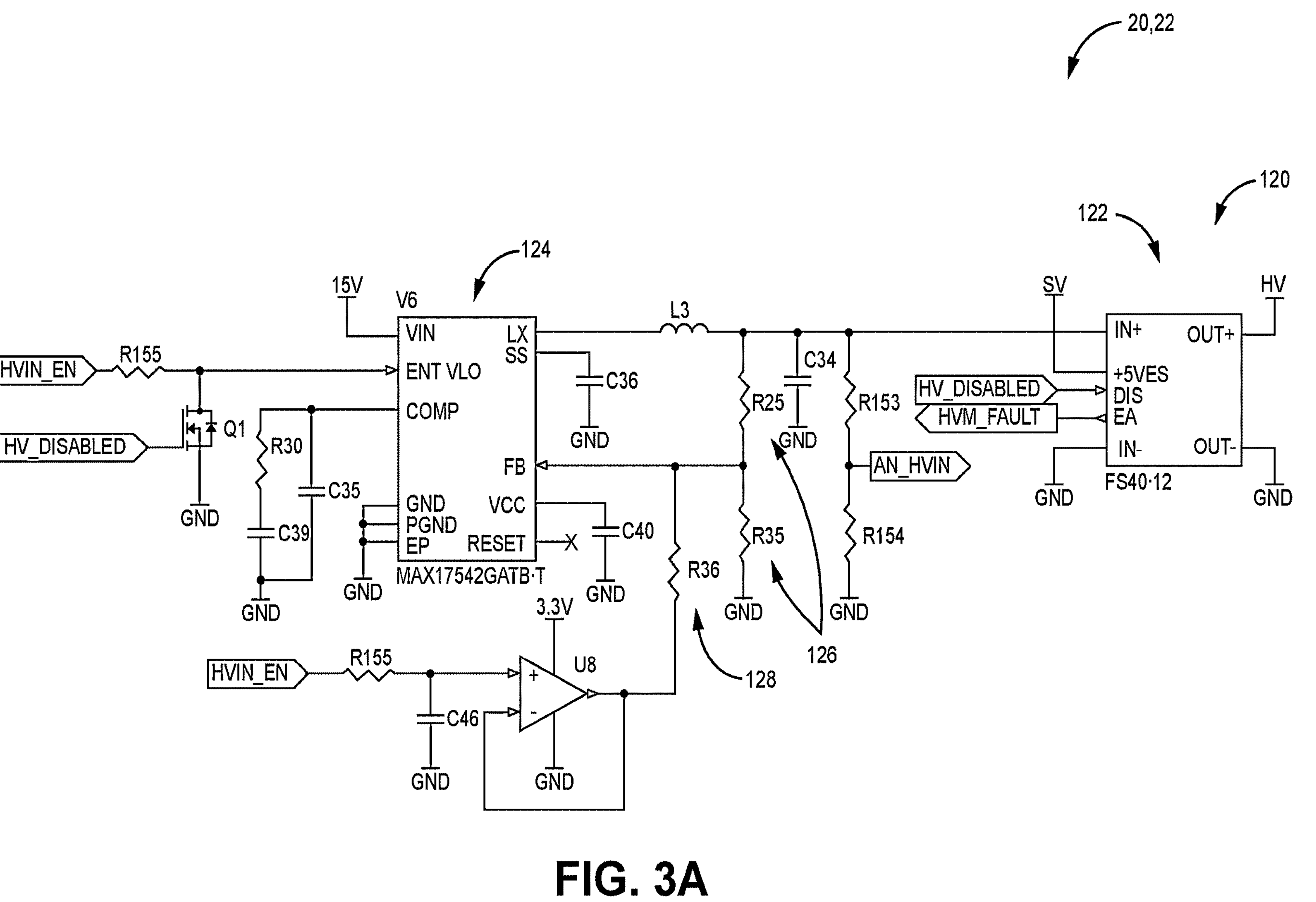
FIG. 3A illustrates portions of circuitry arrangements of one or more of the IVL arrangement and control operation of FIGS. 1 and 2 according to one or more embodiments of the present disclosure.
Figure 3B:
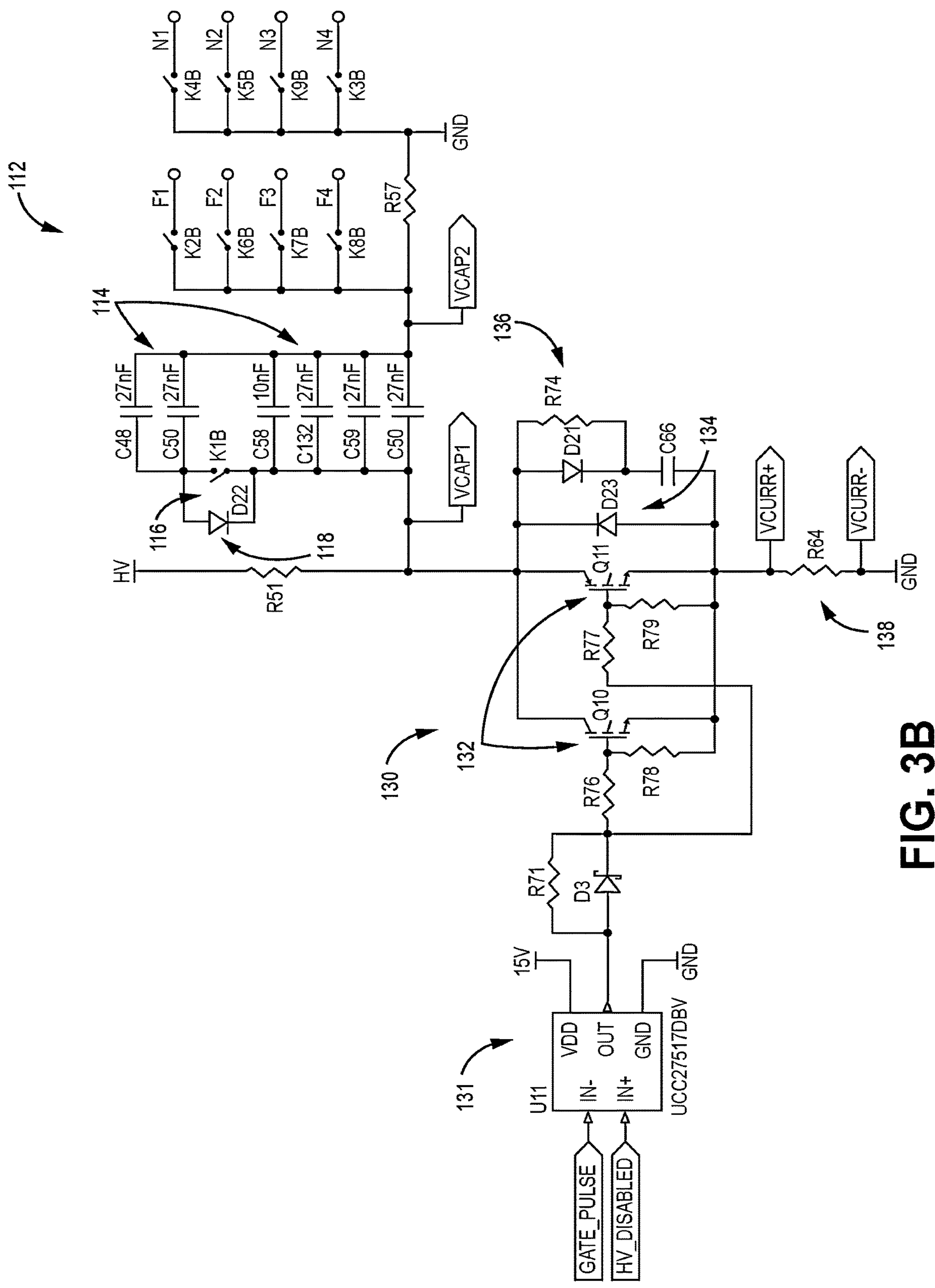
FIG. 3B illustrates portions of circuitry arrangements of one or more of the IVL arrangement and control operation of FIGS. 1 and 2 according to one or more embodiments of the present disclosure.
Figure 4A:
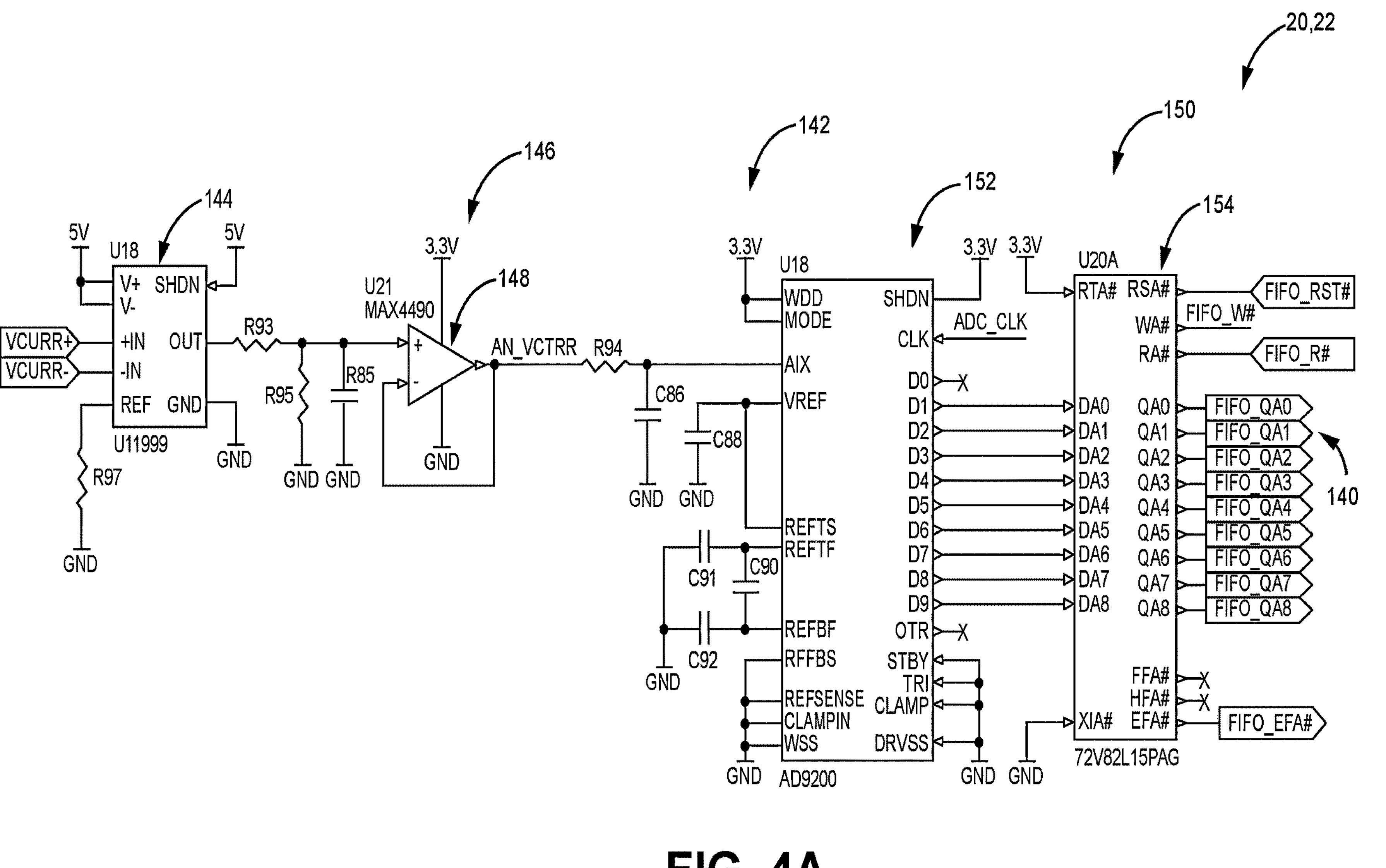
FIG. 4A illustrates additional portions of circuitry arrangements of one or more of the IVL arrangement and control operation of FIGS. 1 and 2 according to one or more embodiments of the present disclosure.
Figure 4B:
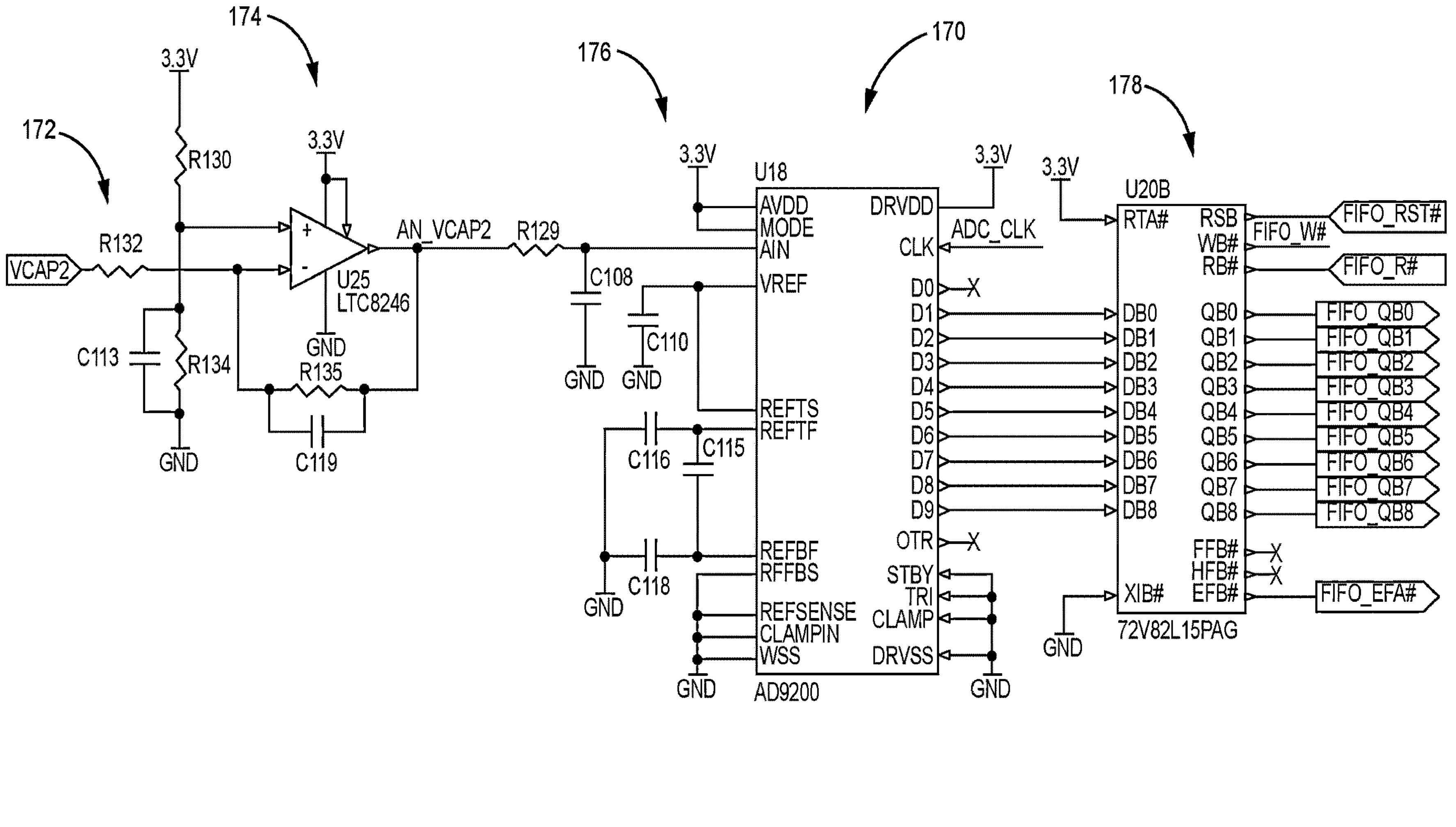
FIG. 4B illustrates additional portions of circuitry arrangements of one or more of the IVL arrangement and control operation of FIGS. 1 and 2 according to one or more embodiments of the present disclosure.
Figure 4C:
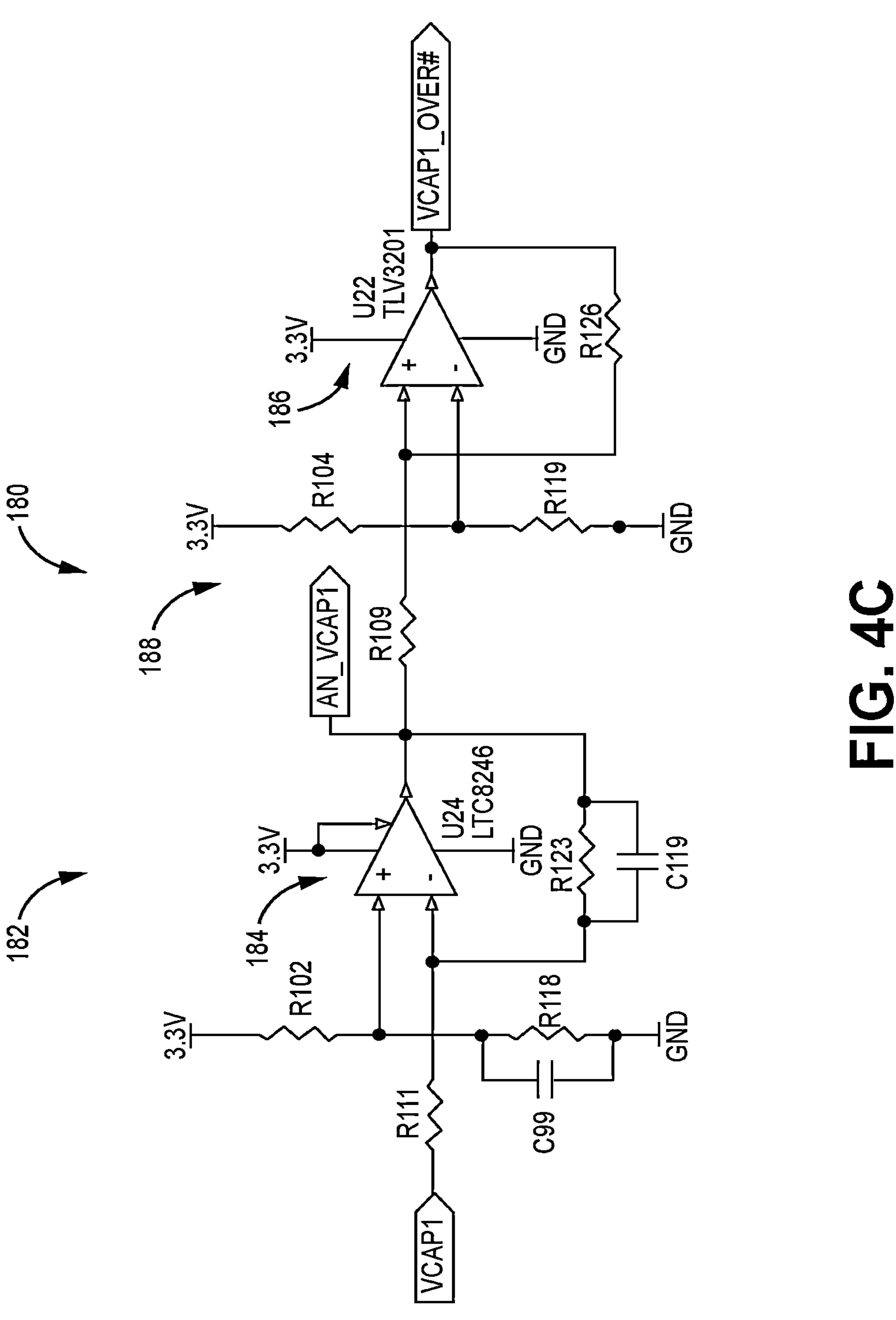
FIG. 4C illustrates additional portions of circuitry arrangements of one or more of the IVL arrangement and control operation of FIGS. 1 and 2 according to one or more embodiments of the present disclosure.
Figure 4D:
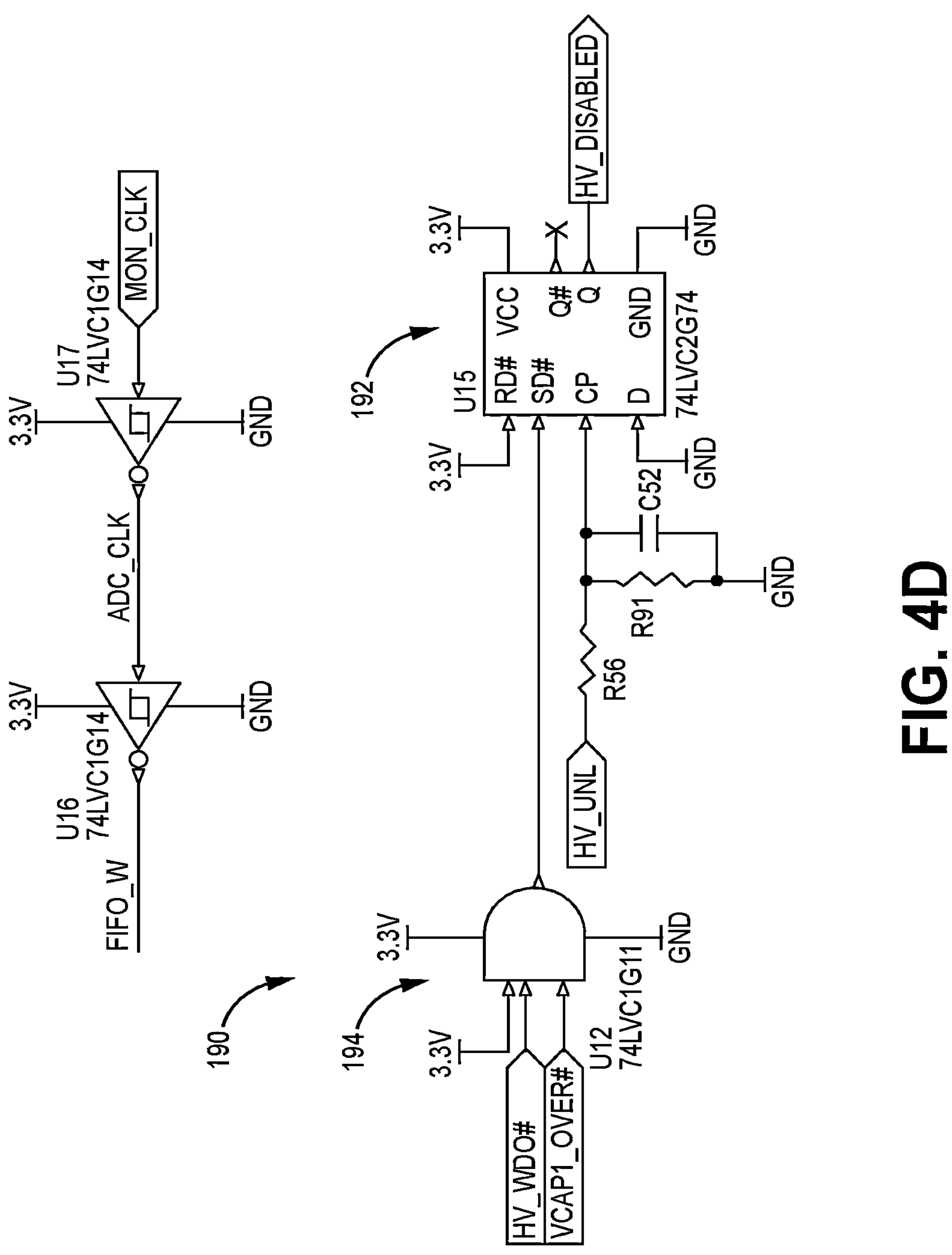
FIG. 4D illustrates additional portions of circuitry arrangements of one or more of the IVL arrangement and control operation of FIGS. 1 and 2 according to one or more embodiments of the present disclosure.

With reference to FIGS. 3A and 3B, portions of the illustrative electric pulse generation system 20, including portions of the IVL control system 22, are disclosed herein including various features and/or circuitry which may be implemented as portions of circuitry 28, although in some embodiments, such systems 20, 22 may share components and/or have isolated components as applicable, for example, such that circuitry 28 is intended to be diagrammatic and may also represent circuitry embodied by system 20 alone as applicable. In the illustrative embodiment, the IVL control system 22 includes an adjustable energy storage system, illustratively an exemplary capacitance system, 112 for selective adjustment of the energy storage capacity or magnitude applied for providing electrical energy to the electrodes. We refer hereinafter to energy storage system 112, illustrated by but certainly not limited to, the illustrative capacitance system.

The energy storage system 112 receives charge electrical energy from a power source of the electric pulse generation system 20. The energy storage system 112 provides discharge electrical energy to the electrodes (e.g., illustratively via VCAP2 and grounding), as discussed in additional detail herein.

The adjustable energy storage system 112 illustratively includes a number, e.g., one or more, of energy storage units, exemplified as individual capacitors 114, defining an energy storage network. In the illustrative embodiment, each energy storage unit 114 may be sized to have the same energy storage capacity and may be arranged for parallel connection with the other energy storage unit(s) in the energy storage network, although in some embodiments, any suitable size and/or arrangement of the energy storage unit(s) may be provided to support variable energy storage for IVL therapy. A relay system 116 may be arranged in connection with at least some of the energy storage elements 114 of the network. The relay system 116 comprises one or more relays for selectively connecting energy storage element(s) 114 together to receive charge and to discharge electrical energy to the electrodes.

In the illustrative embodiment, the relay system 116 includes an engaged arrangement in which all energy storage elements 114 of the network are connected for IVL use. Energy storage element(s) 114, when connected for IVL use, may be connected with other portions of the electric pulse generation system 20 to exchange electrical energy under other control operations. For example, under typical charge control operations, energy storage elements 114 connected for IVL use by relay system 116 may receive charge from power supply, and/or under typical discharge control operation, energy storage elements 114 connected for IVL use by relay system 116 may provide discharge energy to the electrodes 18. Accordingly, it can be appreciated that the relay system 116 can selectively connect all energy storage element(s) 114 for use in the IVL therapy, to provide a maximum energy storage magnitude.

Additionally, the relay system 116 includes a disengaged arrangement in which fewer than all energy storage elements 114 of the network are connected for IVL use as suggested in FIGS. 4A-4D. A number of energy storage elements 114, illustratively two energy storage elements, are rendered disconnected from the other energy storage element(s) by disengagement of the relay system 116 for ease of description but without limitation. Energy storage elements 114 disconnected for IVL use by relay system 116 cannot receive charge from power supply, and/or under typical discharge control operation, energy storage elements 114 disconnected for IVL use by relay system 116 cannot provide discharge energy to the electrodes 18. Energy storage elements which are disconnected for use in IVL therapy may be discharged apart from the electrodes (e.g., for safe reduction of stored power), illustratively via diode 118 arranged in parallel with the relay system 116.

It can be appreciated that by adjustment of the energy storage capacity available to provide electrical energy to the electrodes, the total amount of energy provided to the electrodes can be controlled. The stored energy can be indicated according to $\frac{1}{2}C*V^2$, where V represents the voltage and C represents the capacitance, such that applied electrical energy is directly proportional to the amount of energy connected in use. Accordingly, by selectively engaging the relay system 116 to close the circuit and connect the disconnected energy storage element(s), the energy storage capacity of the IVL system can be adjusted to provide variable energy levels to the electrodes. Although the illustrative embodiment includes relay control for connection and/or disconnection of a pair of energy storage elements, any suitable number of relays and/or energy storage elements may be applied to provide adjustable energy storage capacity for IVL therapy.

In the illustrative embodiment, the IVL control system 22 is configured to govern the applied stored energy. The IVL control system 22 illustratively determines the amount of stored energy to be applied, and upon determination that a change in the energy storage magnitude is desired, the IVL control system 22 operates the relay system 116 accordingly. For example, the IVL control system 22 may determine that one voltage pulse desires and/or requires lower energy storage magnitude and may communicate to operate the relay system 116 in the disengaged arrangement.

For one or more subsequent voltage pulses, the IVL control system 22 may determine that another voltage pulse desires and/or requires greater energy storage magnitude and may communicate to operate the relay system 116 in the engaged arrangement. For one or more further subsequent voltage pulses, the IVL control system 22 may determine that lower energy storage magnitude is again desired and/or required and may return the relay system 116 to the disengaged arrangement. Accordingly, the IVL control system 22 may operate the relay system 116 as needed to provide adjustable energy storage magnitudes for any given voltage pulse within a series of voltage pulses.

The applied energy storage may be adjusted on an ongoing basis, for example, for any given pulse. In practice, adjusting the energy storage capacity or magnitude may be conducted in conjunction with the level of voltage to be applied and/or in consideration of other aspects of power, efficiency, and/or technique. Moreover, under the lifetime of applied devices and systems, typical wear to components can alter the electrical and/or physical characteristics thereof, which may benefit from adjustment to the energy storage that is applied. For example, even small wear to electrodes can vary the spacing (gap) between a set of electrodes which can alter the conditions of the arc between electrodes. Accordingly, adjustable energy storage magnitude can accommodate variations in the electrodes and/or or portions of the discharge system under repeated use, whether in individual therapy sessions or otherwise.

With continued reference to FIGS. 3A and 3B, embodiments of the disclosure are directed to systems and methods for adjusting the voltage provided to charge the energy storage system 112 as charge voltage. The charge voltage is illustratively provided as input to the energy storage system 112 as energy accumulation for discharge to generate a voltage pulse, controlled for variable charge. The charge voltage is illustratively controlled by a charge control system 120 of the IVL control system 22.

In the illustrative embodiment, the charge control system 120 provides accurate control of charge voltage via high frequency switched control signals from the processor 24. The switched control signal ("HVIN_VSET"), illustratively embodied as a pulse width modulated (PWM) signal, is amplified for control of high voltage supply. A high voltage DC/DC converter system 122 receives indication of the switch control signal within the range of about 0 V to about 12 V, and provides a corresponding charge voltage illustratively within the range of about 0 V to about 4000 V.

In the illustrated embodiment, the charge control system 120 includes a buck regulator system 124 for conditioning the low voltage power. The buck regulator system 124 is illustratively embodied as an integrated circuit (IC) to provide signal conditioning with low pass filtering and buffering of the PWM signal. The buck regulator system 124 receives a conditioned PWM signal with feedback for providing controlled low voltage power to the converter system 122 for applying high voltage power.

Resistors 126 can scale down the feedback voltage appropriately for the IC operation, to provide a variable feedback voltage to the buck regulator system 124 within a range of about 0 V to about 3.3 V at the additional resistor 128. As the duty-cycle of the PWM signal increases from zero to 100 percent, the filtered signal increases from zero volts to 3.3 volts, which can increase the current provided to the feedback network, and can require less voltage to achieve regulation, for example, at resistors, inductors, and/or capacitors arranged between the buck regulator system 124 and the converter system 122.

Referring still to FIGS. 3A and 3B, embodiments of the disclosure are directed to systems and methods for controlling the active time for discharge voltage pulses provided to the electrodes. A switching signal (e.g., "GATE_PULSE") is provided by the processor 24 for high voltage switching via low voltage signaling. In the illustrative embodiment, the switching signal is applied to precisely activate a discharge switch system 130. The discharge switch system 130 is illustratively embodied to implement a driver 131 and semiconductor devices 132 as gate switches.

The gate switches 132 are illustratively embodied as insulated gate bipolar transistors (IGBT) having n-type gate-controlled arrangement. On active state of the switching signal to the driver 131, the gate switches 132 are activated into their conducting state to communicate discharge of energy from the energy storage system 112 to the electrodes. On inactive state of the switching signal the gate switches 132 are deactivated into their non-conducting states, blocking discharge of the energy storage system 112 to the electrodes.

In the illustrative embodiment, the gate switches 132 are arranged as active high devices, although in some embodiments, may be implemented as active low devices. Gate-controlled, active high IGBTs can provide precision control of discharge from the energy storage system 112, but may be implemented by any suitable manner including by other suitable semiconductors (e.g., p-type, FET, etc.) and/or other control designs (e.g., collector, emitter control, etc.).

In the illustrative embodiment, the discharge switch system 130 includes an anti-parallel diode 134 arranged to reduce reverse-voltage stresses on the gate switches 132. A disable signal ("HV_DISABLED") is provided to the driver 131 which permits discharging of energy to the electrodes on inactive (low) signal, and may activate (high) to disable high voltage discharge under direction of the processor 24 and/or other safety systems. The snubber system 136 is illustratively embodied as a resistor-capacitor-diode (RCD) snubber network arranged to reduce voltage transients that may exceed rated voltages of various high-voltage components.

Referring now to FIGS. 4A-4D, the IVL control system 22 illustratively includes electrical power monitoring system 140. The electrical power monitoring system 140 is configured to conduct monitoring of various parameters of electrical power of the IVL device and systems, illustratively including sensing of current and voltage delivered to the electrodes, and voltage of the adjustable energy storage system 112.

The electrical power monitoring system 140 illustratively includes a current monitoring system 142. The current monitoring system 142 is embodied to sense the current delivered to the electrodes for a given voltage pulse. As discussed in additional detail herein, the current delivered to the electrodes can be considered in determining the power characteristics for subsequent voltage pulses.

In the illustrative embodiment as shown in FIGS. 4A-4D, the current monitoring system 142 receives indication of the voltage levels applied in each voltage pulse for determining current delivered to the electrodes. Returning briefly to FIGS. 3A and 3B, a shunt resistor 138 is arranged within the high-voltage current path establishing a proportional voltage (e.g., "VCURR+", "VCURR−"). The proportional voltage is communicated to the current monitoring system 142 as shown in FIGS. 4A-4D.

A chip comprising an amplifier 144 is arranged to scale-up the proportional voltage, and provides the analog result to a conditioning network 146, embodied to include a resistor-capacitor network for scaling and/or filtering. The conditioning signal is buffered by a buffering amplifier 148, the output of which is provided to an analog-to-digital conversion (ADC) system 150 for digital conversion.

The ADC system 150 illustratively includes a converter 152 and memory 154. In the illustrative embodiment, the converter 152 provides digital output from the analog input, and the memory 154 is embodied as a first-in-first-out (FIFO) device for intermediate storage of digital outputs. The memory 154 illustratively receives the same clock signal driving the converter 152, to allow quick sampling of a number of measurement points with low-jitter. Memory outputs are provided to the processor 24 for consideration in overall IVL therapy control.

The IVL control system 22 illustratively includes a current monitoring system which compares the output signal ("VCURR") generated by the chip comprising an amplifier 144 with a threshold value. The threshold value is embodied to be generated by a variable duty cycle PWM signal ("ISNS_ISET") from the processor 24. The PWM signal can be low-pass filtered and/or buffered before delivery to a comparator. Responsive to the measured current exceeding the threshold value, the current monitoring system can assert an error signal (e.g., "ISNS OVER #") to avoid overcurrent conditions.

The electrical power monitoring system 140 illustratively includes a voltage monitoring system 170. The voltage monitoring system 170 is embodied to sense the voltage between the set of electrodes. As discussed in additional detail herein, the voltage between the electrodes for a given pulse can be considered in determining the power characteristics for subsequent voltage pulses.

In the illustrative embodiment, the voltage monitoring system 170 includes a resistor network 172 arranged to attenuate the (switched) voltage of one of the electrodes of a set (e.g., "VCAP1"). The attenuated signal is provided to an op amp network 174 for filtering and offsetting for output to digital conversion. The output from the op amp network 174 is provided to the ADC conversion system 176 for digitization, including storage in FIFO memory 178 for access by the processor 24.

The electrical power monitoring system 140 may illustratively include an energy storage capacity voltage monitoring system 180 configured for monitoring the voltage within the adjustable energy storage system 112. Monitoring the voltage of the energy storage system 112 can allow determination of the stored energy of the energy storage system 112. Moreover, comparison of the stored energy of the energy storage system 112 before and after discharge can provide indication of the total energy delivered during a given discharge cycle. Such total energy data can be considered to increase confidence in determining whether a sufficient spark has been generated for IVL therapy.

In the illustrative embodiment, the voltage monitoring system 180 includes a voltage limiting system configured to monitor net voltage of the energy storage system 112 during charging. In the illustrative embodiment, voltage monitoring is discussed relative to the connected energy storage elements 114, more specifically, those energy storage elements which are connected to provide controlled discharge energy for IVL therapy, and not energy storage elements which are disconnected via the relay system 116 if any.

The voltage monitoring system 180 receives indication of the voltage of the energy storage system 112 during charging ("VCAP1"). The system 180 illustratively includes an amplifier configuration 182 comprising an amplifier 184 and a comparator 186. The comparator 186 is illustratively arranged to compare to the voltage with a fixed voltage, and to responsively trigger a signal (e.g., "VCAP1_OVER #") when the voltage of the energy storage system 112 exceeds the fixed voltage. In the illustrative embodiment, the fixed voltage is embodied as setpoint generated by a resistor-resistor-capacitor network 188 above normal operation, but before damage will occur to various HV components.

An intermediate voltage of this circuit (e.g., "AN_VCAP1") can be used to monitor progress during the charging cycle of the energy storage system 112. The intermediate voltage illustrative represents a heavily attenuated indication of the high voltage provided by the energy storage system to the electrodes ("VCAP_1"). Such attenuated signal can allow monitoring of high voltage systems while handling lower voltage indications thereof.

Figure 5:
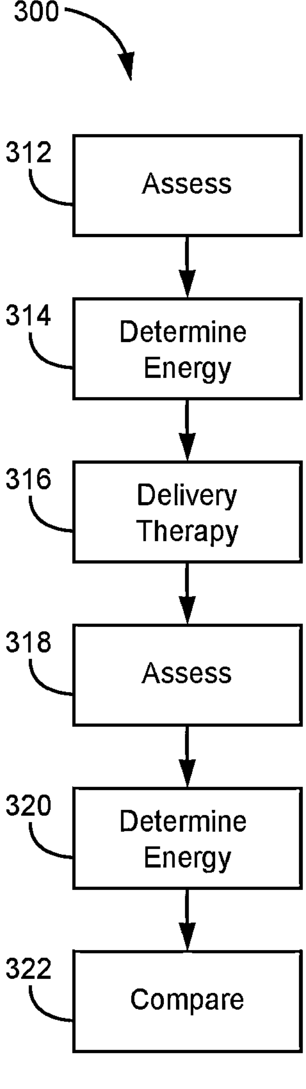
FIG. 5 illustrates a flowchart for controlling and delivering voltage to electrodes and generating shock waves according to one or more embodiments of the present disclosure.

Referring now to FIG. 5, and with continued reference to FIGS. 1 and 3, the IVL system 12 can consider energy of the energy storage system 112 in operation. By monitoring energy of the energy storage system 112 before and after a discharge event, indication of the generation (and/or sufficiency) of spark can be determined as discussed in additional detail regarding the illustrative embodiment with reference to operation 300 concerning boxes 312 through 322.

In box 312, assessment of the energy storage system 112 is conducted. In the illustrative embodiment, the assessment includes determination of a voltage of the energy stored by the energy storage system 112. As mentioned above, the voltage monitoring system 180 can monitoring voltage of the energy storage system 112, for example, via the voltage limiting system during charging. In some embodiments, the assessment may include determination of any other suitable parameters to support energy monitoring of the energy storage system 112.

In box 314, the energy of the energy storage system 112 is determined. In the illustrative embodiment, the energy of the energy storage system 112 is determined based on the measured voltage according to $\frac{1}{2}C*V^2$. Accordingly, the processor 24 can compute the current energy of the energy storage system 112, including the energy stored just before discharge of energy to the electrodes.

In box 316, IVL therapy can be attempted. In the illustrative embodiment, a voltage pulse can be delivered to the electrodes. The voltage pulse can be applied according to the control arrangement as mentioned herein, for example, based on a determined duration in a control sequence.

In box 318, assessment of the energy storage system 112 is conducted. Assessment of the energy storage systems 112 in box 218 is embodied as occurring immediately after attempted IVL therapy in box 216 to provide an indication of the energy state of the energy storage system 112 immediately after (attempted) discharge to the electrodes. In the illustrative embodiment, the assessment includes determination of a voltage of the energy stored by the energy storage system 112, embodied as conducted by the voltage monitoring as mentioned above, although in some embodiments, assessment of the energy storage system 112 in box 318 may differ from box 312 in methodology and/or practice.

In box 320, the energy of the energy storage system 112 is determined. In the illustrative embodiment, the energy of the energy storage system 112 is again determined based on the measured voltage according to $\frac{1}{2}=C*V^2$ just as in box 214, yet after attempted delivery of IVL therapy. In some embodiments, determining energy of the energy storage system 112 in box 320 may differ in methodology and/or practice from that in box 214. Accordingly, the processor 24 can compute the current energy of the energy storage system 112, including immediately after (attempted) discharge of energy to the electrodes.

In box 322, comparison between energy determinations is conducted. The amount of energy determined within the energy storage system 112 in box 314 is illustratively subtracted from the amount of energy determined within the energy storage system 112 in box 320, such that the result represents the amount of energy discharged from the energy storage system 112 under a single attempt to deliver IVL therapy.

The amount of energy discharged can be considered to determine whether a spark (or sufficient spark) has occurred such that IVL therapy occurs. In the illustrative embodiment, a threshold energy discharge represents a discharged energy level which confidently indicates spark sufficient for IVL has occurred. Accordingly, in box 322, comparing the stored energy levels before and after discharge to determine whether the threshold energy discharge has been achieved can indicate spark for IVL therapy.

In the illustrative embodiment, and with reference to FIG. 2, the threshold energy discharge is a fixed predetermined value, for example, 600 millijoules (e.g., 3700 V, 90 nanofarad). However, in some embodiments, the threshold energy level for a given cycle may be determined based on the number of previous cycles in a therapy session, the number of cycles maintaining present settings (e.g., through box 46 of FIG. 2) in a therapy session, the number of particular successive cycles (e.g., number of successive cycles through box 46 or box 48 or box 52 or box 54 or box 58), the patient characteristics, environmental conditions (e.g., location within patient's body such as above the knee or above the knee), procedural approach, and/or product cycle lifetime (i.e., operable age), among other aspects.

Comparison of energy levels of the energy storage system 112 which indicates a spark for IVL therapy has occurred can responsively cause further therapy at the same duration, energy level, threshold characteristic, and/or threshold adjusted for other parameters. Comparison of energy levels of the energy storage system 112 which indicates a spark for IVL therapy has not occurred can cause adjustment to the duration and/or energy level applied, for example, as discussed concerning control operation 38.

In some embodiments, the threshold current value can be applied together with the threshold energy discharge, such that either threshold can individually indicate a spark for IVL therapy. In some embodiments, both thresholds may be required to be met to indicate a spark for IVL therapy.

Consideration of the energy states of the energy storage system 112 can provide desirable monitoring of IVL operations. For example, such monitoring can be less intrusive by reducing the need for direct measurements at the electrodes. Moreover, in high power applications, reliable consideration of the energy states can promote confidence over mere direct measurement in unpredictable high energy arc scenarios.

The IVL control system 22 illustratively includes an external watchdog system configured to assist in safe operation. The watchdog system includes an integrated circuit configured to trigger an error under lack of a timely toggled input signal to ensure appropriate high voltage operation. In some embodiments, the watchdog system may be formed externally including processor, memory, and/or circuitry distinct from or shared with the IVL control system 22.

Returning to FIGS. 3A and 3B, in the illustrative embodiment, the IVL control system 22 includes an umbrella monitoring system 190 configured to assist in safe operation. The umbrella monitoring system 190 illustratively includes a flip flop 192 and logic gate 194 for consideration of monitoring signals. The logic gate 194 is arranged to receive monitoring signals, embodied as energy storage system overvoltage ("VCAP1_OVER #") from the voltage monitoring system 180, high voltage warning ("HV_WDO #) from the watchdog system, and in some embodiments, may receive overcurrent from the current monitoring system ("ISNS_OVER #").

The logic gate 194 is embodied as an AND gate and the flip flop 192 embodied as an asynchronous D-flip flop, such that activation signals from the gate 194 which last longer than the minimum clock pulse width of the flip flop 192 cause an assertion of outputs to disable high voltage output (e.g., "HV_DISABLED"), but activation signals from the gate 194 shorter than the minimum clock pulse width of the flip flop 192 do not raise disabling outputs from the umbrella monitoring system 190.

Assertion of the signal to disable high voltage output ("HV_DISABLED") is illustratively provided to the discharge switch system 130 to disable voltage pulse switch activation to the electrodes. In the illustrative embodiment, the disabling output signal is provided to the driver 131 and indirectly to alter on/off operation of the gate switches 132. Such disabling output signal is illustratively provided to low-voltage supplies, e.g., buck regulator system 124, and high voltage modules, e.g., converter system 122.

Accordingly, the logic gate 194 receives monitoring signals discussed above comprising: (1) energy storage system overvoltage ("VCAP1_OVER #") from the voltage monitoring system 180, (2) high voltage warning ("HV_WDO #) from the watchdog system, and in some embodiments, (3) may receive overcurrent from the current monitoring system ("ISNS_OVER #"). These monitoring signals ac also connected to a three-input AND logic gate [U12], which is upstream of a D flip-flop with asynchronous set and reset functionality [U15], so that any signal that asserts for longer than the minimum pulse width of the flip-flop [U15] will cause its outputs [HV_DISABLED, HV_DISABLED #] to assert. These signals travel downstream and inhibits the operation of the gate driver [U11], variable low-voltage supply [U6], high-voltage module [U7], and slightly changes the turn-on and turn-off operation of the switching devices [Q10, Q11] via transistors [Q12, Q13]." This system allows any one of monitoring signals to disable the output of the system if asserted longer than an established duration.

Within the present disclosure, the ability to run off of AC mains or battery DC can afford versatility of power and control for IVL therapy. Unlike known IVL systems, certain embodiments within the present disclosure can avoid sitting idle until fully (or substantially) recharged in order to be applied in IVL therapy, for example, if insufficiently charged by the time IVL therapy is desired. Accordingly, such costly delays, or interruptions, in procedure can be avoided with embodiments of the present disclosure. The electric pulse generation system 20 illustratively includes a battery power storage system, and is configured to selectively charge the energy storage system 112 from battery stored energy only, from the battery power storage system while connected to mains, such as outlet power, or directly from DC power converted from the AC mains without the battery power storage system. When plugged in to AC mains, regulated DC power is delivered directly to the high voltage systems. In operational states in which the current demand for IVL operations is high, the battery power storage system charge current can be reduced to allow for higher IVL operations system current. When not plugged in to AC mains, battery power can be delivered directly to energy storage system 112. In the illustrative embodiment, systems and devices of power management, including for example, inverters, conditioners, power storage devices, and/or related aspects may be comprised by the electric pulse generation system 20 to provide applicable power to the IVL control system 22.

Examples of suitable processors may include one or more microprocessors, integrated circuits, system-on-a-chips (SoC), among others. Examples of suitable memory, may include one or more primary storage and/or non-primary storage (e.g., secondary, tertiary, etc. storage); permanent, semi-permanent, and/or temporary storage; and/or memory storage devices including but not limited to hard drives (e.g., magnetic, solid state), optical discs (e.g., CD-ROM, DVD-ROM), RAM (e.g., DRAM, SRAM, DRDRAM), ROM (e.g., PROM, EPROM, EEPROM, Flash EEPROM), volatile, and/or non-volatile memory; among others. Communication circuitry 58 includes components for facilitating processor operations, for example, suitable components may include transmitters, receivers, modulators, demodulators, filters, modems, analog/digital (AD or DA) converters, diodes, switches, operational amplifiers, and/or integrated circuits. In some embodiments, memory 26 may represent one or more memory devices operable for IVL therapy operation. For example, each memory (e.g., 154, 178) may be included as part of memory 26, shared, or isolated therefrom.

Within the present disclosure, consideration of a set of discharge electrodes has been discussed in the context of a pair of electrodes, one of which may serve as a cathode and the other of which may serve as an anode, at a given instance. However, the number of electrodes in a set may be greater than a pair, for example, including one or more cathodes communicating with one or more anodes. Additionally, devices, systems, and methods within the present disclosure may include more than one communicating group of electrodes, whether electrically arranged serially, parallel, or independently from each other.

Power control operations disclosed herein may be applied equally, simultaneously, and/or sequentially to individual sets or groups of electrodes, in a given IVL therapy cycle. For example, threshold current value may be applied collectively to all deployed electrodes or to individual groups or sets of electrodes. Determinations made with respect to power control may be applied equally to related electrodes, or may be individualized to groups or sets of electrodes, in a given IVL therapy cycle. Within the present disclosure, supporting components, such as power supplies, sensors, and other implementing structures and/or features for performing IVL operations as disclosed herein are embodied as sub-portions of the electric pulse generation system 20 and/or IVL control system 22, for example, as parts of circuitry and/or instructions.

Figure 6:
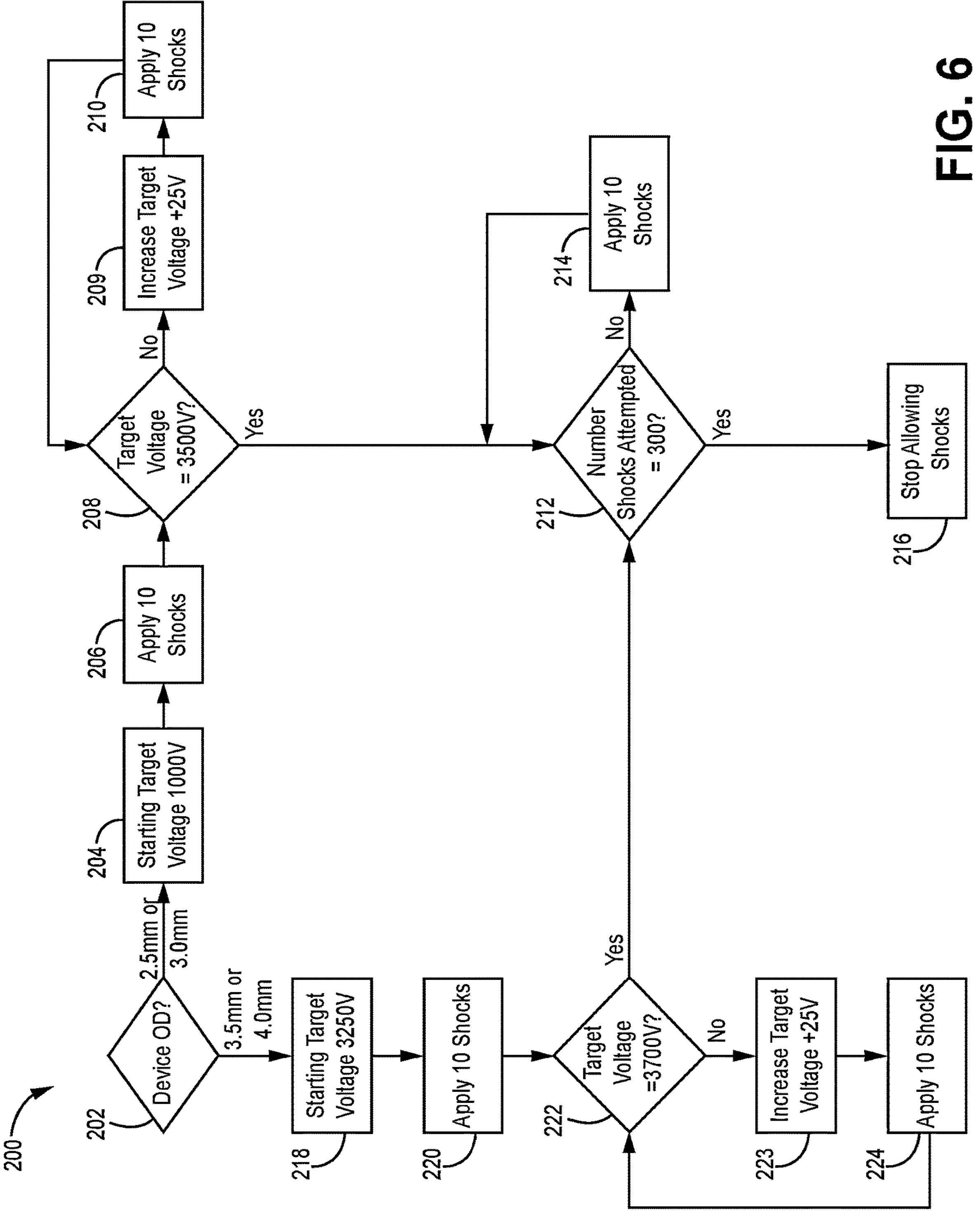
FIG. 6 illustrates a control operation flow applicable to the IVL arrangement of FIG. 1 according to one or more embodiments of the present disclosure

Referring now to FIG. 6, an exemplary flow diagram is shown concerning another embodiment of a control 200 in operation of an embodiment of an IVL system, specifically the number of voltage pulses generated and the magnitude of the generated pulses. It is understood that the control 200 may be combined with aspects of the control system and method embodiments described above in relation to FIGS. 1-5.

Control operations of control 200 may be governed by the electric pulse generation system 20, and illustratively by the IVL control system 22 discussed above in connection with FIG. 1. As discussed further herein, control system 22 may control the number of generated voltage pulses in a series (or a plurality of series) of voltage pulses. An acceptable voltage window comprises a predetermined starting voltage magnitude and a predetermined upper voltage magnitude. IVL control system further comprises a predetermined voltage magnitude for incremental increasing of voltage magnitude after each series of voltage pulses if the magnitudes of the executed voltage pulses is within the acceptable voltage window. Separate sets of predetermined control data may be provided in control system 22 for IVL systems comprising balloons that are of identifiable characteristics such as, without limitation, different sizing, e.g, 2.5 mm, 3.0 mm, 3.5 mm and/or 4.0 mm.

An exemplary embodiment of an IVL system may comprise a 2.5 mm or a 3.0 mm balloon, wherein the control system 22 comprises control data comprises an exemplary starting target voltage of 3000V (predetermined lower voltage threshold), voltage pulse series comprising an exemplary 10 pulses, and an exemplary incremental voltage increase of 25V if the voltage pulse series magnitudes are less than an exemplary upper voltage threshold of 3500V. As the skilled artisan will recognize, the incremental voltage increase may comprise any voltage magnitude, including without limitation within 1V to 250V. An exemplary voltage increase may comprise 25V, but may be greater or less than 25V in certain embodiments. As the artisan will recognize, the predetermined starting voltage may be less than 3000V and the predetermined upper voltage threshold may be greater than 3500V. Thus, an exemplary starting voltage may, without limitation, comprise 2500V and an exemplary upper voltage threshold may comprise 4100V. In other embodiments, an exemplary predetermined starting voltage maybe greater than 3000V and an exemplary upper voltage threshold may be greater than 3250V.

Another exemplary embodiment may comprise a 3.5 mm or a 4.0 mm balloon, wherein the control system 22 comprises control data comprises an exemplary starting target voltage of 3250V (predetermined lower voltage threshold), voltage pulse series comprising 10 pulses, and an incremental voltage increase of 25V if the voltage pulse series magnitudes are less than an exemplary predetermined upper voltage threshold of 3700V.

With continued reference to FIG. 1, and in some embodiments FIG. 2, FIG. 6 illustrates initiation of a voltage pulse generation and control system 200 that begins with box 202 which requires determination of a particular balloon characteristic of interest, for example the outer diameter ("OD") of the IVL system's balloon. In a first embodiment, if the balloon's outer diameter is, e.g., 2.5 mm or 3.5 mm, then in box 204 the starting voltage is set to 3000V, also referred to as the predetermined lower voltage threshold of the acceptable voltage magnitude window). The IVL therapy is initiated in box 206 by application of a series of voltage pulses (or shocks) from the electric pulse generation system 20 wherein each voltage pulse travels to the electrodes 18 within the balloon 16. If, in box 208, the target voltage magnitude is not at the predetermined upper voltage threshold, e.g., 3500V, then as in box 109, the target voltage is increased by an exemplary 25V (from 3000V to 3025V) and another series of voltage pulses (in this case 10 pulses) is executed, as in box 210 at 3025V. This process continues with cycling between boxes 208, 209 and 210 until the target voltage is at 3500V. When the target threshold voltage, or predetermined upper voltage threshold, is reached, and/or in some embodiments a predetermined maximum or desired number of voltage pulses, e.g., 300 pulses (or shocks) have been generated, then as in box 212, control system 22 determines if the number of generated voltage pulses (or shocks) in the plurality of series of voltage pulses has reached a maximum, or desired, number of pulses, e.g., 300 voltage pulses. If the maximum or desired, e.g., 300, voltage pulse threshold has not been reached, then as in box 214 another series of, e.g., 10, voltage pulses (or shocks) are applied. When the maximum or desired, e.g., 300 voltage pulse threshold has been reached, then as in box 216, additional voltage pulses (or shocks) are not allowed.

The predetermined maximum number of voltage pulses in various embodiments of the present disclosure may be within the range of 10-300 voltage pulses. The exemplary embodiments discussed herein comprise a predetermined maximum number of voltage pulses equal to 300 pulses. In other embodiments, the maximum number of voltage pulses may be greater than 300 pulses.

In a second embodiment, with continued reference to FIG. 1, and in some embodiments, FIG. 2, if the balloon's outer diameter is determined in box 202 to be, e.g., 3.5 mm or 4.0 mm, then the electric pulse generation system 20 initiates therapy at box 118 the starting voltage is set to 3250V, also referred to as the predetermined lower voltage threshold of the acceptable voltage magnitude window). The IVL therapy is initiated in box 220 by application of a series of voltage pulses from the electric pulse generation system 20 wherein each voltage pulse travels to the electrodes 18 within the balloon 16. If, in box 222, the target voltage magnitude is not at the predetermined upper voltage threshold, e.g., 3500V, then as in box 223, the target voltage is increased by an exemplary 25V (from 3250V to 3275V) and another series of voltage pulses (in this case 10 pulses) is executed, as in box 224, at 3275V. This process continues with cycling between boxes 222, 223 and 224 until the target voltage is at 3700V. When the target threshold voltage, or predetermined upper voltage threshold, is reached, and/or in some embodiments a maximum or desired number of pulses, e.g., 300 pulses (or shocks when applied to the one or more pairs of spaced-apart electrodes) have been generated, then as in box 212, control system 22 determines if the number of generated voltage pulses (or shocks) in the plurality of series of voltage pulses has reached a maximum, or desired, number of pulses, e.g., 300 voltage pulses. If the maximum or desired, e.g., 300, voltage pulse threshold has not been reached, then as in box 214 another series of, e.g., 10, voltage pulses (or shocks) are applied. When the maximum or desired, e.g., 300 voltage pulse threshold has been reached, then as in box 216, additional voltage pulses (or shocks) are not allowed.

Alternatively, the physician conducting the IVL therapy according to the voltage pulse generation and control system 200 may determine that the therapy is complete at a point during execution of the therapy. If the therapy is determined to be completed, then the physician may terminate the process of the voltage pulse generation and control system 200 at any point.

In some embodiments, the voltage pulse generation and control system 200 may comprise modification of the duration of applied voltage within, or across, one or more of the plurality of series of voltage pulses in accordance with the embodiments discussed above in connection with FIG. 2. For example, duration may be increased, or decreased, by a predetermined duration interval, illustratively embodied as a fixed value, e.g., 0.5 microseconds. In some embodiments, the predetermined interval for given cycle may be determined based on factors such as the number of times therapy cycles have ensued previously during the therapy session (e.g., number of series of voltage pulses that have been executed by proceeding through boxes 206, 208 and 210, or 220, 222 and 224), the patient characteristics, environmental conditions, procedural approach, and/or product cycle lifetime (i.e., operable age), among other aspects. In some embodiments, the predetermined duration interval for a given cycle may be varied by predetermined rate of change, for example, by percentage gain or loss by cycle.

Figure 7:
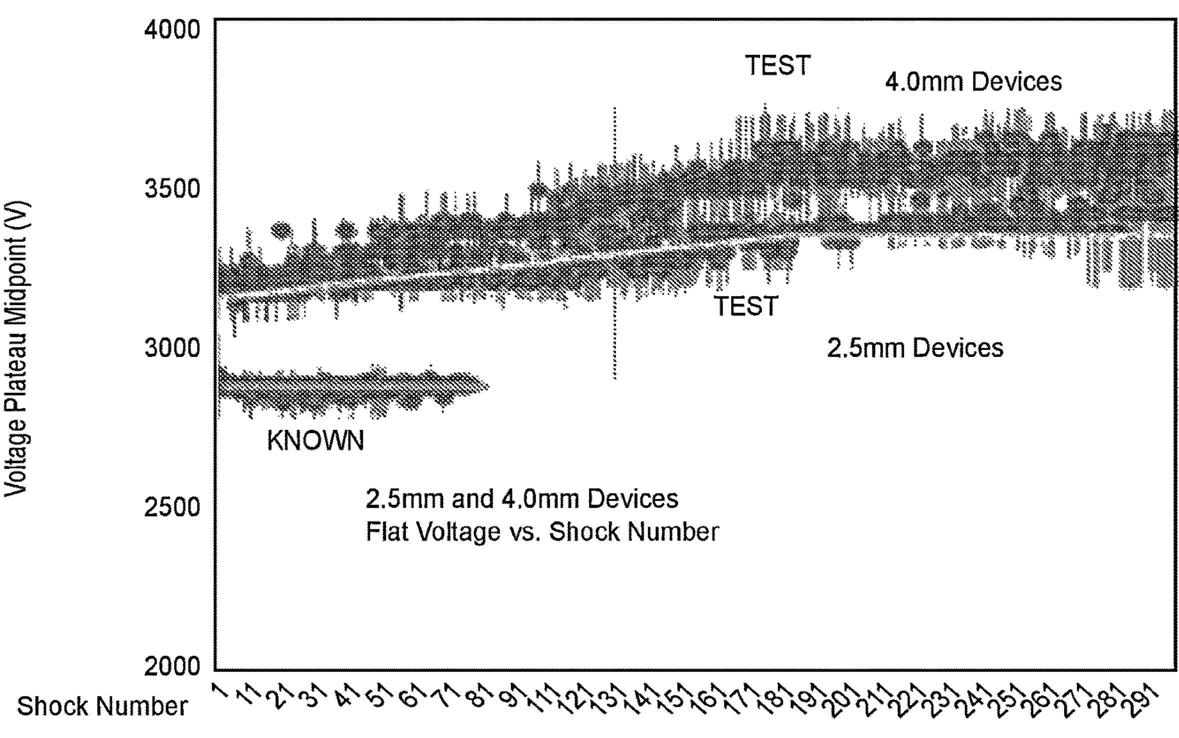
FIG. 7 illustrates graphic comparisons of voltages applied to a known IVL device and to embodiments of IVL devices according to the present disclosure.

FIG. 7 presents a graphic comparison of known IVL devices comprising 2.5 mm and 4.0 mm OD balloons (KNOWN) with IVL devices according to the present disclosure and comprising 2.5 mm and 4.0 mm OD balloons (TEST).

The KNOWN devices permit 80 voltage pulses or shocks to be generated. The TEST devices generated 300 voltage pulses or shocks. During the comparative testing, for each voltage pulse, the voltage peak magnitude was obtained and plotted for each tested device. The KNOWN devices provide a relatively flat or constant voltage for each voltage pulse or shock number and begin at a lower voltage magnitude than the TEST devices. The TEST devices were operated and controlled in accordance with the disclosed embodiments herein as, for example, illustrated in FIG. 3.

In contrast, each of the 2.5 mm and 4.0 mm TEST devices begin at a higher voltage magnitude than the KNOWN devices. The 2.5 mm TEST device begins at a lower voltage than does the 4.0 mm device. As illustrated, both the 2.5 mm and the 4.0 mm TEST device voltage (lower data cluster) rise slowly over the generated voltage pulses, plateauing at approximately 180 pulses, thereafter remaining substantially flat or constant. Referring back to FIG. 3, this pattern of increasing voltage, followed by a flattened or constant voltage region conforms with boxes 104-110 (2.5 mm) and boxes 118-124 (4.0 mm). In each case, the average voltage of the 4.0 mm TEST device is greater than that of the 2.5 mm TEST device.

Figure 8:
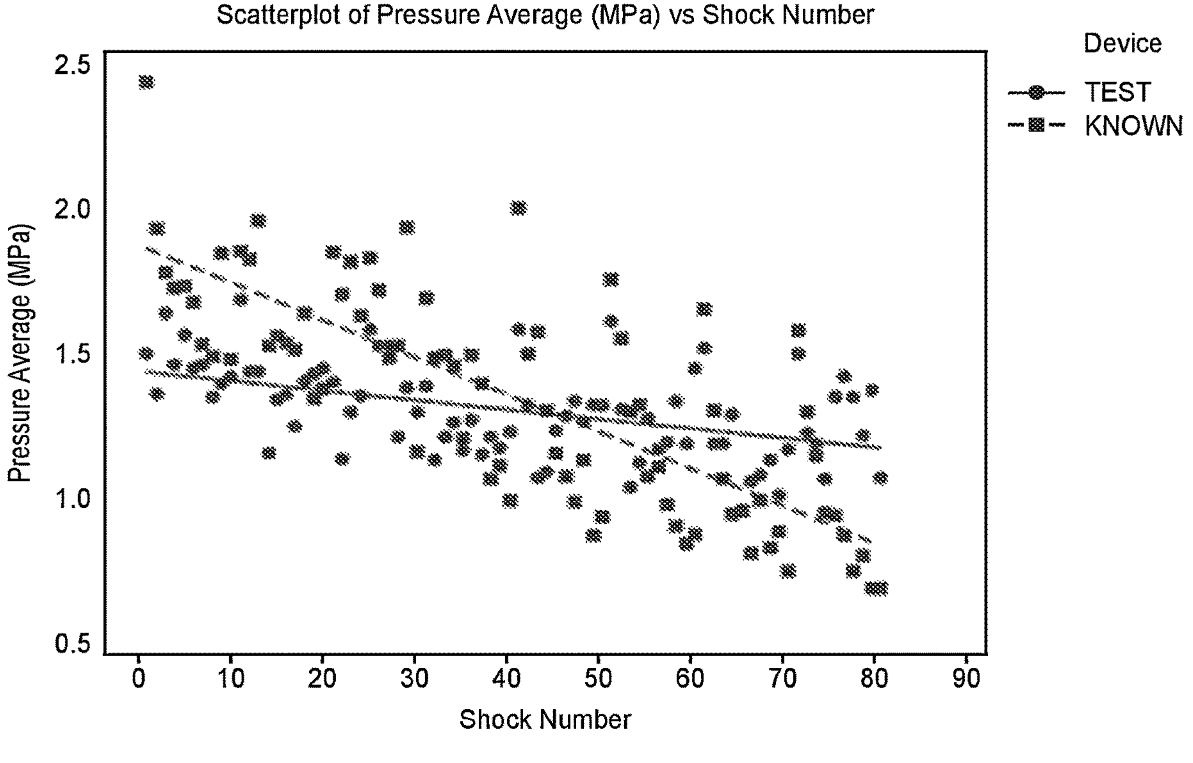
FIG. 8 illustrates a graphic comparison of average peak pressure generated over 80 voltage pulses by a known IVL devices and embodiments of IVL devices according to the present disclosure.

FIG. 8 illustrates a comparison of the TEST and KNOWN IVL devices and a subset of the data of FIG. 7, i.e., comparing the first 80 voltage pulses for each device. Here, the voltage pulse (or shock number) is compared with the average pressure generated during each voltage pulse. The KNOWN data (with a constant voltage in each voltage pulse presents (dashed line) a relatively severe decrease in pressure output as the voltage pulses progress over time. In contrast, the TEST data (solid line) obtained using the voltage and pulse generation algorithm of FIG. 2, presents a pressure output line that decreases at a much smaller angle or slope. Thus, the pressure output of the TEST IVL devices provides a more stable or constant pressure output than the KNOWN IVL devices. The KNOWN IVL devices have a pronounced pressure output decay as the voltage pulses progress. More specifically, the TEST IVL devices provide a decrease in pressure output over 80 pulses that is less than 0.25 MPa.

The pressure output, as tested, was measured in-vitro using pressure sensors (hydrophones) positioned externally to the catheter balloon within the acoustic field generated by device pulse delivery. The device under test and hydrophones were immersed in de-gassed, deionized water maintained at approximately body temperature.

Figure 9:
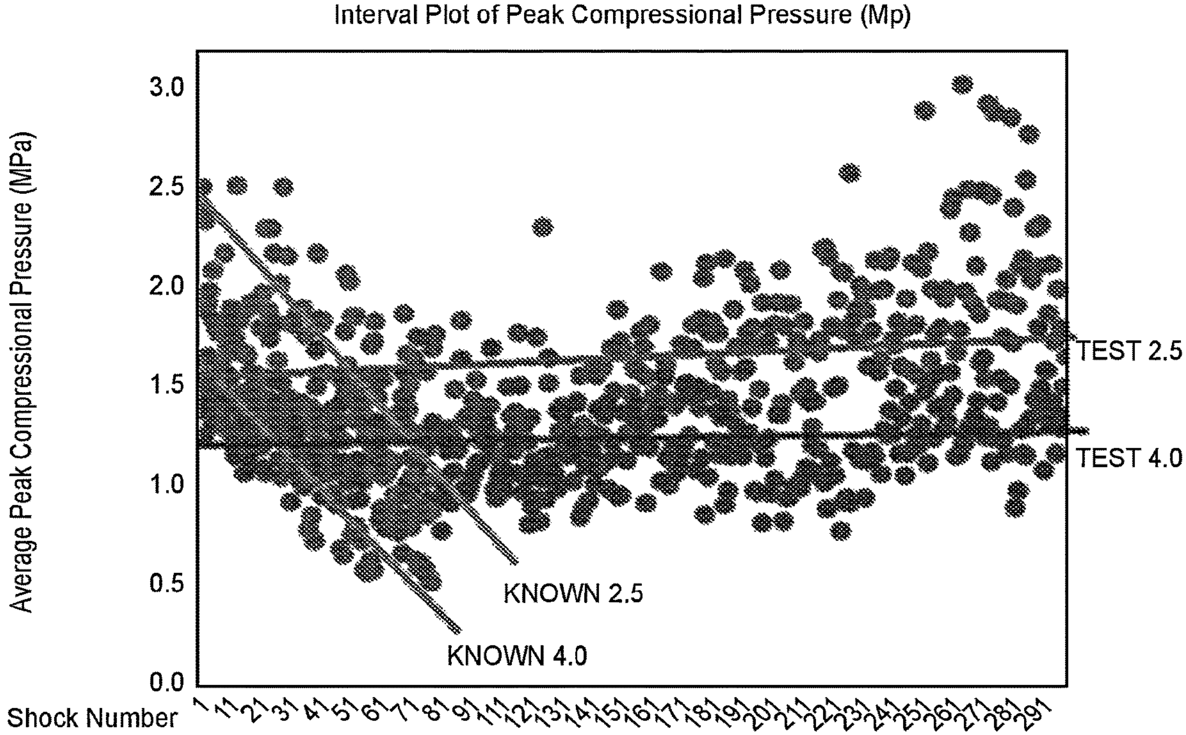
FIG. 9 illustrates a graphic comparison of average peak pressure generated over 80 voltage pulses by a known IVL device and over a predetermined maximum number of voltage pulses by embodiments of IVL devices according to the present disclosure.

This concept is further demonstrated in FIG. 9, where the average pressure generated by 80 pulses of the KNOWN IVL devices (2.5 mm and 4.0 mm) with constant voltage magnitude is compared with the average pressure generated by the TEST IVL devices (2.5 mm and 4.0 mm) according to the voltage pulse and control method of FIG. 2.

As shown in FIG. 9, the KNOWN 2.5 mm and 4.0 mm devices both provide severely decreasing pressure output slope lines as the voltage pulses progress to 80 pulses. In contrast, the TEST 2.5 mm and 4.0 mm devices provide relatively flat, constant or stable pressure output slope lines as the voltage pulses progress to 300 pulses. Moreover, the slopes of the TEST pressure output lines appear to increase slightly as the voltage pulses progress which may be beneficial in cracking difficult calcified regions. Again, the KNOWN IVL devices have a pronounced and significant pressure output decay over 80 pulses. The TEST IVL devices do not have a pressure decay over 300 voltage pulses.

In summary, the IVL devices operated and controlled according to the present disclosure provide an increasing voltage to the voltage pulses until the upper voltage magnitude threshold is reached. Then, the voltage progress at the upper voltage magnitude threshold until 300 pulses have been executed, or the physical determines therapy is complete. This, as shown above, leads to constant and/or slightly increasing pressure output from each voltage pulse. The pressure output magnitudes, and associated slopes, may be manipulated by modifying the magnitude of each incremental increase in voltage. In some embodiments, the voltage magnitude may be incrementally increased as in FIG. 2. In others, the voltage magnitude may be increased incrementally for at least two series of voltage pulses, then held constant for one or more voltage pulses, then subsequent voltage pulse series may resume the incremental increase in magnitude. In other embodiments, the voltage magnitude may be decreased for one or more series of voltage pulses. All combinations of voltage increase, voltage decrease, and/or no change in voltage over a plurality of a series of voltage pulses in order to manipulate the resulting pressure output are within the scope of the present invention.

In addition, with reference to the above disclosure, various embodiments of the disclosure may provide a pressure output that is substantially the same for all balloon sizes, wherein the balloon sizes may be within a range from 2 mm to 4 mm outer diameter. In these embodiments, larger balloon sizes do not necessarily result in a lower pressure output than the pressure output of a relatively smaller balloon size.

The data of FIGS. 8 and 9, and in combination with the pressure magnitude output control 200 of FIG. 6, also demonstrate that IVL devices operated according to the present disclosure are also capable of stable operation and pressure output over at least 300 voltage pulses. This is in contrast to the pronounced pressure decay of the KNOWN IVL devices over just 80 voltage pulses.

Moreover, the data of FIGS. 8 and 9, in combination with the pressure magnitude output control 200 of FIG. 6, confirm that the IVL control system 22 shown in FIG. 1 is controllable such that the pressure output following an electrical arcing event between two spaced-apart electrodes can be controlled within upper and lower pressure magnitude thresholds or a pressure magnitude window. Further, the pressure output can be controlled using embodiments of the present disclosure in a pattern of increasing pressure over the procedure, decreasing pressure over the procedure, constant pressure over the procedure, and any combination thereof.

Examples of suitable processors may include one or more microprocessors, integrated circuits, system-on-a-chips (SoC), among others. Examples of suitable memory, may include one or more primary storage and/or non-primary storage (e.g., secondary, tertiary, etc. storage); permanent, semi-permanent, and/or temporary storage; and/or memory storage devices including but not limited to hard drives (e.g., magnetic, solid state), optical discs (e.g., CD-ROM, DVD-ROM), RAM (e.g., DRAM, SRAM, DRDRAM), ROM (e.g., PROM, EPROM, EEPROM, Flash EEPROM), volatile, and/or non-volatile memory; among others. Communication circuitry 58 includes components for facilitating processor operations, for example, suitable components may include transmitters, receivers, modulators, demodulators, filters, modems, analog/digital (AD or DA) converters, diodes, switches, operational amplifiers, and/or integrated circuits. In some embodiments, memory 26 may represent one or more memory devices operable for IVL therapy operation. For example, each memory (e.g., 154, 178) may be included as part of memory 26, shared, or isolated therefrom.

Within the present disclosure, consideration of a set of discharge electrodes has been discussed in the context of a pair of electrodes, one of which may serve as a cathode and the other of which may serve as an anode, at a given instance. However, the number of electrodes in a set may be greater than a pair, for example, including one or more cathodes communicating with one or more anodes. Additionally, devices, systems, and methods within the present disclosure may include more than one communicating group of electrodes, whether electrically arranged serially, parallel, or independently from each other.

Figure 10:
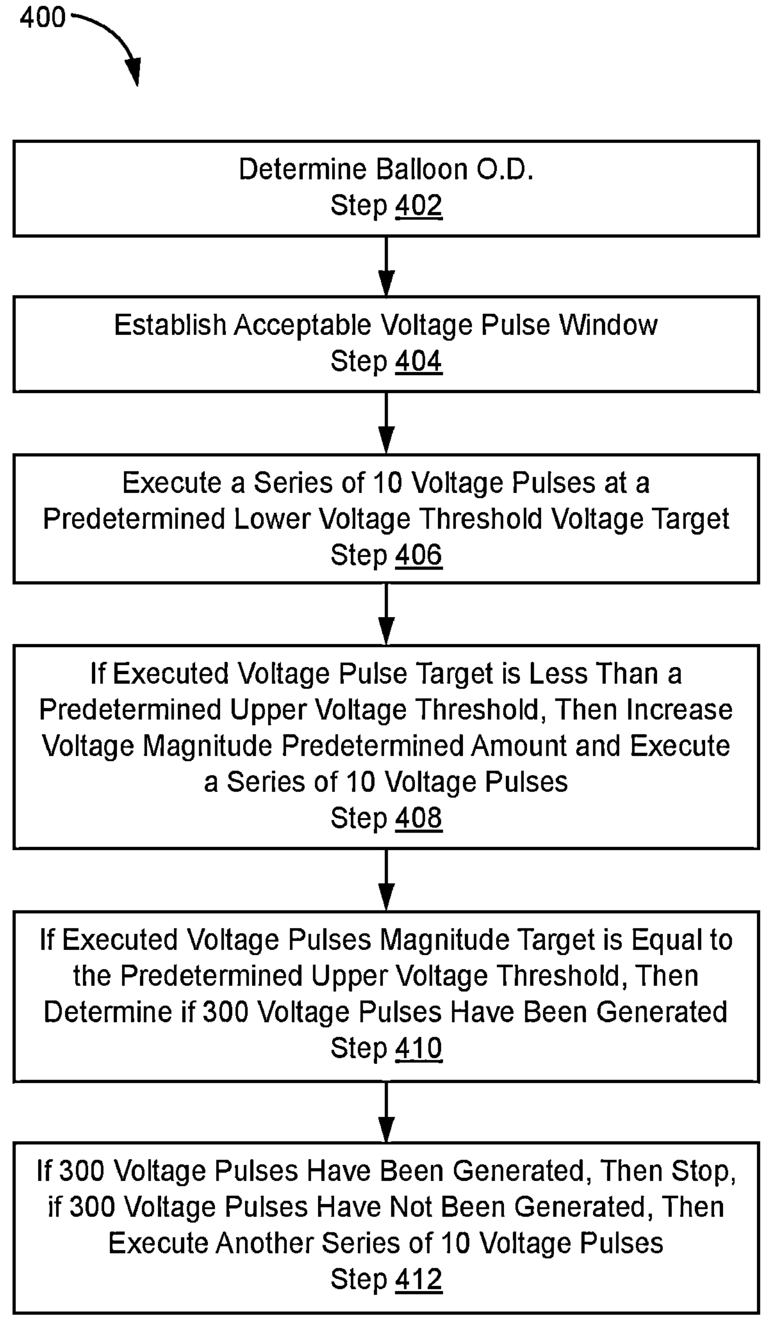
FIG. 10 illustrates an exemplary flowchart method according to the present disclosure.

FIG. 10 provides an exemplary flowchart illustrating an exemplary method 400 of one embodiment of the present invention. Thus, step 402 provides for determination of the subject IVL device's balloon outer diameter or OD. This may be done with manual entry into the IVL control system discussed above. Alternatively, connecting the catheter with the IVL control system may provide automatic detection and determination of the balloon's OD. Step 404 provides for establishing an acceptable voltage pulse window, comprising as described above, predetermined lower and upper voltage magnitude thresholds which may be stored in the IVL control system. Step 406 provides for execution of a series of voltage pulses to be controlled and generated by the IVL control system, in an illustrative and exemplary case 10 pulses may be used, at the predetermined lower voltage magnitude threshold. Step 408 provides that if the IVL control system determines that the last executed series of voltage pulses was not executed at the predetermined upper voltage threshold target, then the IVL control system may instruct execution and generation of another series of voltage pulses. Step 410 provides that if the IVL control system determines that the last executed series of voltage pulses was executed at the predetermined upper voltage threshold target, then the IVL control system seeks to determine if the illustrative and exemplary 300 voltage pulses have been executed during the current therapy. If, according to step 412, 300 voltage pulses are determined to have been executed, the IVL control system stops the procedure, allowing no further voltage pulse generation. On the other hand, if 300 voltage pulses have not been executed, then the IVL control system instructs another series of voltage pulses to be executed and at the predetermined upper voltage threshold target magnitude.

In certain embodiments, the devices, systems and methods described herein may comprise 1 pulse/second, 2 pulses/second or 3 pulses/second. In some embodiments, the pulses/second generated by the described embodiments may be within the range of 1 to 5 pulses/second.

EXEMPLARY EMBODIMENTS

The following non-limiting and exemplary embodiments are supported by the present disclosure.

Exemplary Embodiment Set 1

1. An intravascular lithotripsy system comprising:
   at least one set of electrodes for arrangement within a body lumen while disposed within an inflatable balloon;
   an electric pulse generation system for providing electrical energy to the at least one set of electrode to generate spark for intravascular lithotripsy (IVL) therapy, the electric pulse generation system including an IVL control system comprising a processor for executing instructions stored on a memory, and circuitry configured for communication of signals based on operation of the processor, the IVL control system configured to:
   generate an initial series of voltage pulses to the at least one set of electrodes, wherein the magnitude of each voltage pulse in the initial series of voltage pulses comprises a target voltage that is set at a predetermined lower voltage magnitude threshold,
   determine whether a threshold parameter is achieved, and
   responsive to determination that the threshold parameter is not achieved, increase the voltage magnitude by a predetermined amount, and
   generate another series of voltage pulses at the increased voltage magnitude for application to the at least one set of electrodes.

2. The intravascular lithotripsy system of embodiment 1, wherein the IVL control system is configured to continue to determine whether a threshold parameter is achieved after each generated series of voltage pulses.

3. The intravascular lithotripsy system of embodiment 2, wherein the threshold parameter comprises a predetermined upper voltage magnitude threshold.

4. The intravascular lithotripsy system of embodiment 3, wherein the IVL control system is configured to determine if the number of voltage pulses generated does not exceed a predetermined maximum number of voltage pulses.

5. The intravascular lithotripsy system of embodiment 3, wherein the predetermined maximum number of voltage pulses is within a range of 10 to 300 voltage pulses.

6. The intravascular lithotripsy system of embodiment 4, wherein if the IVL control system is configured to determine that the predetermined number of voltage pulses have not been generated, and if the predetermined number of voltage pulses have not been generated, then the IVL control system is further configured to execute another series of voltage pulses at the predetermined upper voltage magnitude threshold.

7. The intravascular lithotripsy system of embodiment 4, wherein if the IVL control system determines that the predetermined number of voltage pulses have been generated, then no further voltage pulses are executed.

8. The intravascular lithotripsy system of any one of embodiments 1-7, wherein the IVL control system is configured to define an acceptable voltage magnitude window comprising the predetermined lower voltage magnitude threshold and the predetermined upper voltage magnitude threshold.

9. The intravascular lithotripsy system, wherein the acceptable voltage magnitude window is different for balloons of different outer diameters.

10. The intravascular lithotripsy system of embodiment 9, wherein the predetermined lower voltage magnitude threshold is about 2500V for balloons having an outer diameter of 2.5 mm.

11. The intravascular lithotripsy system of embodiment 9, wherein the predetermined lower voltage magnitude threshold comprises about 2500V for balloons having an outer diameter of 3.0 mm.

12. The intravascular lithotripsy system of embodiment 9, wherein the predetermined lower voltage magnitude threshold comprises about 2500V for balloons having an outer diameter of 3.5 mm.

13. The intravascular lithotripsy system of embodiment 9, wherein the predetermined lower voltage magnitude threshold comprises about 2500V for balloons having an outer diameter of 4.0 mm.

14. The intravascular lithotripsy system of embodiment 9, wherein the predetermined lower voltage magnitude threshold is about 3000V for balloons having an outer diameter of 2.5 mm.

15. The intravascular lithotripsy system of embodiment 9, wherein the predetermined lower voltage magnitude threshold comprises about 3000V for balloons having an outer diameter of 3.0 mm.

16. The intravascular lithotripsy system of embodiment 9, wherein the predetermined lower voltage magnitude threshold comprises about 3000V for balloons having an outer diameter of 3.5 mm.

17. The intravascular lithotripsy system of embodiment 9, wherein the predetermined lower voltage magnitude threshold comprises about 3000V for balloons having an outer diameter of 4.0 mm.

18. The intravascular lithotripsy system of embodiment 9, wherein the predetermined lower voltage magnitude threshold is less than about 3000V for balloons having an outer diameter of 2.0 mm.

19. The intravascular lithotripsy system of embodiment 9, wherein the predetermined upper voltage magnitude threshold is less than about 3000V for balloons having an outer diameter of 2.5 mm.

20. The intravascular lithotripsy system of embodiment 9, wherein the predetermined lower voltage magnitude threshold is less than about 3000V for balloons having an outer diameter of 3.0 mm.

21. The intravascular lithotripsy system of embodiment 9, wherein the predetermined lower voltage magnitude threshold is less than about 3000V for balloons having an outer diameter of 3.5 mm.

22. The intravascular lithotripsy system of embodiment 9, wherein the predetermined lower voltage magnitude threshold is less than about 3000V for balloons having an outer diameter of 4.0 mm.

23. The intravascular lithotripsy system of embodiment 9, wherein the predetermined upper voltage magnitude threshold is greater than about 3000V for balloons having an outer diameter of 2.5 mm.

24. The intravascular lithotripsy system of embodiment 9, wherein the predetermined lower voltage magnitude threshold is greater than about 3000V for balloons having an outer diameter of 3.0 mm.

25. The intravascular lithotripsy system of embodiment 9, wherein the predetermined lower voltage magnitude threshold is greater than about 3000V for balloons having an outer diameter of 3.5 mm.

26. The intravascular lithotripsy system of embodiment 9, wherein the predetermined lower voltage magnitude threshold is greater than about 3000V for balloons having an outer diameter of 4.0 mm.

27. The intravascular lithotripsy system of any one of embodiments 9 to 26, wherein the predetermined upper voltage magnitude threshold is greater than about 3250V for balloons having an outer diameter of 2.5 mm.

28. The intravascular lithotripsy system of any one of embodiments 9 to 26, wherein the predetermined upper voltage magnitude threshold is greater than about 3250V for balloons having an outer diameter of 3.0 mm.

29. The intravascular lithotripsy system of any one of embodiments 9-26, wherein the predetermined upper voltage magnitude threshold is greater than about 3250V for balloons having an outer diameter of 3.5 mm.

30. The intravascular lithotripsy system of any one of embodiments 9-26, wherein the predetermined upper voltage magnitude threshold is greater than about 3250V for balloons having an outer diameter of 4.0 mm.

31. The intravascular lithotripsy system of any one of the embodiments 1-30, wherein the IVL control system is configured to determine whether the target voltage is not at the predetermined upper voltage magnitude target for a prior executed series of voltage pulses, and to increase the target voltage magnitude by a predetermined amount when the target voltage is determined to not be at the predetermined upper voltage magnitude target.

32. The intravascular lithotripsy system of embodiment 31, wherein the predetermined amount of voltage magnitude increase is within the range of 1 to 250V.

33. The intravascular lithotripsy system of any one of the embodiments 1-32, wherein the target voltage magnitude is increased by 25V when the target voltage is not at the predetermined upper voltage magnitude target for a prior executed series of voltage pulses.

34. The intravascular lithotripsy system of any one of the embodiments 1-32, wherein the target voltage magnitude is increased by more than 25V when the target voltage is not at the predetermined upper voltage magnitude target for a prior executed series of voltage pulses.

35. The intravascular lithotripsy system of any one of the embodiments 1-32, wherein the target voltage magnitude is increased by less than 25V when the target voltage is not at the predetermined upper voltage magnitude target for a prior executed voltage pulse.

36. The intravascular lithotripsy system of any one of the embodiments 1-32, wherein the target voltage magnitude is increased by 25V when the target voltage is not at the predetermined upper voltage magnitude target for a prior executed voltage pulse.

37. The intravascular lithotripsy system of any one of the embodiments 1-32, wherein the target voltage magnitude is increased by more than 25V when the target voltage is not at the predetermined upper voltage magnitude target for a prior executed voltage pulse.

38. The intravascular lithotripsy system of any one of the embodiments 1-32, wherein the target voltage magnitude is increased by less than 25V when the target voltage is not at the predetermined upper voltage magnitude target for a prior executed voltage pulse.

39. The intravascular lithotripsy system of any of the embodiments 1-38, wherein the pressure output over the predetermined maximum number of voltage pulses does not decay or decrease on average more than 0.25 Mpa.

40. The intravascular lithotripsy system of any of the embodiments 1-38, wherein the pressure output across a range of 10 to 300 voltage pulses does not decay or decrease on average more than 0.25 MPa.

41. The intravascular lithotripsy system of any of the embodiments 1-38, wherein the pressure output of the last voltage pulse of the predetermined maximum number of voltage pulses is greater than the pressure output of the first voltage pulse.

42. The intravascular lithotripsy system of any of the embodiments 1-41, wherein a slope of the pressure output of the voltage pulses increases over time.

43. The intravascular lithotripsy system of any of the embodiments 1-40, wherein a slope of the pressure output of the voltage pulses decreases over time.

44. The intravascular lithotripsy system of any of the embodiments 1-40, wherein a slope of the pressure output of the voltage pulses indicates a constant pressure magnitude output across the voltage pulses.

45. The intravascular lithotripsy system of any of the embodiments 1-44, wherein a plurality of a series of voltage pulses are generated.

46. The intravascular lithotripsy system of any of the embodiments 1-45, wherein one or more of the series of voltage pulses comprises 10 voltage pulses.

47. The intravascular lithotripsy system of any of the embodiments 1-45, wherein one or more of the series of voltage pulses comprises more than 10 voltage pulses.

48. The intravascular lithotripsy system of any of the embodiments 1-45, wherein one or more of the series of voltage pulses comprises less than 10 voltage pulses.

49. A method for generating and controlling voltage pulses, comprising:

providing a device according to any one of the embodiments 1-48;

determining the outer diameter of the device's balloon;

establishing an acceptable voltage pulse window comprising a predetermined lower voltage magnitude threshold and a predetermined upper voltage magnitude threshold;

executing a first series of voltage pulses at the predetermined lower voltage magnitude threshold;

increasing the voltage magnitude target by a predetermined amount and execute another series of voltage pulses at the increased voltage magnitude target;

continuing to sequentially increase the voltage magnitude target and executing of a related series of voltage pulses at the sequentially increased voltage magnitude target until the voltage magnitude target equals the predetermined upper voltage magnitude threshold;

determining that a predetermined number of voltage pulses have not been executed; and continuing executing one or more series of voltage pulses at the upper voltage magnitude threshold until it is determined that predetermined number of voltage pulses have been executed; and stopping the executing of the voltage pulses.

50. A method for generating and controlling voltage pulses, comprising:

providing a device according to any one of the embodiments 1-48;

determining the outer diameter of the device's balloon;

establishing an acceptable voltage pulse window comprising a predetermined lower voltage magnitude threshold and a predetermined upper voltage magnitude threshold;

executing a first series of voltage pulses at the predetermined lower voltage magnitude threshold;

increasing the voltage magnitude target by a predetermined amount and execute another series of voltage pulses at the increased voltage magnitude target;

continuing to sequentially increase the voltage magnitude target and executing of a related series of voltage pulses at the sequentially increased voltage magnitude target until the voltage magnitude target equals the predetermined upper voltage magnitude threshold;

determining that a predetermined number of voltage pulses have been executed; and stopping the executing of the voltage pulses.

51. A method for generating and controlling voltage pulses that produce pressure output that is stable and substantially constant, comprising:

providing a device according to any one of the embodiments 1-48;

determining the outer diameter of the device's balloon;

establishing an acceptable voltage pulse window comprising a predetermined lower voltage magnitude threshold and a predetermined upper voltage magnitude threshold;

executing a first series of voltage pulses at the predetermined lower voltage magnitude threshold;

increasing the voltage magnitude target by a predetermined amount and execute another series of voltage pulses at the increased voltage magnitude target;

continuing to sequentially increase the voltage magnitude target and executing of a related series of voltage pulses at the sequentially increased voltage magnitude target until the voltage magnitude target equals the predetermined upper voltage magnitude threshold; and producing a pressure output for each voltage pulse comprising a magnitude that is stable and substantially constant.

52. The method of embodiment 51, wherein the pressure output is generated over 10 to at least 300 voltage pulses.

53. A method for generating and controlling voltage pulses that produce pressure output that increases from the first voltage pulse to the last voltage pulse, comprising:

providing a device according to any one of the embodiments 1-48;

determining the outer diameter of the device's balloon;

establishing an acceptable voltage pulse window comprising a predetermined lower voltage magnitude threshold and a predetermined upper voltage magnitude threshold;

executing a first series of voltage pulses at the predetermined lower voltage magnitude threshold;

increasing the voltage magnitude target by a predetermined amount and execute another series of voltage pulses at the increased voltage magnitude target;

continuing to sequentially increase the voltage magnitude target and executing of a related series of voltage pulses at the sequentially increased voltage magnitude target until the voltage magnitude target equals the predetermined upper voltage magnitude threshold; and producing a pressure output for each voltage pulse comprising a magnitude that increases from the first voltage pulse to the last voltage pulse.

54. The method of embodiment 53, wherein the pressure output is generated over 10 to at least 300 voltage pulses.

55. The method of any one of embodiments 49-54, wherein the voltage pulses are generated at a frequency that is within the range of 1 to 5 pulses/second.

56. The method of embodiment 55, wherein the voltage pulse frequency comprises 2 pulses/second.

57. The method of embodiment 55, wherein the voltage pulse frequency comprises 3 pulses/second.

58. The method of any one of embodiments 49-57, wherein the pressure output of a first balloon comprising an outer diameter is not smaller than the pressure output of a second balloon comprising an outer diameter that is smaller than the outer diameter of the first balloon.

Exemplary Embodiment Set 2

1. An intravascular lithotripsy system with controlled stable and constant pressure output across a series of voltage pulses, comprising:

at least one set of spaced-apart electrodes for arrangement within a body lumen while disposed within a fluid-fillable member configured to contain conductive fluid therein;

an electric pulse generation system for providing electrical energy to the at least one set of spaced-apart electrodes to generate a plurality of pressure waves for intravascular lithotripsy (IVL) therapy, the electric pulse generation system including an IVL control system comprising a processor configured to execute instructions stored on a memory, and circuitry configured to communicate signals based on operation of the processor, the IVL control system configured to:

generate an initial plurality of voltage pulses comprising an initial series of voltage pulses to the at least one set of spaced-apart electrodes, wherein the magnitude of each voltage pulse in the initial series of voltage pulses comprises a target voltage that is initially set at a predetermined lower voltage magnitude threshold, wherein more than one of the generated plurality of voltage pulses produce a pressure wave, generate one or more subsequent series of voltage pulses, each subsequent series comprising a plurality of voltage pulses, wherein the target voltage for each subsequent series of voltage pulses is increased by a predetermined amount, wherein each one of the plurality of the produced pressure waves comprises a pressure magnitude output, and wherein the IVL control system is configured to control the pressure magnitude output for the plurality of pressure waves such that the pressure magnitude output does not decay or decrease on average more than a predetermined amount across the plurality of pressure waves.

2. An intravascular lithotripsy system with controlled stable and constant pressure output across a series of voltage pulses, comprising:

at least one set of spaced-apart electrodes for arrangement within a body lumen while disposed within a fluid-fillable member configured to contain conductive fluid therein;

an electric pulse generation system for providing electrical energy to the at least one set of electrode to generate a plurality of pressure waves for intravascular lithotripsy (IVL) therapy, the electric pulse generation system including an IVL control system comprising a processor configured to execute instructions stored on a memory, and circuitry configured to communicate signals based on operation of the processor, the IVL control system configured to:

generate an initial plurality of voltage pulses comprising an initial series of voltage pulses to the at least one set of spaced-apart electrodes, wherein the magnitude of each voltage pulse in the initial series of voltage pulses comprises a target voltage that is initially set at a predetermined lower voltage magnitude threshold, wherein more than one of the generated plurality of voltage pulses produce a pressure wave, generate one or more subsequent series of voltage pulses, each subsequent series comprising a plurality of voltage pulses, wherein the target voltage for each subsequent series of voltage pulses is increased by a predetermined amount, wherein each one of the plurality of the produced pressure waves comprises a pressure magnitude output, and wherein the IVL control system is configured to control the target voltage such that the pressure magnitude output does not decay or decrease on average more than a predetermined amount across the plurality of pressure waves.

3. A method for generating and controlling voltage pulses that produce controlled pressure output that is stable and substantially constant across a series of voltage pulses in an intravascular lithotripsy system, comprising:

providing an intravascular lithotripsy system according to embodiment 2;

determining the outer diameter of the intravascular lithotripsy system's balloon;

establishing an acceptable voltage pulse window comprising a predetermined lower voltage magnitude threshold and a predetermined upper voltage magnitude threshold;

executing a first series of voltage pulses at the predetermined lower voltage magnitude threshold;

increasing the voltage magnitude target by a predetermined amount and execute another series of voltage pulses at the increased voltage magnitude target;

continuing to sequentially increase the voltage magnitude target and executing of a related series of voltage pulses at the sequentially increased voltage magnitude target until the voltage magnitude target equals the predetermined upper voltage magnitude threshold; and producing a plurality of pressure waves, each pressure wave comprising a pressure output comprising a pressure magnitude that is controlled to not decay or decrease on average more than a predetermined amount across the plurality of pressure waves.

4. An intravascular lithotripsy system with controlled pressure output magnitude across a series of voltage pulses, comprising:

at least one set of spaced-apart electrodes for arrangement within a body lumen while disposed within a fluid-fillable member configured to contain conductive fluid therein;

an electric pulse generation system for providing electrical energy to the at least one set of spaced-apart electrodes to generate a plurality of pressure waves for intravascular lithotripsy (IVL) therapy, the electric pulse generation system including an IVL control system comprising a processor configured to execute instructions stored on a memory, and circuitry configured to communicate signals based on operation of the processor, the IVL control system configured to:

generate an initial plurality of voltage pulses comprising an initial series of voltage pulses to the at least one set of spaced-apart electrodes, wherein the magnitude of each voltage pulse in the initial series of voltage pulses comprises a target voltage that is initially set at a predetermined lower voltage magnitude threshold, wherein more than one of the generated plurality of voltage pulses produce a pressure wave, generate one or more subsequent series of voltage pulses, each subsequent series comprising a plurality of voltage pulses, wherein the target voltage for each subsequent series of voltage pulses is increased by a predetermined amount, wherein each one of the plurality of the produced pressure waves comprises a pressure magnitude output, and wherein the IVL control system is configured to control the pressure magnitude output within predetermined upper and lower threshold magnitudes across the plurality of pressure waves.

5. An intravascular lithotripsy system with controlled pressure output magnitude across a series of voltage pulses, comprising:

at least one set of spaced-apart electrodes for arrangement within a body lumen while disposed within a fluid-fillable member configured to contain conductive fluid therein;

an electric pulse generation system for providing electrical energy to the at least one set of spaced-apart electrodes to generate a plurality of pressure waves for intravascular lithotripsy (IVL) therapy, the electric pulse generation system including an IVL control system comprising a processor configured to execute instructions stored on a memory, and circuitry configured to communicate signals based on operation of the processor, the IVL control system configured to:

generate an initial plurality of voltage pulses comprising an initial series of voltage pulses to the at least one set of spaced-apart electrodes, wherein the magnitude of each voltage pulse in the initial series of voltage pulses comprises a target voltage that is initially set at a predetermined lower voltage magnitude threshold, wherein more than one of the generated plurality of voltage pulses produce a pressure wave, generate one or more subsequent series of voltage pulses, each subsequent series comprising a plurality of voltage pulses, wherein the target voltage for each subsequent series of voltage pulses is increased by a predetermined amount, wherein each one of the plurality of the produced pressure waves comprises a pressure magnitude output, and wherein the IVL control system is configured to control the target voltage within predetermined upper and lower thresholds, and further configured to control the resulting pressure wave output within predetermined upper and lower threshold magnitudes across the plurality of pressure waves.

6. A method for controlling pressure output magnitude across a series of voltage pulses generated by an intravascular lithotripsy system, comprising:

providing an intravascular lithotripsy system according to embodiment 5, wherein the fluid-filled member comprises a balloon;

determining the outer diameter of the intravascular lithotripsy system's balloon;

establishing an acceptable voltage pulse window comprising a predetermined lower voltage magnitude threshold and a predetermined upper voltage magnitude threshold;

executing a first series of voltage pulses at the predetermined lower voltage magnitude threshold;

increasing the voltage magnitude target by a predetermined amount and execute another series of voltage pulses at the increased voltage magnitude target;

continuing to sequentially increase the voltage magnitude target and executing of a related series of voltage pulses at the sequentially increased voltage magnitude target until the voltage magnitude target equals the predetermined upper voltage magnitude threshold; and producing a plurality of pressure waves, each pressure wave comprising a pressure output comprising a pressure magnitude that is controlled to not decay or decrease such that the pressure output across the plurality of pressure waves remains above a predetermined pressure magnitude.

7. An intravascular lithotripsy system with controlled pressure output across a plurality of voltage pulses, comprising:

at least one set of spaced-apart electrodes for arrangement within a body lumen while disposed within a fluid-fillable member configured to contain conductive fluid therein;

an electric pulse generation system for providing electrical energy to the at least one set of spaced-apart electrodes to generate a plurality of pressure waves for intravascular lithotripsy (IVL) therapy, the electric pulse generation system including an IVL control system comprising a processor configured to execute instructions stored on a memory, and circuitry configured to communicate signals based on operation of the processor, the IVL control system configured to:

generate an initial plurality of voltage pulses to the at least one set of electrodes, wherein the magnitude of each voltage pulse in the initial series of voltage pulses comprises a target voltage that is initially set at a predetermined lower voltage magnitude threshold, wherein more than one of the generated plurality of voltage pulses produce a pressure wave, determine that a predetermined maximum number of voltage pulses have not been executed, and when the predetermined maximum number of voltage pulses have been determined to not have been executed, sequentially increase the target voltage a predetermined amount and executing related series of voltage pulses until the target voltage is determined to meet a predetermined upper voltage threshold and/or the predetermined maximum number of voltage pulses is determined to have been executed, wherein each one of the plurality of the produced pressure waves comprises a pressure magnitude output, wherein the IVL control system is configured to control the pressure magnitude output within a predetermined upper and lower pressure magnitude threshold magnitudes across the plurality of pressure waves, and terminate the execution of voltage pulses when the predetermined maximum number of voltage pulses have been determined to have been executed.

8. A method for generating and controlling voltage pulses that produce controlled pressure output that is stable and substantially constant across a series of voltage pulses in an intravascular lithotripsy system, comprising:

providing an intravascular lithotripsy system according to embodiment 1, wherein the fluid-filled member comprises a balloon;

determining the outer diameter of the intravascular lithotripsy system's balloon;

establishing an acceptable voltage pulse window comprising a predetermined lower voltage magnitude threshold and a predetermined upper voltage magnitude threshold;

executing a first series of voltage pulses at the predetermined lower voltage magnitude threshold;

increasing the voltage magnitude target by a predetermined amount and execute another series of voltage pulses at the increased voltage magnitude target;

continuing to sequentially increase the voltage magnitude target and executing of a related series of voltage pulses at the sequentially increased voltage magnitude target until the voltage magnitude target equals the predetermined upper voltage magnitude threshold;

producing a plurality of pressure waves, each pressure wave comprising a pressure output comprising a pressure magnitude that is controlled within upper and lower pressure magnitude threshold magnitudes across the plurality of pressure waves;

determining that a predetermined maximum number of voltage pulses have been executed; and terminating the executing of the voltage pulses.

9. An intravascular lithotripsy system comprising controlled increasing pressure output, comprising:

at least one set of spaced-apart electrodes for arrangement within a body lumen while disposed within a fluid-fillable member configured to contain conductive fluid therein;

an electric pulse generation system for providing electrical energy to the at least one set of spaced-apart electrodes to generate a plurality of pressure waves for intravascular lithotripsy (IVL) therapy, the electric pulse generation system including an IVL control system comprising a processor configured to execute instructions stored on a memory, and circuitry configured to communicate signals based on operation of the processor, the IVL control system configured to:

generate an initial plurality of voltage pulses comprising an initial series of voltage pulses to the at least one set of spaced-apart electrodes, wherein the magnitude of each voltage pulse in the initial series of voltage pulses comprises a target voltage that is initially set at a predetermined lower voltage magnitude threshold, wherein more than one of the generated plurality of voltage pulses produce a pressure wave, generate one or more subsequent series of voltage pulses, each subsequent series comprising a plurality of voltage pulses, wherein the target voltage for each subsequent series of voltage pulses is increased by a predetermined amount, wherein each one of the plurality of the produced pressure waves comprises a pressure magnitude output, and wherein the IVL control system is configured to control the pressure magnitude output for the plurality of pressure waves such that the pressure magnitude output increases across the plurality of pressure waves.

10. An intravascular lithotripsy system comprising controlled increasing pressure output across a series of voltage pulses, comprising:

at least one set of electrodes for arrangement within a body lumen while disposed within a fluid-fillable member configured to contain conductive fluid therein;

an electric pulse generation system for providing electrical energy to the at least one set of spaced-apart electrodes to generate a plurality of pressure waves for intravascular lithotripsy (IVL) therapy, the electric pulse generation system including an IVL control system comprising a processor for executing instructions stored on a memory, and circuitry configured for communication of signals based on operation of the processor, the IVL control system configured to:

generate an initial plurality of voltage pulses comprising an initial series of voltage pulses to the at least one set of spaced-apart electrodes, wherein the magnitude of each voltage pulse in the initial series of voltage pulses comprises a target voltage that is initially set at a predetermined lower voltage magnitude threshold, wherein more than one of the generated plurality of voltage pulses produce a pressure wave, generate one or more subsequent series of voltage pulses, each subsequent series comprising a plurality of voltage pulses, wherein the target voltage for each subsequent series of voltage pulses is increased by a predetermined amount, wherein each one of the plurality of the produced pressure waves comprises a pressure magnitude output, and wherein the IVL control system is configured to control the target voltage such that the pressure magnitude output is controlled to increase within a predetermined pressure magnitude window across the plurality of pressure waves.

11. A method for generating and controlling voltage pulses that produce controlled increasing pressure output in an intravascular lithotripsy system, comprising:

providing an intravascular lithotripsy system according to embodiment 2, wherein the fluid-filled member comprises a balloon;

determining the outer diameter of the intravascular lithotripsy system's balloon;

establishing an acceptable voltage pulse window comprising a predetermined lower voltage magnitude threshold and a predetermined upper voltage magnitude threshold;

executing a first series of more than one voltage pulses at the predetermined lower voltage magnitude threshold;

increasing the voltage magnitude target by a predetermined amount and execute another series of voltage pulses at the increased voltage magnitude target;

continuing to sequentially increase the voltage magnitude target and executing of a related series of voltage pulses at the sequentially increased voltage magnitude target until the voltage magnitude target equals the predetermined upper voltage magnitude threshold; and producing a plurality of pressure waves, each pressure wave comprising a pressure output comprising a pressure magnitude that is controlled to increase across the plurality of pressure waves.

12. An intravascular lithotripsy system producing controlled decreasing pressure output, comprising:

at least one set of spaced-apart electrodes for arrangement within a body lumen while disposed within a fluid-fillable member configured to contain conductive fluid therein;

an electric pulse generation system for providing electrical energy to the at least one set of spaced-apart electrodes to generate a plurality of pressure waves for intravascular lithotripsy (IVL) therapy, the electric pulse generation system including an IVL control system comprising a processor configured to execute instructions stored on a memory, and circuitry configured to communicate signals based on operation of the processor, the IVL control system configured to:

generate an initial plurality of voltage pulses comprising an initial series of voltage pulses to the at least one set of spaced-apart electrodes, wherein the magnitude of each voltage pulse in the initial series of voltage pulses comprises a target voltage that is initially set at a predetermined lower voltage magnitude threshold, wherein more than one of the generated plurality of voltage pulses produce a pressure wave, generate one or more subsequent series of voltage pulses, each subsequent series comprising a plurality of voltage pulses, wherein the target voltage for each subsequent series of voltage pulses is increased by a predetermined amount, wherein each one of the plurality of the produced pressure waves comprises a pressure magnitude output, and wherein the IVL control system is configured to control the pressure magnitude output for the plurality of pressure waves such that the pressure magnitude output decays or decreases within a predetermined pressure magnitude window across the plurality of pressure waves.

13. An intravascular lithotripsy system producing controlled decreasing pressure output across a series of voltage pulses, comprising:

at least one set of spaced-apart electrodes for arrangement within a body lumen while disposed within a fluid-fillable member configured to contain conductive fluid therein;

an electric pulse generation system for providing electrical energy to the at least one set of spaced-apart electrodes to generate a plurality of pressure waves for intravascular lithotripsy (IVL) therapy, the electric pulse generation system including an IVL control system comprising a processor for executing instructions stored on a memory, and circuitry configured for communication of signals based on operation of the processor, the IVL control system configured to:

generate an initial plurality of voltage pulses comprising an initial series of voltage pulses to the at least one set of electrodes, wherein the magnitude of each voltage pulse in the initial series of voltage pulses comprises a target voltage that is initially set at a predetermined lower voltage magnitude threshold, wherein more than one of the generated plurality of voltage pulses produce a pressure wave, generate one or more subsequent series of voltage pulses, each subsequent series comprising a plurality of voltage pulses, wherein the target voltage for each subsequent series of voltage pulses is increased by a predetermined amount, wherein each one of the plurality of the produced pressure waves comprises a pressure magnitude output, and wherein the IVL control system is configured to control the target voltage such that the pressure magnitude output decreases within a predetermined pressure magnitude window across the plurality of pressure waves.

14. A method for generating and controlling voltage pulses that produce controlled decreasing pressure output in an intravascular lithotripsy system, comprising:

providing an intravascular lithotripsy system according to embodiment 2, wherein the fluid-filled member comprises a balloon;

determining the outer diameter of the intravascular lithotripsy system's balloon;

establishing an acceptable voltage pulse window comprising a predetermined lower voltage magnitude threshold and a predetermined upper voltage magnitude threshold;

executing a first series of more than one voltage pulses at the predetermined lower voltage magnitude threshold;

increasing the voltage magnitude target by a predetermined amount and execute another series of voltage pulses at the increased voltage magnitude target;

continuing to sequentially increase the voltage magnitude target and executing of a related series of voltage pulses at the sequentially increased voltage magnitude target until the voltage magnitude target equals the predetermined upper voltage magnitude threshold; and producing a plurality of pressure waves, each pressure wave comprising a pressure output comprising a pressure magnitude that is controlled to decrease within a predetermined pressure magnitude window across the plurality of pressure waves.

Exemplary Embodiment Set 3

1. An IVL system comprising at least one set of spaced-apart electrodes for arrangement within a body lumen while disposed within a fluid-fillable member configured to contain conductive fluid therein;

an electric pulse generation system for providing electrical energy to the at least one set of spaced-apart electrodes to generate a plurality of pressure waves for intravascular lithotripsy (IVL) therapy, the electric pulse generation system including an IVL control system comprising a processor for executing instructions stored on a memory, and circuitry configured for communication of signals based on operation of the processor, the IVL control system configured to:

generate an initial plurality of voltage pulses comprising at least an initial series of voltage pulses to the at least one set of electrodes, wherein the magnitude of each voltage pulse in the initial series of voltage pulses comprises a target voltage that is initially set at a predetermined lower voltage magnitude threshold, wherein more than one of the generated plurality of voltage pulses produce a pressure wave, wherein the IVL control system is configured to control the pressure magnitude output across the plurality of pressure waves.

2. The IVL system of embodiment 1, wherein the IVL control system is configured to control the pressure magnitude output is controlled to not decay or decrease more than a predetermined amount across the plurality of pressure waves.

3. The IVL system of embodiment 2, wherein the IVL control system is configured to control the target voltage within predetermined upper and lower thresholds.

4. The IVL system of embodiment 1, wherein the IVL control system is configured to control the pressure magnitude output to remain above a predetermined lower threshold across the plurality of pressure waves.

5. The IVL system of embodiment 4, wherein the IVL control system is configured to control the target voltage within predetermined upper and lower thresholds.

6. The IVL system of embodiment 1, wherein the IVL control system is configured to control the pressure magnitude output to remain within predetermined upper and lower thresholds across the plurality of pressure waves.

7. The IVL system of embodiment 6, wherein the IVL control system is configured to control the target voltage within predetermined upper and lower thresholds.

8. The IVL system of embodiment 1, wherein the IVL control system is configured to control the pressure magnitude output to remain at a substantially constant magnitude across the plurality of pressure waves.

9. The IVL system of embodiment 8, wherein the IVL control system is configured to control the target voltage within predetermined upper and lower thresholds.

10. The IVL system of embodiment 1, wherein the IVL control system is configured to control the pressure magnitude output is controlled to not increase more than a predetermined amount across the plurality of pressure waves.

11. The IVL system of embodiment 10, wherein the IVL control system is configured to control the target voltage within predetermined upper and lower thresholds.

12. The IVL system of embodiment 1, wherein the IVL control system is further configured to terminate the execution of voltage pulses when the predetermined maximum number of voltage pulses have been determined to be executed.

Exemplary Embodiment Set 4

1. An intravascular lithotripsy system comprising:
- at least one set of electrodes for arrangement within a body lumen while disposed within a fluid-fillable member configured to contain conductive fluid therein;
- an electric pulse generation system for providing electrical energy to the at least one set of electrode to generate spark for intravascular lithotripsy (IVL) therapy, the electric pulse generation system including an IVL control system comprising a processor for executing instructions stored on a memory, and circuitry configured for communication of signals based on operation of the processor, the IVL control system configured to:
- generate an initial series of voltage pulses to the at least one set of electrodes, wherein the magnitude of each voltage pulse in the initial series of voltage pulses comprises a target voltage that is set at a predetermined lower voltage magnitude threshold,
- determine whether a threshold parameter is achieved, and
- responsive to determination that the threshold parameter is not achieved, increase the voltage magnitude by a predetermined amount, and
- generate another series of voltage pulses at the increased voltage magnitude for application to the at least one set of electrodes.

2. The intravascular lithotripsy system of embodiment 1, wherein the IVL control system is configured to continue to determine whether a threshold parameter is achieved after each generated series of voltage pulses.

3. The intravascular lithotripsy system of embodiment 2, wherein the threshold parameter comprises a predetermined upper voltage magnitude threshold.

4. The intravascular lithotripsy system of embodiment 3, wherein the IVL control system is configured to determine if the number of voltage pulses generated does not exceed a predetermined maximum number of voltage pulses.

5. The intravascular lithotripsy system of embodiment 3, wherein the predetermined maximum number of voltage pulses is within a range of 10 to 300 voltage pulses.

6. The intravascular lithotripsy system of embodiment 4, wherein if the IVL control system is configured to determine that the predetermined number of voltage pulses have not been generated, and if the predetermined number of voltage pulses have not been generated, then the IVL control system is further configured to execute another series of voltage pulses at the predetermined upper voltage magnitude threshold.

7. The intravascular lithotripsy system of embodiment 4, wherein if the IVL control system determines that the predetermined number of voltage pulses have been generated, then no further voltage pulses are executed.

8. The intravascular lithotripsy system of any one of embodiments 1-7, wherein the IVL control system is configured to define an acceptable voltage magnitude window comprising the predetermined lower voltage magnitude threshold and the predetermined upper voltage magnitude threshold.

9. The intravascular lithotripsy system of embodiment 8, wherein the acceptable voltage magnitude window is different for balloons of different outer diameters.

10. The intravascular lithotripsy system of embodiment 9, wherein the predetermined lower voltage magnitude threshold is about 2500V for balloons having an outer diameter of 2.5 mm.

11. The intravascular lithotripsy system of embodiment 9, wherein the predetermined lower voltage magnitude threshold comprises about 2500V for balloons having an outer diameter of 3.0 mm.

12. The intravascular lithotripsy system of embodiment 9, wherein the predetermined lower voltage magnitude threshold comprises about 2500V for balloons having an outer diameter of 3.5 mm.

13. The intravascular lithotripsy system of embodiment 9, wherein the predetermined lower voltage magnitude threshold comprises about 2500V for balloons having an outer diameter of 4.0 mm.

14. The intravascular lithotripsy system of embodiment 9, wherein the predetermined lower voltage magnitude threshold is about 3000V for balloons having an outer diameter of 2.5 mm.

15. The intravascular lithotripsy system of embodiment 9, wherein the predetermined lower voltage magnitude threshold comprises about 3000V for balloons having an outer diameter of 3.0 mm.

16. The intravascular lithotripsy system of embodiment 9, wherein the predetermined lower voltage magnitude threshold comprises about 3000V for balloons having an outer diameter of 3.5 mm.

17. The intravascular lithotripsy system of embodiment 9, wherein the predetermined lower voltage magnitude threshold comprises about 3000V for balloons having an outer diameter of 4.0 mm.

18. The intravascular lithotripsy system of embodiment 9, wherein the predetermined lower voltage magnitude threshold is less than about 3000V for balloons having an outer diameter of 2.0 mm.

19. The intravascular lithotripsy system of embodiment 9, wherein the predetermined upper voltage magnitude threshold is less than about 3000V for balloons having an outer diameter of 2.5 mm.

20. The intravascular lithotripsy system of embodiment 9, wherein the predetermined lower voltage magnitude threshold is less than about 3000V for balloons having an outer diameter of 3.0 mm.

21. The intravascular lithotripsy system of embodiment 9, wherein the predetermined lower voltage magnitude threshold is less than about 3000V for balloons having an outer diameter of 3.5 mm.

22. The intravascular lithotripsy system of embodiment 9, wherein the predetermined lower voltage magnitude threshold is less than about 3000V for balloons having an outer diameter of 4.0 mm.

23. The intravascular lithotripsy system of embodiment 9, wherein the predetermined upper voltage magnitude threshold is greater than about 3000V for balloons having an outer diameter of 2.5 mm.

24. The intravascular lithotripsy system of embodiment 9, wherein the predetermined lower voltage magnitude threshold is greater than about 3000V for balloons having an outer diameter of 3.0 mm.

25. The intravascular lithotripsy system of embodiment 9, wherein the predetermined lower voltage magnitude threshold is greater than about 3000V for balloons having an outer diameter of 3.5 mm.

26. The intravascular lithotripsy system of embodiment 9, wherein the predetermined lower voltage magnitude threshold is greater than about 3000V for balloons having an outer diameter of 4.0 mm.

27. The intravascular lithotripsy system of any one of embodiments 9 to 26, wherein the predetermined upper voltage magnitude threshold is greater than about 3250V for balloons having an outer diameter of 2.5 mm.

28. The intravascular lithotripsy system of any one of embodiments 9 to 26, wherein the predetermined upper voltage magnitude threshold is greater than about 3250V for balloons having an outer diameter of 3.0 mm.

29. The intravascular lithotripsy system of any one of embodiments 9-26, wherein the predetermined upper voltage magnitude threshold is greater than about 3250V for balloons having an outer diameter of 3.5 mm.

30. The intravascular lithotripsy system of any one of embodiments 9-26, wherein the predetermined upper voltage magnitude threshold is greater than about 3250V for balloons having an outer diameter of 4.0 mm.

31. The intravascular lithotripsy system of any one of the embodiments 1-30, wherein the IVL control system is configured to determine whether the target voltage is not at the predetermined upper voltage magnitude target for a prior executed series of voltage pulses, and to increase the target voltage magnitude by a predetermined amount when the target voltage is determined to not be at the predetermined upper voltage magnitude target.

32. The intravascular lithotripsy system of embodiment 31, wherein the predetermined amount of voltage magnitude increase is within the range of 1 to 250V.

33. The intravascular lithotripsy system of any one of the embodiments 1-32, wherein the target voltage magnitude is increased by 25V when the target voltage is not at the predetermined upper voltage magnitude target for a prior executed series of voltage pulses.

34. The intravascular lithotripsy system of any one of the embodiments 1-32, wherein the target voltage magnitude is increased by more than 25V when the target voltage is not at the predetermined upper voltage magnitude target for a prior executed series of voltage pulses.

35. The intravascular lithotripsy system of any one of the embodiments 1-32, wherein the target voltage magnitude is increased by less than 25V when the target voltage is not at the predetermined upper voltage magnitude target for a prior executed voltage pulse.

36. The intravascular lithotripsy system of any one of the embodiments 1-32, wherein the target voltage magnitude is increased by 25V when the target voltage is not at the predetermined upper voltage magnitude target for a prior executed voltage pulse.

37. The intravascular lithotripsy system of any one of the embodiments 1-32, wherein the target voltage magnitude is increased by more than 25V when the target voltage is not at the predetermined upper voltage magnitude target for a prior executed voltage pulse.

38. The intravascular lithotripsy system of any one of the embodiments 1-32, wherein the target voltage magnitude is increased by less than 25V when the target voltage is not at the predetermined upper voltage magnitude target for a prior executed voltage pulse.

39. The intravascular lithotripsy system of any of the embodiments 1-38, wherein the pressure output over the predetermined maximum number of voltage pulses does not decay or decrease on average more than 0.25 Mpa.

40. The intravascular lithotripsy system of any of the embodiments 1-38, wherein the pressure output across a range of 10 to 300 voltage pulses does not decay or decrease on average more than 0.25 MPa.

41. The intravascular lithotripsy system of any of the embodiments 1-38, wherein the pressure output of the last voltage pulse of the predetermined maximum number of voltage pulses is greater than the pressure output of the first voltage pulse.

42. The intravascular lithotripsy system of any of the embodiments 1-41, wherein a slope of the pressure output of the voltage pulses increases over time.

43. The intravascular lithotripsy system of any of the embodiments 1-40, wherein a slope of the pressure output of the voltage pulses decreases over time.

44. The intravascular lithotripsy system of any of the embodiments 1-40, wherein a slope of the pressure output of the voltage pulses indicates a constant pressure magnitude output across the voltage pulses.

45. The intravascular lithotripsy system of any of the embodiments 1-44, wherein a plurality of a series of voltage pulses are generated.

46. The intravascular lithotripsy system of any of the embodiments 1-45, wherein one or more of the series of voltage pulses comprises 10 voltage pulses.

47. The intravascular lithotripsy system of any of the embodiments 1-45, wherein one or more of the series of voltage pulses comprises more than 10 voltage pulses.

48. The intravascular lithotripsy system of any of the embodiments 1-45, wherein one or more of the series of voltage pulses comprises less than 10 voltage pulses.

49. A method for generating and controlling voltage pulses, comprising:

- providing a device according to any one of the embodiments 1-48, wherein the fluid-fillable member comprises a balloon;
- determining the outer diameter of the device's balloon;
- establishing an acceptable voltage pulse window comprising a predetermined lower voltage magnitude threshold and a predetermined upper voltage magnitude threshold;
- executing a first series of voltage pulses at the predetermined lower voltage magnitude threshold;
- increasing the voltage magnitude target by a predetermined amount and execute another series of voltage pulses at the increased voltage magnitude target;
- continuing to sequentially increase the voltage magnitude target and executing of a related series of voltage pulses at the sequentially increased voltage magnitude target until the voltage magnitude target equals the predetermined upper voltage magnitude threshold;

determining that a predetermined number of voltage pulses have not been executed; and continuing executing one or more series of voltage pulses at the upper voltage magnitude threshold until it is determined that predetermined number of voltage pulses have been executed; and stopping the executing of the voltage pulses.

50. A method for generating and controlling voltage pulses, comprising:

providing a device according to any one of the embodiments 1-48, wherein the fluid-fillable member comprises a balloon;

determining the outer diameter of the device's balloon;

establishing an acceptable voltage pulse window comprising a predetermined lower voltage magnitude threshold and a predetermined upper voltage magnitude threshold;

executing a first series of voltage pulses at the predetermined lower voltage magnitude threshold;

increasing the voltage magnitude target by a predetermined amount and execute another series of voltage pulses at the increased voltage magnitude target;

continuing to sequentially increase the voltage magnitude target and executing of a related series of voltage pulses at the sequentially increased voltage magnitude target until the voltage magnitude target equals the predetermined upper voltage magnitude threshold;

determining that a predetermined number of voltage pulses have been executed; and stopping the executing of the voltage pulses.

51. A method for generating and controlling voltage pulses that produce pressure output that is stable and substantially constant, comprising:

providing a device according to any one of the embodiments 1-48, wherein the fluid-fillable member comprises a balloon;

determining the outer diameter of the device's balloon;

establishing an acceptable voltage pulse window comprising a predetermined lower voltage magnitude threshold and a predetermined upper voltage magnitude threshold;

executing a first series of voltage pulses at the predetermined lower voltage magnitude threshold;

increasing the voltage magnitude target by a predetermined amount and execute another series of voltage pulses at the increased voltage magnitude target;

continuing to sequentially increase the voltage magnitude target and executing of a related series of voltage pulses at the sequentially increased voltage magnitude target until the voltage magnitude target equals the predetermined upper voltage magnitude threshold; and producing a pressure output for each voltage pulse comprising a magnitude that is stable and substantially constant.

52. The method of embodiment 51, wherein the pressure output is generated over 10 to at least 300 voltage pulses.

53. A method for generating and controlling voltage pulses that produce pressure output that increases from the first voltage pulse to the last voltage pulse, comprising:

providing a device according to any one of the embodiments 1-48, wherein the fluid-fillable member comprises a balloon;

determining the outer diameter of the device's balloon;

establishing an acceptable voltage pulse window comprising a predetermined lower voltage magnitude threshold and a predetermined upper voltage magnitude threshold;

executing a first series of voltage pulses at the predetermined lower voltage magnitude threshold;

increasing the voltage magnitude target by a predetermined amount and execute another series of voltage pulses at the increased voltage magnitude target;

continuing to sequentially increase the voltage magnitude target and executing of a related series of voltage pulses at the sequentially increased voltage magnitude target until the voltage magnitude target equals the predetermined upper voltage magnitude threshold; and producing a pressure output for each voltage pulse comprising a magnitude that increases from the first voltage pulse to the last voltage pulse.

54. The method of embodiment 53, wherein the pressure output is generated over 10 to at least 300 voltage pulses.

55. The method of any one of embodiments 49-54, wherein the voltage pulses are generated at a frequency that is within the range of 1 to 5 pulses/second.

56. The method of embodiment 55, wherein the voltage pulse frequency comprises 2 pulses/second.

57. The method of embodiment 55, wherein the voltage pulse frequency comprises 3 pulses/second.

58. The method of any one of embodiments 49-57, wherein the pressure output of a first balloon comprising an outer diameter is not smaller than the pressure output of a second balloon comprising an outer diameter that is smaller than the outer diameter of the first balloon.

Exemplary Embodiment Set 5

1. An intravascular lithotripsy system comprising:

a catheter assembly comprising an elongate member defining a lumen and while disposed within a fluid-fillable member configured to contain conductive fluid therein located on a longitudinal region of the elongate member, the catheter assembly configured to inflate the fluid-fillable with the conductive fluid to facilitate IVL therapy; and at least one set of spaced-apart electrodes for arrangement within the fluid-fillable member for submerging within the IVL fluid medium;

wherein the IVL control system is configured to apply one or more voltage pulses to the at least one spaced-apart electrodes under initial control settings, to determine whether a threshold parameter comprising the maximum number of voltage pulses resulting in an electrical arc between the at least one set of spaced-apart electrodes is achieved under the initial control settings, and to increase at least one of pulse duration and voltage in response to determination that the threshold parameter is not achieved, wherein the IVL control system is configured to apply the increased at least one of pulse duration and voltage to the at least one set of spaced-apart electrodes.

2. An intravascular lithotripsy system comprising a catheter assembly comprising an elongate member defining a lumen and while disposed within a fluid-fillable member configured to contain conductive fluid therein located on a longitudinal region of the elongate member, the catheter assembly configured to inflate the fluid-fillable with the conductive fluid to facilitate IVL therapy; at least one set of spaced-apart electrodes for arrangement within the fluid-fillable member for submerging within the conductive fluid; and an IVL control system comprising a processor for executing instructions stored on memory and circuitry configured to communicate signals based on operation of the processor for providing IVL therapy to a patient, wherein the IVL control system is configured to generate and apply one or more voltage pulses to the at least one spaced-apart electrodes under initial control settings, to determine whether a threshold parameter comprising the maximum number of voltage pulses resulting in an electrical arc between the at least one set of spaced-apart electrodes is achieved under the initial control settings, and to increase at least one of pulse duration and voltage in response to determination that the threshold parameter is not achieved, wherein the IVL control system is configured to apply the increased at least one of pulse duration and voltage to the at least one set of spaced-apart electrodes, and wherein the IVL control system is configured to continue reapplying the increase at least one of pulse duration and voltage to the at least one spaced-apart set of electrodes after the determination that the threshold parameter is not achieved, and to terminate the generation of voltage pulses when the determination is made that the threshold parameter is achieved.

3. A method of operating an intravascular lithotripsy (IVL) system having a catheter assembly comprising an elongate member defining a lumen and a fluid-fillable member configured to contain conductive fluid and located at a distal region of the elongate member, the catheter assembly configured to inflate the fluid-fillable member with the conductive fluid to facilitate IVL therapy, at least one set of spaced-apart electrodes for arrangement within the fluid-fillable member for submerging within the IVL fluid medium, and an IVL control system comprising a processor configured to execute instructions stored on memory and communications circuitry configured to communicate signals based on operation of the processor for providing IVL therapy to a patient, the method comprising:

generating voltage pulses and applying the generated voltage pulses under initial electrical settings comprising voltage magnitude and duration of application of generated voltage to the at least one set of spaced-apart electrodes;

determining whether a predetermined maximum number of electrical arcs produced between the at least one set of spaced-apart electrodes is achieved under the initial electrical settings;

increasing at least one of pulse duration and voltage of the electrical settings in response to determination that the threshold parameter is not achieved; and terminating the generating of the voltage pulses in response to determination that the threshold parameter is achieved.

4. An intravascular lithotripsy system comprising:

at least one set of spaced-apart electrodes for arrangement within a body lumen while disposed within a fluid-fillable member configured to contain a conductive fluid;

an electric pulse generation system for providing controlled levels of electrical energy to the at least one set of spaced-apart electrodes to generate spark for intravascular lithotripsy (IVL) therapy, the electric pulse generation system including an IVL control system comprising a processor configured to execute instructions stored on memory and communications circuitry configured to communicate signals based on commands from the processor, the IVL control system including a charge control system for controlling electrical charging of a discharge system, wherein the charge control system is configured to provide controlled and variable electrical power to the discharge system at different voltage level for consecutive cycles of charge.

5. An intravascular lithotripsy system comprising:

at least one set of spaced-apart electrodes for arrangement within a body lumen while disposed within a fluid-fillable member configured to contain a conductive fluid;

an electric pulse generation system configured to provide controlled electrical energy levels to the at least one set of spaced-apart electrodes to generate spark for intravascular lithotripsy (IVL) therapy, the electric pulse generation system including an IVL control system comprising a processor configured to execute instructions stored on memory and communications circuitry configured to communicate signals based on commands from the processor, the IVL control system including a charge control system for controlling electrical charging of a discharge system, wherein the discharge system includes an energy storage system and the charge control system is configured to provide controlled variable voltage power to the discharge system at different voltage for consecutive cycles of charge after energy discharge from the energy storage system.

6. An intravascular lithotripsy system comprising:

at least one set of spaced-apart electrodes for arrangement within a body lumen while disposed within a fluid-fillable member configured to contain a conductive fluid;

an electric pulse generation system for providing electrical energy to the at least one set of spaced-apart electrodes to generate spark for intravascular lithotripsy (IVL) therapy, the electric pulse generation system including an IVL control system comprising a processor configured to execute instructions stored on memory and communications circuitry configured to communicate signals based on commands from the processor, wherein the IVL control system is configured to:

assess the stored energy state of an energy storage system of the IVL system to determine stored energy;

compare the assessed stored energy state against a stored threshold value;

deliver a voltage pulse to at least one set of spaced-apart electrodes of the IVL system;

assess the remaining energy state of the energy storage system of the IVL system to determine remaining energy; and compare the assessed remaining energy state against a stored threshold value.

7. A method of operating an intravascular lithotripsy system, the method comprising:

assessing the stored energy state of an energy storage system of an intravascular lithotripsy (IVL) system to determine stored energy;

delivering a voltage pulse to at least one set of electrodes of the IVL system;

assessing the remaining energy state of the energy storage system of the IVL system to determine remaining energy; and comparing at least one of the assessed energy states with a stored threshold value to determine the energy of the voltage pulse.

8. A method of operating an intravascular lithotripsy system including at least one set of spaced-apart electrodes, the method comprising:

assessing the stored energy state of an energy storage system of an intravascular lithotripsy (IVL) system to determine stored energy;

delivering a voltage pulse to at least one of the at least one set of spaced-apart electrodes of the IVL system;

assessing the remaining energy state of the energy storage system of the IVL system to determine remaining energy; and comparing at least one of the assessed energy states with a stored threshold value to determine the energy of the voltage pulse, wherein assessing the energy state to determine stored energy includes determining a voltage level of the energy storage system.

9. An intravascular lithotripsy system comprising:

at least one set of spaced-apart electrodes for arrangement within a body lumen while disposed within a fluid-fillable member configured to contain a conductive fluid;

an electric pulse generation system for providing electrical energy to the at least one set of spaced-apart electrodes to generate spark for intravascular lithotripsy (IVL) therapy, the electric pulse generation system including an IVL control system comprising a processor configured to execute instructions stored on memory and communications circuitry configured to communicate signals based on commands from the processor, wherein the electric pulse generation system comprises an electrical power system including an AC mains and a DC power storage system, wherein the AC mains are configured for connection with a AC power receptacle to receive AC power from infrastructure, and the DC power storage system is configured to receive AC power from the AC mains and to convert AC power to DC power for charging a DC power storage device of the DC power storage system, and wherein the electric pulse generation system is configured to selectively provide power from the AC mains or the DC power storage system for IVL operations.

10. A method for powering a intravascular lithotripsy system, comprising:

providing the intravascular lithotripsy system of embodiment 1;

selecting provision of power from the AC mains; and powering the intravascular lithotripsy system 11. An intravascular lithotripsy system comprising:

at least one set of electrodes for arrangement within a body lumen while disposed within a fluid-fillable member configured to contain a conductive fluid;

an electric pulse generation system for providing electrical energy to the at least one set of spaced-apart electrodes to generate spark for intravascular lithotripsy (IVL) therapy, the electric pulse generation system including an IVL control system comprising a processor configured to execute instructions stored on memory and communications circuitry configured to communicate signals based on commands from the processor, wherein the IVL control system is configured to:

assess the stored energy state of an energy storage system of the IVL system to determine stored energy;

deliver a voltage pulse to at least one set of electrodes of the IVL system;

assess the remaining energy state of the energy storage system of the IVL system to determine remaining energy; and compare the assessed energy states to determine the energy of the voltage pulse.

12. A method of operating an intravascular lithotripsy system, the method comprising:

assessing the stored energy state of an energy storage system of an intravascular lithotripsy (IVL) system to determine stored energy;

delivering a voltage pulse to at least one set of spaced-apart electrodes of the IVL system;

assessing the remaining energy state of the energy storage system of the IVL system to determine remaining energy; and comparing the energy states assessed to determine the energy of the voltage pulse.

13. A method of operating an intravascular lithotripsy system, the method comprising:

assessing the stored energy state of an energy storage system of an intravascular lithotripsy (IVL) system to determine stored energy;

delivering a voltage pulse to at least one set of spaced-apart electrodes of the IVL system;

assessing the remaining energy state of the energy storage system of the IVL system to determine remaining energy; and comparing the energy states assessed to determine the energy of the voltage pulse, wherein assessing the energy state to determine stored energy includes determining a voltage level of the energy storage system.

14. An intravascular lithotripsy system comprising:

at least one set of spaced-apart electrodes for arrangement within a body lumen while disposed within a fluid-fillable member configured to contain a conductive fluid;

an electric pulse generation system for providing electrical energy to the at least one set of spaced-apart electrodes to generate spark for intravascular lithotripsy (IVL) therapy, the electric pulse generation system including an IVL control system comprising a processor configured to execute instructions stored on memory and communications circuitry configured to communicate signals based on commands from the processor, wherein the IVL control system including an adjustable energy storage system configured to selective adjust the electrical energy to be applied to the at least one set of spaced-apart electrodes for IVL therapy.

15. A method of operating an intravascular lithotripsy (IVL) system, the method comprising:

applying a voltage pulse to at least one set of electrodes;

determining to adjust a stored energy level of the IVL system;

applying another voltage pulse to the at least one set of electrodes using an energy level different from the voltage pulse.

Exemplary Embodiment Set 6

1. An intravascular lithotripsy system comprising:

at least one set of electrodes for arrangement within a body lumen while disposed within a fluid-fillable member configured to contain a conductive fluid;

an electric pulse generation system for providing electrical energy to the at least one set of electrode to generate spark for intravascular lithotripsy (IVL) therapy, the electric pulse generation system including an IVL control system comprising a processor for executing instructions stored on memory and circuitry configured for communication of signals based on operation of the processor, the IVL control system configured to:

apply initial electrical energy to the at least one set of electrodes, determine whether a threshold parameter is achieved, and responsive to determination that the threshold parameter is not achieved, increase a duration of a pulse of electrical energy for application to the at least one set of electrodes.

2. The system of embodiment 1, wherein the IVL control system is configured to re-apply initial electrical energy to the at least one set of electrodes, responsive to determination that the threshold parameter is achieved.

3. The system of embodiment 2, wherein the threshold parameter is a value of current for achieving sufficient spark for IVL therapy.

4. The system of embodiment 3, wherein the value of current is about 20 amperes.

5. The system of embodiment 1, wherein the IVL control system is configured to repeat applying of electrical energy to the at least set of electrodes with the increased duration of the pulse of electrical energy.

6. The system of embodiment 5, wherein the IVL control system is configured to determine whether the threshold parameter is achieved under the repeat applying of electrical energy.

7. The system of embodiment 6, wherein the IVL control system is configured to re-apply the electrical energy to the at least one set of electrodes with the increased duration of the pulse of electrical energy, responsive to determination that the threshold parameter is achieved under the repeat applying of electrical energy.

8. The system of embodiment 5, wherein the threshold parameter remains the same value under the initial applying and the repeat applying.

9. The system of embodiment 5, wherein the IVL control system is configured to determine whether a maximum duration is achieved.

10. The system of embodiment 9, wherein, responsive to determination that the maximum duration is achieved, the IVL control system is configured to increase the voltage of the electrical energy applied.

11. The system of embodiment 10, wherein the IVL control system is configured to re-apply the electrical energy to the at least one set of electrodes with the increased voltage.

12. The system of embodiment 10, wherein re-applying the electrical energy to the at least one set of electrodes with the increased voltage includes adjusting the duration as presently selected.

13. The system of embodiment 12, wherein adjusting the duration as presently selected includes reducing the duration.

14. The system of embodiment 13, wherein adjusting the duration as presently selected includes resetting the duration as presently selected equal to duration under the initial electrical energy.

15. The system of embodiment 10, wherein the IVL control system is configured to determine whether a maximum voltage is achieved, and to re-apply the electrical energy to the at least one set of electrodes with the increased voltage responsive to determination that the maximum voltage is not achieved.

16. The system of embodiment 9, wherein the maximum duration remains the same value under re-applying.

17. The system of embodiment 1, wherein applying of electrical energy comprises delivery of a voltage pulse having a voltage and duration.

18. The system of embodiment 17, wherein an initial duration of the initial electrical energy delivered to the at least one electrodes is a voltage pulse having duration within the range of about 0.1 microseconds to about 2 microseconds.

19. The system of embodiment 17, wherein an initial voltage of the initial electrical energy delivered to the at least one electrodes is a voltage pulse having voltage within the range of about 500 volts to about 4000 volts.

20. A method of operating an intravascular lithotripsy system, the method comprising:

applying initial electrical energy to at least one set of electrodes of an intravascular lithotripsy (IVL) system, wherein the at least one set of electrodes is submerged within a conductive fluid contained by a fluid-fillable member;

determining whether a threshold parameter is achieved; and responsive to determination that the threshold parameter is not achieved, increasing a duration of a pulse of electrical energy for application to the at least one set of electrodes.

21. The method of embodiment 20, further comprising re-applying initial electrical energy to the at least one set of electrodes, responsive to determination that the threshold parameter is achieved.

22. The method of embodiment 21, wherein the threshold parameter is a value of current for achieving sufficient spark for IVL therapy.

23. The method of embodiment 22, wherein the value of current is about 20 amperes.

24. The method of embodiment 20, further comprising repeating applying of electrical energy to the at least set of electrodes with the increased duration of the pulse of electrical energy.

25. The method of embodiment 24, further comprising determining whether the threshold parameter is achieved under the repeat applying of electrical energy.

26. The method of embodiment 25, further comprising re-applying the electrical energy to the at least one set of electrodes with the increased duration of the pulse of electrical energy, responsive to determination that the threshold parameter is achieved under the repeat applying of electrical energy.

27. The method of embodiment 25, wherein the threshold parameter remains the same value under the initial applying and the repeat applying.

28. The method of embodiment 25, further comprising determining whether a maximum duration is achieved.

29. The method of embodiment 28, further comprising increasing the voltage of the electrical energy applied, responsive to determination that the maximum duration is achieved.

30. The method of embodiment 29, further comprising re-applying the electrical energy to the at least one set of electrodes with the increased voltage.

31. The method of embodiment 30, wherein re-applying the electrical energy to the at least one set of electrodes with the increased voltage includes adjusting the duration as presently selected.

32. The method of embodiment 31, wherein adjusting the duration as presently selected includes reducing the duration.

33. The method of embodiment 32, wherein adjusting the duration as presently selected includes resetting the duration as presently selected equal to duration under the initial electrical energy.

34. The method of embodiment 29, further comprising determining whether a maximum voltage is achieved, re-applying the electrical energy to the at least one set of electrodes with the increased voltage responsive to determination that the maximum voltage is not achieved.

35. The method of embodiment 20, wherein applying of electrical energy comprises delivery of a voltage pulse having a voltage and duration.

36. The system of embodiment 35, wherein an initial duration of the initial electrical energy delivered to the at least one electrodes is a voltage pulse having duration within the range of about 0.1 microseconds to about 2 microseconds.

37. The system of embodiment 35, wherein an initial voltage of the initial electrical energy delivered to the at least one electrodes is a voltage pulse having voltage within the range of about 500 volts to about 4000 volts.

38. An intravascular lithotripsy system comprising a catheter assembly comprising an elongate member defining a lumen and a fluid-fillable member configured to contain a conductive fluid and located at or near a longitudinal end of the elongate member, the catheter assembly configured to fill the fluid-fillable member with the conductive fluid to facilitate IVL therapy;

at least one set of electrodes for arrangement within the fluid-fillable member for submerging the at least one set of electrodes within the conductive fluid;

an IVL therapy control system comprising a processor for executing instructions stored on memory and circuitry configured for communication of signals based on operation of the processor for providing IVL therapy to a patient, the IVL therapy control system configured to apply electrical energy having initial settings, to determine whether a threshold parameter is achieved under the electrical settings, and to increase at least one of pulse duration and voltage in response to determination that the threshold parameter is not achieved.

39. A method of operating an intravascular lithotripsy (IVL) system having a catheter assembly comprising an elongate member defining a lumen and a fluid-fillable member configured to contain a conductive fluid and located at or near a longitudinal end of the elongate member, the catheter assembly configured to inflate the fluid-fillable member with the conductive fluid to facilitate IVL therapy, at least one set of electrodes for arrangement within the fluid-fillable member for submerging within the IVL fluid medium, and an IVL therapy control system comprising a processor for executing instructions stored on memory and communications circuitry configured for communication of signals based on operation of the processor for providing IVL therapy to a patient, the method comprising:

applying electrical energy having electrical settings including initial settings;

determining whether a threshold parameter is achieved under the applied electrical settings; and increasing at least one of pulse duration and voltage of the electrical settings in response to determination that the threshold parameter is not achieved.

40. An intravascular lithotripsy system comprising:

at least one set of electrodes for arrangement within a body lumen while disposed within a fluid-fillable member configured to contain a conductive fluid;

an electric pulse generation system for providing electrical energy to the at least one set of electrode to generate spark for intravascular lithotripsy (IVL) therapy, the electric pulse generation system including an IVL control system comprising a processor for executing instructions stored on memory and communications circuitry configured for communication of signals based on commands from the processor, IVL control system including an adjustable energy storage system for selectively adjusting the stored energy applied for providing electrical energy to the at least one set of electrodes for IVL therapy.

41. The system of embodiment 40, wherein the electric pulse generation system includes a relay system for selectively connecting a number of energy storage elements of the energy storage system for discharge to provide electrical energy to the at least one set of electrodes.

42. The system of embodiment 41, wherein in an engaged arrangement of the relay system all of the number of energy storage elements are connected to discharge to provide electrical energy to the at least one set of electrodes.

43. The system of embodiment 42, wherein in a disengaged arrangement of the relay system fewer than all of the number of the energy storage elements are connected to discharge to provide electrical energy to the at least one set of electrodes.

44. The system of embodiment 43, wherein the electrical energy provided to the at least one set of electrodes is greater under the one arrangement of the relay system than under the other arrangement of the relay system.

45. The system of embodiment 43, wherein in one pulse of electrical energy to the electrodes the relay system is in either the engaged or disengaged arrangement, and in another pulse of the electrical energy to the electrodes the relay system is in the disengaged arrangement.

46. A method of operating an intravascular lithotripsy (IVL) system, the method comprising:

applying a first voltage pulse to at least one set of electrodes;

determining to adjust a stored energy level of the IVL system;

applying another voltage pulse to the at least one set of electrodes using a stored energy magnitude or level different from the first voltage pulse.

47. The method of embodiment 46, wherein applying the voltage pulse includes operating an adjustable energy storage system at a first stored energy level to apply electrical energy.

48. The method of embodiment 47, wherein applying the other voltage pulse includes operating the adjustable energy storage system at a second stored energy level to apply electrical energy.

49. The method of embodiment 48, wherein the second stored energy level is greater than the first stored energy level.

50. The method of embodiment 48, wherein the second stored energy level is less than the first stored energy level.

51. The method of embodiment 48, wherein applying the voltage pulse includes arranging a relay system to connect one or more stored energy elements of the adjustable energy storage system.

52. The method of embodiment 51, wherein arranging the relay system to connect the one or more stored energy elements of the adjustable energy storage system includes a maximum number of stored energy elements of the adjustable energy storage system.

53. The method of embodiment 51, wherein arranging the relay system to connect the one or more stored energy elements of the adjustable energy storage system includes less than a maximum number of stored energy elements of the adjustable energy storage system.

54. The method of embodiment 48, wherein applying the other voltage pulse includes arranging a relay system to connect additional stored energy elements of the adjustable energy storage system.

55. The method of embodiment 54, wherein arranging the relay system to connect the additional stored energy elements of the adjustable energy storage system includes a maximum number of stored energy elements of the adjustable energy storage system.

56. The method of embodiment 54, wherein arranging the relay system to connect the additional stored energy elements of the adjustable energy storage system includes less than a maximum number of the stored energy elements of the adjustable energy storage system.

57. The method of embodiment 47, wherein applying the voltage pulse includes arranging a relay system to connect a number of the stored energy elements of the adjustable energy storage system.

58. The method of embodiment 57, wherein arranging the relay system to connect the number of the stored energy elements of the adjustable energy storage system includes a maximum number of the stored energy elements of the adjustable energy storage system.

59. The method of embodiment 58, wherein applying the other voltage pulse includes operating the adjustable energy storage system at another stored energy magnitude to apply electrical energy.

60. The method of embodiment 57, wherein arranging the relay system to connect the number of the stored energy elements of the adjustable energy storage system includes less than a maximum number of the stored energy elements of the adjustable energy storage system.

61. The method of embodiment 60, wherein applying the other voltage pulse includes operating the adjustable energy storage system at another stored energy magnitude to apply electrical energy.

62. An intravascular lithotripsy system comprising:

at least one set of spaced-apart electrodes for arrangement within a body lumen while disposed within a fluid-fillable member configured to contain a conductive fluid;

an electric pulse generation system for providing electrical energy to the at least one set of spaced-apart electrodes to generate spark for intravascular lithotripsy (IVL) therapy, the electric pulse generation system including an IVL control system comprising a processor for executing instructions stored on memory and communications circuitry configured for communication of signals based on commands from the processor, the IVL control system including a charge control system for controlling electrical charging of a discharge system.

63. The system of embodiment 62, wherein the charge control system includes low voltage power regulator arranged to receive and control low voltage power for output for conversion to high voltage power.

64. The system of embodiment 63, wherein the charge control system receives a modulated control signal for controlling output of low voltage power for conversion to high voltage power.

65. The system of embodiment 63, wherein the charge control system is arranged to apply the modulated control signal with feedback of the output of low voltage power.

66. The system of embodiment 63, wherein the modulated control signal is a high frequency pulse width modulated signal.

67. The system of embodiment 61, wherein the charge control system includes a converter arranged to receive low voltage power and to convert low voltage power to high voltage power for communication to the discharge system.

68. The system of embodiment 67, wherein the converter is a DC-DC converter.

69. The system of embodiment 62, wherein the charge control system is configured to provide variable voltage power to the discharge system at different voltage level for consecutive cycles of charge.

70. The system of embodiment 62, wherein the discharge system includes a energy storage system and the charge control system is configured to provide variable voltage power to the discharge system at different voltage for consecutive cycles of charge after stored energy discharge discharge.

71. An intravascular lithotripsy system comprising:

at least one set of spaced-apart electrodes for arrangement within a body lumen while disposed within a fluid-fillable member configured to contain a conductive fluid;

an electric pulse generation system for providing electrical energy to the at least one set of spaced-apart electrodes to generate spark for intravascular lithotripsy (IVL) therapy, the electric pulse generation system including an IVL control system comprising a processor for executing instructions stored on memory and communications circuitry configured for communication of signals based on commands from the processor, the IVL control system including an electrical discharge system for selectively communicating high voltage discharge to the at least one set of electrodes.

72. The system of embodiment 71, wherein the electrical discharge system comprises a discharge switching system operable to modulate communication of high voltage power to the at least one set of electrodes for IVL therapy.

73. The system of embodiment 72, wherein the discharge switching system includes at least one gate-controlled switch operable by processor signal to selectively permit communication of high voltage power to the at least one set of electrodes for IVL therapy.

74. The system of embodiment 73, where the at least one gate controlled switch is an insulated gate bipolar transistor.

75. The system of embodiment 73, where the at least one gate controlled switch is selectively operable in a permissive state permitting communication of high voltage power to the at least one set of electrodes for IVL therapy, and a nonpermissive state blocking against communication of high voltage power to the at least one set of electrodes for IVL therapy.

76. The system of embodiment 71, wherein the electrical discharge system comprises an energy storage system for charging of high voltage energy for discharge to the at least one set of electrodes.

77. The system of embodiment 76, wherein the electrical discharge system comprises a discharge switching system operable to modulate communication of high voltage power from the energy storage system to the at least one set of electrodes for IVL therapy.

78. A method of operating an intravascular lithotripsy system, the method comprising:

assessing the stored energy state of a energy storage system of an intravascular lithotripsy (IVL) system to determine stored energy;

delivering a voltage pulse to at least one set of electrodes of the IVL system;

assessing the remaining energy state of the energy storage system of the IVL system to determine remaining energy; and comparing the energy states assessed to determine the energy of the voltage pulse.

79. The method of embodiment 78, wherein assessing the energy state to determine stored energy includes determining a voltage level of the energy storage system.

80. The method of embodiment 79, wherein assessing the energy state to determine stored energy includes determining a level of energy stored within the energy storage system based on the voltage level of the energy storage system.

81. The method of embodiment 78, wherein assessing the energy state to determine remaining energy includes determining a voltage level of the energy storage system.

82. The method of embodiment 81, wherein assessing the energy state to determine remaining energy includes determining a level of energy remaining within the energy storage system based on the voltage level of the energy storage system.

83. The method of embodiment 78, wherein comparing the energy states assessed includes determining the difference between the stored and remaining energy states of the energy storage system as a discharged energy.

84. The method of embodiment 83, wherein comparing the energy states assessed includes comparing the discharged energy with a threshold value.

85. The method of embodiment 84, wherein responsive to a determination that the discharged energy is equal to or greater than the threshold value, determining that sufficient spark has been generated.

86. The method of embodiment 84, wherein responsive to a determination that the discharged energy is less than the threshold value, determining that insufficient spark has been generated.

87. The method of embodiment 78, further comprising determining parameters of a further voltage pulse based on the comparison of energy states.

88. The method of embodiment 87, wherein determining parameters of the further voltage pulse includes, responsive to determination that the voltage pulse generated sufficient spark, maintaining one or more parameters of the voltage pulse for the further voltage pulse.

89. The method of embodiment 88, further comprising delivering the further voltage pulse based on the one or more maintained parameters.

90. The method of embodiment 89, repeating assessing the remaining energy state of the energy storage system of the IVL system to determine remaining energy, after delivery of the further voltage pulse.

91. The method of embodiment 87, wherein determining parameters of the further voltage pulse includes, responsive to determination that the voltage pulse generated insufficient spark, changing one or more parameters of the voltage pulse for the further voltage spark.

92. The method of embodiment 91, wherein changing one or more parameters includes changing duration of pulse for the further voltage pulse.

93. The method of embodiment 92, wherein changing duration includes increasing duration of the further voltage pulse greater than a duration of the voltage pulse.

94. The method of embodiment 92, further comprising delivering the further voltage pulse based on the one or more changed parameters.

95. The method of embodiment 94, repeating assessing the remaining energy state of the energy storage system of the IVL system to determine remaining energy, after delivery of the further voltage pulse.

96. The method of embodiment 78, wherein assessing the energy state to determine stored energy includes assessing the energy state of the energy storage system after an earlier voltage pulse has been delivered.

97. An intravascular lithotripsy system comprising:

at least one set of spaced-apart electrodes for arrangement within a body lumen while disposed within a fluid-fillable member configured to contain a conductive fluid;

an electric pulse generation system for providing electrical energy to the at least one set of spaced-apart electrodes to generate spark for intravascular lithotripsy (IVL) therapy, the electric pulse generation system including an IVL control system comprising a processor for executing instructions stored on memory and communications circuitry configured for communication of signals based on commands from the processor, wherein the IVL control system is configured to:

assess the stored energy state of a energy storage system of the IVL system to determine stored energy;

deliver a voltage pulse to at least one set of electrodes of the IVL system;

assess the remaining energy state of the energy storage system of the IVL system to determine remaining energy; and compare the energy states assessed to determine the energy of the voltage pulse.

98. The system of embodiment 97, wherein assessing the energy state to determine stored energy includes determining a voltage level of the energy storage system.

99. The system of embodiment 98, wherein assessing the energy state to determine stored energy includes determining a level of energy stored within the energy storage system based on the voltage level of the energy storage system.

100. The system of embodiment 97, wherein assessing the energy state to determine remaining energy includes determining a voltage level of the energy storage system.

101. The system of embodiment 100, wherein assessing the energy state to determine remaining energy includes determining an energy remaining within the energy storage system based on the voltage level of the energy storage system.

102. The system of embodiment 97, wherein comparing the energy states assessed includes determining the difference between the stored and remaining energy states of the energy storage system as a discharged energy.

103. The system of embodiment 102, wherein comparing the energy states assessed includes comparing the discharged energy with a threshold value.

104. The system of embodiment 103, wherein responsive to a determination that the discharged energy is equal to or greater than the threshold value, determining that sufficient spark has been generated.

105. The system of embodiment 103, wherein responsive to a determination that the discharged energy is less than the threshold value, determining that insufficient spark has been generated.

106. The system of embodiment 97, further comprising determining parameters of a further voltage pulse based on the comparison of energy states.

107. The system of embodiment 106, wherein determining parameters of the further voltage pulse includes, responsive to determination that the voltage pulse generated sufficient spark, maintaining one or more parameters of the further voltage pulse.

108. The system of embodiment 107, further comprising delivering the further voltage pulse based on the one or more maintained parameters.

109. The system of embodiment 108, repeating assessing the remaining energy state of the energy storage system of the IVL system to determine remaining energy, after delivery the further voltage pulse.

110. The method of embodiment 106, wherein determining parameters of the further voltage pulse includes, responsive to determination that the voltage pulse generated insufficient spark, changing one or more parameters of the voltage pulse for the further voltage spark.

111. The method of embodiment 110, wherein changing one or more parameters includes changing duration of pulse for the further voltage pulse.

112. The method of embodiment 111, wherein changing duration includes increasing duration of the further voltage pulse greater than a duration of the voltage pulse.

113. The method of embodiment 111, further comprising delivering the further voltage pulse based on the one or more changed parameters.

114. The method of embodiment 113, repeating assessing the remaining energy state of the energy storage system of the IVL system to determine remaining energy, after delivery of the further voltage pulse.

115. An intravascular lithotripsy system comprising:
- at least one set of spaced-apart electrodes for arrangement within a body lumen while disposed within a fluid-fillable member configured to contain a conductive fluid;
- an electric pulse generation system for providing electrical energy to the at least one set of spaced-apart electrodes to generate spark for intravascular lithotripsy (IVL) therapy, the electric pulse generation system including an IVL control system comprising a processor for executing instructions stored on memory and communications circuitry configured for communication of signals based on commands from the processor, wherein the electric pulse generation system comprises an electrical power system including an AC mains and a DC power storage system, wherein the AC mains are configured for connection with a AC power receptacle to receive AC power from infrastructure, and the DC power storage system is configured to receive AC power from the AC mains and to convert AC power to DC power for charging a DC power storage device of the DC power storage system,
- wherein the electric pulse generation system is configured to selectively provide power from the AC mains or the DC power storage system for IVL operations.

116. The system of embodiment 115, wherein IVL operations includes high voltage pulse provided to the at least one set of electrodes.

117. The system of embodiment 115, wherein the DC power storage device comprises a chemical battery.

118. The system of embodiment 115, wherein the electrical power system is configured to selectively provide power for IVL operations from stored power of the DC power storage device, from the DC power storage device while connected to receive charging power from the AC mains, or directly from the AC mains converted to DC power without the DC power storage device.

The description of devices, systems, and method and related applications as set forth herein is illustrative and is not intended to limit the scope of the invention. Features of various embodiments may be combined with other embodiments within the contemplation of this invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

We claim:

1. An intravascular lithotripsy ("IVL") system comprising:
- a catheter assembly comprising an elongate member defining a lumen and a fluid-fillable member configured to contain fluid, the fluid-fillable member associated with a longitudinal end region of the elongate member, the catheter assembly configured to at least partially fill the fluid-fillable member with an IVL fluid medium to facilitate IVL therapy;
- a pulse generation system comprising a voltage pulse generator in operative communication with an IVL control system comprising a processor for executing instructions stored on memory and circuitry configured to communicate signals based on operation of the processor for providing IVL therapy to a patient,
- at least one set of spaced-apart electrodes arranged within the fluid-filled member for submerging within the IVL fluid medium and in operative communication with the pulse generation system;
- wherein the pulse generation system is configured to generate one or more voltage pulses and apply the generated one or more voltage pulses to the at least one spaced-apart electrodes under initial control settings, to determine that a threshold parameter comprising the maximum plurality of voltage pulses resulting in an electrical arc between the at least one set of spaced-apart electrodes is achieved under the initial control settings, and to determine second control settings comprising an increase of a voltage pulse magnitude in response to a determination that the threshold parameter is achieved,
- wherein the pulse generation system is configured to generate one or more voltage pulses under the second control settings and apply electrical energy generated by the one or more voltage pulses under the second control settings to the at least one set of spaced-apart electrodes.

2. The IVL system of claim 1, wherein the IVL control system is comprises circuitry-to terminate application of the electrical energy to the at least one set of spaced-apart electrodes, responsive to the determination that the threshold parameter is achieved.

3. The IVL system of claim 1, wherein the IVL control system is configured to repeat the determination that the threshold parameter is achieved after the application of the generated electrical energy to the at least one set of spaced-apart electrodes under the second control settings and, responsive to the determination that the threshold parameter is not achieved, generate one or more voltage pulses under the second control settings and apply the generated electrical energy under the second control settings to the at least one set of spaced-apart electrodes.

4. The IVL system of claim 3, wherein the IVL control system is configured to determine whether a predetermined duration of the application of the generated electrical energy to the at least one set of spaced-apart electrodes is achieved.

5. The IVL system of claim 4, wherein, responsive to a determination that the predetermined maximum duration of application of the generated electrical energy to the at least one set of spaced-apart electrodes is achieved, the IVL control system is configured to increase the voltage pulse magnitude by a predetermined magnitude.

6. The IVL system of claim 5, wherein the IVL control system is configured to determine if the generated voltage pulse magnitude has achieved a maximum threshold.

7. The IVL system of claim 6, wherein, responsive to the determination that the generated voltage magnitude has achieved the maximum threshold, the IVL control system is configured to adjust the duration of application of the generated electrical energy to the at least one set of spaced-apart electrodes.

8. The IVL system of claim 7, wherein the IVL control system is configured to adjust the duration of application of the generated electrical energy to the at least one set of spaced-apart electrodes to the duration of the initial control settings.

9. The system of claim 1, wherein the application of electrical energy to the at least one set of spaced-apart electrodes is generated by a voltage pulse having a voltage magnitude and duration.

10. The system of claim 9, wherein the electrical energy applied to the at least one set of spaced-apart electrodes is generated by a voltage pulse having a duration that is controlled by the IVL control system to be within the range of about 0.1 microseconds to about 2 microseconds.

11. The system of claim 9, wherein the voltage magnitude that is controlled by the IVL control system to be within the range of about 500 volts to about 4000 volts.

12. A method of operating an intravascular lithotripsy ("IVL") system having a catheter assembly comprising an elongate member defining a lumen and a fluid-fillable member configured to contain fluid therein and that is associated with a longitudinal end region of the elongate member, the catheter assembly configured to at least partially fill the fluid-fillable member with an IVL fluid medium to facilitate IVL therapy, at least one set of spaced-apart electrodes for arrangement within the fluid-fillable member for submerging within the IVL fluid medium, and a voltage pulse generator in operative communication with the at least one set of spaced-apart electrodes and in operative communication with an IVL control system comprising a processor configured to execute instructions stored on memory and communications circuitry configured to communicate signals based on operation of the processor for providing IVL therapy to a patient, the method comprising:

generating voltage pulses and applying electrical energy generated by the voltage pulses under initial electrical settings comprising voltage pulse magnitude and voltage pulse duration of application of the generated electrical energy to the at least one set of spaced-apart electrodes;

determining that a predetermined maximum plurality of electrical arcs produced between the at least one set of spaced-apart electrodes is not achieved under the initial electrical settings;

increasing a voltage pulse magnitude of the electrical settings in response to a determination that the predetermined maximum plurality of produced electrical arcs is not achieved; and terminating the generating of the voltage pulses in response to a subsequent determination that the predetermined maximum plurality of produced electrical arcs is achieved.

13. A method of operating an intravascular lithotripsy ("IVL") system, the method comprising:

applying plural pulses of initial electrical energy to at least one set of electrodes of an IVL system;

determining that a threshold plurality of pulses is not achieved; and responsive to determination that the threshold plurality of pulses is not achieved, increasing a duration of a pulse of electrical energy for application to the at least one set of electrodes.

14. An intravascular lithotripsy ("IVL") system comprising:

at least one set of spaced-apart electrodes for arrangement within a body lumen while disposed within a fluid-fillable member configured to contain fluid therein;

an electric pulse generation system for providing electrical energy to the at least one set of spaced-apart electrodes configured to generate electrical arcs for IVL therapy, the electric pulse generation system including a voltage pulse generator in operative communication with the at least one set of spaced-apart electrodes and in operative communication with an IVL control system comprising a processor for executing instructions stored on memory and circuitry configured for communication of signals based on operation of the processor, the IVL control system configured to:

initiate one or more voltage pulses having electrical energy, apply the electrical energy generated by the initiated one or more voltage pulses to the at least one set of electrodes, determine that a threshold parameter is not achieved, and responsive to determination that the threshold parameter is not achieved, increase a duration of application of the generated electrical energy and apply the generated electrical energy to the at least one set of spaced-apart electrodes for the increased duration.

15. The IVL system of claim 14, wherein the IVL control system is configured to re-apply initial electrical energy to the at least one set of electrodes, responsive to determination that the threshold parameter is achieved.

16. The IVL system of claim 15, wherein the threshold parameter is a value of current for achieving an electrical arc between the at least one set of spaced-apart electrodes.

17. The IVL system of claim 16, wherein the threshold parameter value of current is about 20 amperes.

18. The IVL system of claim 15, wherein the IVL control system is configured to determine if the generated voltage magnitude has achieved a maximum threshold.

19. The IVL system of claim 18, wherein, responsive to a determination that the generated voltage magnitude has achieved the maximum threshold, the IVL control system is configured to adjust the duration of application of the generated electrical energy to the at least one set of spaced-apart electrodes.

20. The IVL system of claim 19, wherein the IVL control system is configured to adjust the duration of application of the generated electrical energy to the at least one set of spaced-apart electrodes to the duration of the initial control settings.

21. The IVL system of claim 1, wherein an application of electrical energy to the at least one set of spaced-apart electrodes is generated by a voltage pulse having a voltage magnitude and duration.

22. The system of claim 21, wherein the electrical energy applied to the at least one set of spaced-apart electrodes is generated by a voltage pulse having a duration that is controlled by the IVL control system to be within the range of about 0.1 microseconds to about 2 microseconds.

23. The system of claim 21, wherein the voltage magnitude that is controlled by the IVL control system to be within the range of about 500 volts to about 4000 volts.

* * * * *